United States Patent
Prausnitz et al.

(10) Patent No.: US 11,504,431 B2
(45) Date of Patent: Nov. 22, 2022

(54) FORMULATIONS FOR THE SUPRACHOROIDAL SPACE OF AN EYE AND METHODS

(71) Applicants: Emory University, Atlanta, GA (US); Georgia Tech Research Corporation, Atlanta, GA (US)

(72) Inventors: Mark R. Prausnitz, Atlanta, GA (US); Bryce Chiang, Atlanta, GA (US)

(73) Assignees: Emory University, Atlanta, GA (US); Georgia Tech Research Corporation, Atlanta, GA (US)

( * ) Notice: Subject to any disclaimer, the term of this patent is extended or adjusted under 35 U.S.C. 154(b) by 90 days.

(21) Appl. No.: 16/318,804

(22) PCT Filed: Jul. 20, 2017

(86) PCT No.: PCT/US2017/043176
§ 371 (c)(1),
(2) Date: Jan. 18, 2019

(87) PCT Pub. No.: WO2018/017899
PCT Pub. Date: Jan. 25, 2018

(65) Prior Publication Data
US 2019/0240336 A1  Aug. 8, 2019

Related U.S. Application Data

(60) Provisional application No. 62/364,470, filed on Jul. 20, 2016.

(51) Int. Cl.
| A61K 9/00 | (2006.01) |
| A61K 47/38 | (2006.01) |
| A61P 27/02 | (2006.01) |
| C07K 16/00 | (2006.01) |
| A61K 9/06 | (2006.01) |
| A61K 9/08 | (2006.01) |
| A61K 47/10 | (2017.01) |
| A61M 5/315 | (2006.01) |

(52) U.S. Cl.
CPC ........... *A61K 47/38* (2013.01); *A61K 9/0021* (2013.01); *A61K 9/0048* (2013.01); *A61K 9/06* (2013.01); *A61K 9/08* (2013.01); *A61K 47/10* (2013.01); *A61P 27/02* (2018.01); *C07K 16/00* (2013.01); *A61M 5/31531* (2013.01)

(58) Field of Classification Search
CPC ...... A61K 9/00; A61K 9/0002; A61K 9/0012; A61K 9/0019; A61K 9/0024; A61K 9/0051; A61K 9/0048
See application file for complete search history.

(56) References Cited

U.S. PATENT DOCUMENTS

| 2005/0208103 | A1 | 9/2005 | Adamis et al. | |
| 2007/0202186 | A1* | 8/2007 | Yamamoto | A61K 31/722 424/490 |
| 2010/0098772 | A1 | 4/2010 | Robinson et al. | |
| 2013/0280272 | A1 | 10/2013 | Trogden et al. | |
| 2014/0017244 | A1 | 1/2014 | Duerr et al. | |
| 2014/0120058 | A1* | 5/2014 | O'Shea | A61K 47/595 424/78.37 |
| 2016/0082129 | A1 | 3/2016 | Peters | |
| 2016/0166504 | A1* | 6/2016 | Jarrett | A61K 9/0051 424/490 |

FOREIGN PATENT DOCUMENTS

| WO | 2005072701 A1 | 8/2005 | |
| WO | 2015/095772 A2 | 6/2015 | |
| WO | WO-2015095772 A2 * | 6/2015 | ........... A61K 31/137 |

OTHER PUBLICATIONS

PCT International Search Report and Written Opinion for PCT Application No. PCT/US2017/043176 dated Oct. 10, 2017 (11 pages).
Patel R.S. et al., "Targeted Administration into the Suprachoroidal Space Using a Microneedle for Drug Delivery to the Posterior Segment of the Eye", Physiology and Pharmacology, Investigative Ophthalmology & Visual Science, July 2012, vol. 53. No. 8, pp. 4433-4441.
Supplementary European Search Report of European Patent Application 17831914 dated Feb. 5, 2020.

* cited by examiner

*Primary Examiner* — Micah Paul Young
(74) *Attorney, Agent, or Firm* — Eversheds Sutherland (US) LLP

(57) ABSTRACT

Provided herein are fluid formulations for administration to a suprachoroidal space of an eye of a patient. The fluid formulations may include a pharmaceutical agent, a binding molecule, or a combination thereof. The pharmaceutical agent and the binding molecule may be bonded to each other covalently, non-covalently, or a combination thereof. The pharmaceutical agent may be configured to bond to an ocular tissue. The binding molecule may be configured to bond to an ocular tissue. Methods of administering the fluid formulations, methods of expanding a suprachoroidal space, and methods of reducing the minimum force to separate the sclera and choroid are provided.

18 Claims, 11 Drawing Sheets

- ○ FLUORESCEIN
- ▼ 70 kDa FITC-DEXTRAN
- △ FITC-BEVACIZUMAB
- ● 500 kDa FITC-DEXTRAN
- ■ 2 MDa FITC-DEXTRAN
- ⬢ 20 nm NANOSPHERES

FORMULATIONS FOR THE SUPRACHOROIDAL SPACE OF AN EYE AND METHODS

CROSS-REFERENCE TO RELATED APPLICATIONS

This application claims priority to U.S. Provisional Patent Application No. 62/364,470, filed Jul. 20, 2016, which is incorporated herein by reference.

STATEMENT REGARDING FEDERALLY SPONSORED RESEARCH OR DEVELOPMENT

This invention was made with government support under grant numbers EY022097, EY025154, and EY017045 awarded by the National Institutes of Health. The government has certain rights in the invention.

BACKGROUND

The suprachoroidal space (SCS) is a potential space found between the sclera and choroid. Due to its close proximity to the ciliary body, choroid, retina, and sclera, this space has drawn attention as a possible site for targeted drug delivery, placement of glaucoma drainage devices, and implantation of retinal prostheses. As a site of drug administration, delivery into the SCS is noted for high bioavailability at targeted tissues in posterior-segment diseases, as well as fast clearance by the choroidal vasculature. Unlike traditional ophthalmic drug delivery techniques, such as topical eye drops and intravitreal injections, SCS injection can enable targeted delivery to the choroid, retinal pigment epithelium, or retina with high bioavailability. Additional advantages of SCS delivery include increased bioavailability, dose sparing, avoiding the visual axis, or a combination thereof.

Access to the SCS is possible via surgical procedures of varying complexity, and microneedle injections that offer greater simplicity. A hollow microneedle with a length similar to the thickness of the sclera can be used to access the SCS, while typically preventing penetration deeper into the eye. Microneedle injections can be performed by ophthalmologists in an outpatient clinic setting, similar to the intravitreal injection procedure.

Although many studies have investigated the two-dimensional circumferential spread of particles and molecules within the SCS, few have studied the third dimension: the distensibility of the choroid off the sclera, which is known as the SCS thickness. Seiler et al. measured the maximum SCS thickness over the injection site in ex vivo porcine and canine eyes, and found that there was no difference in thickness with three injection volumes, especially once the eyes were inflated to a physiological intraocular pressure (Seiler G. S. et al., *Invest Ophthalmol Vis Sci* 2011; 52:5730-5736).

When administering drugs via the SCS, it can be important to control the area over which the drug formulations spread within the SCS. This targeting within the SCS may be used to treat diseased tissue while sparing non-diseased tissue. In some cases, it is desirable to have drug distributed over a large area of the SCS to broadly deliver drug to the chorioretina (e.g., to treat posterior uveitis). In other cases, it may be desirable to localize the drug near the site of injection (e.g., to treat glaucoma).

Most molecules injected into the SCS are cleared into systemic circulation via the choriocapillaris or transsclerally into the subconjunctival space. Drugs cleared via the choroid can interact with possible drug targets in that tissue, and possibly diffuse across retinal pigment epithelium into retina, where additional drug targets are also located. Drugs cleared across sclera (or via leakage pathways) typically do not enter choroid or retina, and therefore do not reach targets in those tissues.

Residence time in the SCS may depend on what is injected. It is known that molecules typically are cleared from the SCS within one day and that solid particles are not cleared at all.

Previous studies have used the two-dimensional (2D) circumferential spread of particles injected into the SCS as the primary metric of distribution (see, e.g., Kim, Y. C. et al. *Adv Healthc Mater* 2014, 3, 1272-1282). Although many studies have investigated the distribution of particles (Chen et al., 2015; Kim et al., 2014a; Kim et al., 2015; Patel et al., 2012; Patel et al., 2011) and molecules (Kim et al., 2014b; Olsen et al., 2011; Patel et al., 2012; Tyagi et al., 2013; Wang et al., 2012) independently, few, if any, studies have examined the distribution of particles and molecules injected into the SCS simultaneously, or imaged the distribution of polymeric formulation excipients in the SCS.

The distribution of molecules and particles injected into the SCS have also been studied to obtain a better understanding of flow within this space (see, e.g., Patel S. R. et al. *Invest Ophthalmol Vis Sci* 2012; 53:4433-4441). However, data on how fluid and molecules leave this space are less known. Previous studies have focused only on the role of the choroid in clearing the SCS, and generally have concluded that it did play a role. However, the roles of other routes of clearance have not been considered, and no comparative quantification of the roles of various routes of clearance from SCS have been reported before.

There remains a need for (i) improved methods of delaying the clearance time of a material from the SCS, including methods that do not rely on solid particles, (ii) materials that are designed in view of a likely clearance mechanism from the SCS, (iii) easier access to the SCS, and (iv) methods of expanding the SCS, especially in a manner that is simple, reliable, or a combination thereof.

BRIEF SUMMARY

In one aspect, fluid formulations for administration to a SCS of an eye of a patient are provided. In some embodiments, the fluid formulations include a pharmaceutical agent and a binding molecule to which the pharmaceutical agent is covalently bonded, non-covalently bonded, or a combination thereof. The pharmaceutical agent and the binding molecule together may have (i) a hydrodynamic radius of at least 7 nm, (ii) a combined molecular weight of at least 500 kDa, or (iii) a combination thereof. A pharmaceutical agent and a binding molecule may be components of a gel. A binding molecule may have a non-particulate structure. A pharmaceutical agent and a binding molecule may form a prodrug, wherein after administration to a SCS, the pharmaceutical agent and the binding molecule may disassociate by chemical reaction, enzymatic activity, an alteration of an attractive and/or repulsive interaction, or a combination thereof.

In some embodiments, the fluid formulations include a pharmaceutical agent and a liquid medium in which the pharmaceutical agent is dissolved. The formulation may be configured to release the pharmaceutical agent from the formulation controlled by the rate at which the pharmaceutical agent partitions from the liquid medium into an ocular fluid of the SCS.

In some embodiments, the fluid formulations include a pharmaceutical agent including at least one feature that is configured to bond the pharmaceutical agent to an ocular tissue, thereby slowing the rate of clearance of the pharmaceutical agent from the SCS. The pharmaceutical agent may be configured to bond to the ocular tissue covalently, non-covalently, or a combination thereof. The at least one feature of the pharmaceutical agent may include a hydrophobic moiety, a charged moiety, a $pK_a$ effective to bond the pharmaceutical agent to the ocular tissue, or a combination thereof.

In some embodiments, the fluid formulations include a binding molecule having (i) a hydrodynamic radius of at least 7 nm, (ii) a molecular weight of at least 500 kDa, or (iii) a combination thereof. The binding molecule may be configured to bond to a material in the SCS covalently, non-covalently, or a combination thereof, to delay or prevent an interaction of the material with another material in the eye. The binding molecule may act as a "molecular sponge" upon administration to the SCS. The material in the SCS to which the binding molecule may be configured to bond may include vascular endothelial growth factor (VEGF).

In another aspect, methods of administering a fluid formulation to an eye of a patient are provided. In some embodiments, the methods include inserting a microneedle into the eye at an insertion site; and infusing a volume of a fluid formulation through the microneedle into the SCS of an eye at the insertion site. The fluid formulation may include a pharmaceutical agent and a binding molecule to which the pharmaceutical agent is covalently bonded, non-covalently bonded, or a combination thereof. The pharmaceutical agent and the binding molecule may together have (i) a hydrodynamic radius of at least 7 nm, (ii) a combined molecular weight of at least 500 kDa, or (iii) a combination thereof. The pharmaceutical agent administered by the method may have a clearance time that is at least 2 times greater than a comparative pharmaceutical agent administered in the absence of the binding molecule. The infusing of the volume of the liquid formulation may include, in any order, infusing into the SCS a first part of the fluid formulation comprising the binding molecule; and infusing into the SCS a second part of the fluid formulation comprising the pharmaceutical agent.

In some embodiments, the methods include inserting a microneedle into the eye at an insertion site; and infusing a volume of a fluid formulation through the microneedle into the SCS of the eye at the insertion site, wherein the fluid formulation includes a binding molecule having (i) a hydrodynamic radius of at least 7 nm, (ii) a molecular weight of at least 500 kDa, or (iii) a combination thereof. The binding molecule may be configured to bond to a material in the SCS covalently, non-covalently, or a combination thereof to delay or prevent an interaction of the material with another material in the eye.

In another aspect, methods of expanding a SCS of an eye of a patient are provided. In some embodiments, the methods include inserting a microneedle into the eye at an insertion site; and then infusing through the microneedle into the SCS a first liquid formulation having a viscosity sufficient to expand at least a portion of the SCS to a thickness of about 500 μm to about 3.0 mm for at least two hours after the infusing.

In yet another aspect, methods of enhancing the delivery of a pharmaceutical agent to a SCS of an eye of a patient are provided. In some embodiments, the methods include inserting a microneedle into the eye at an insertion site; infusing through the microneedle into the SCS a volume of a liquid formulation sufficient to reduce by at least 25% the minimum force to separate the sclera and choroid; and then disposing a pharmaceutical agent in the SCS. In some embodiments, the minimum force to separate the sclera and choroid is reduced by about 30% to about 80%.

DETAILED DESCRIPTION

Figure 1:
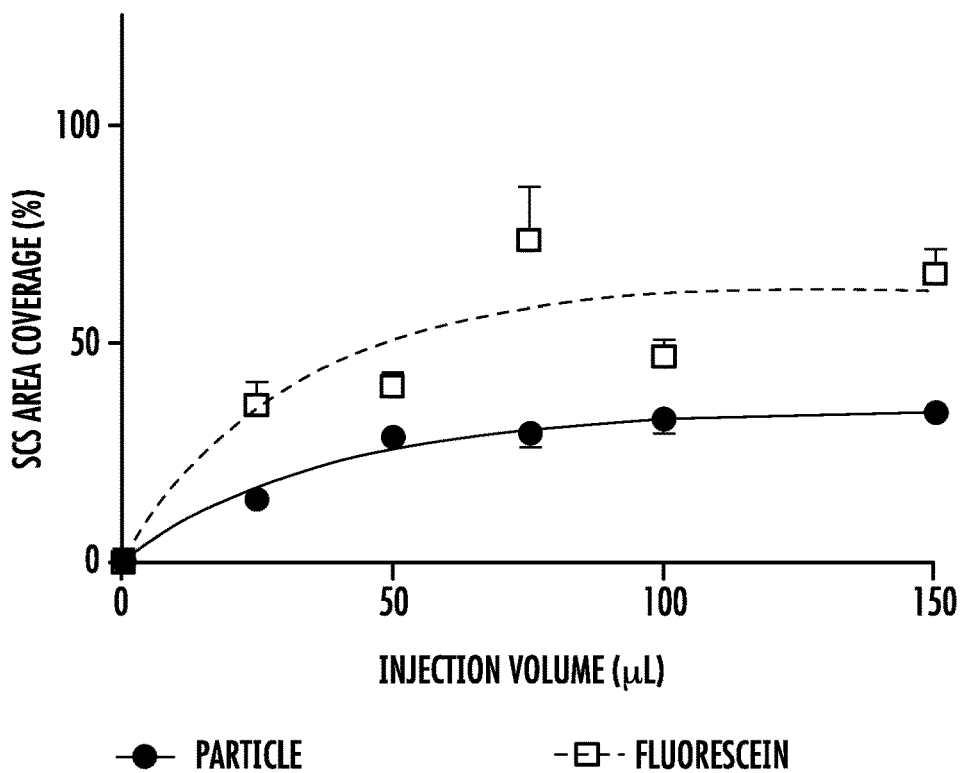
FIG. 1 depicts a quantification of the percent area (mean±SEM, N=3-5 replicates) of SCS covered by red particles or fluorescein in several embodiments.

Provided herein are fluid formulations having a delayed clearance time from the SCS, including fluid formulations having a non-particulate structure, such as a gel. The fluid formulations may include a pharmaceutical agent, a binding molecule, or a pharmaceutical agent and a binding molecule that are bonded to each other covalently, non-covalently, or a combination thereof. The pharmaceutical agent, the binding molecule, or a combination thereof may independently be configured to bond covalently and/or non-covalently to one or more ocular tissues, one or more materials in the SCS, or a combination thereof.

Also provided herein are methods of expanding the SCS, which may include infusing a liquid formulation in the SCS having a viscosity sufficient to expand at least a portion of the SCS. Unexpectedly, an SCS expands to accommodate the infusion of a low-viscosity liquid formulation, but the infusion of a greater volume of the low-viscosity liquid formulation does not cause further expansion of the SCS. The greater volume of the low-viscosity fluid formulation likely is accommodated by increasing the area of fluid spread in the SCS without further expanding the SCS. Surprisingly, the infusion into the SCS of relatively viscous liquid formulations can expand SCS thickness beyond the SCS thickness achieved when a low-viscosity liquid formulation is infused into the SCS. Increasing the SCS thickness with a relatively viscous liquid formulation may ease access to the SCS, thereby easing or permitting the disposal of a device in the SCS.

Also provided herein are methods of easing access to the SCS. The methods may include infusing a volume of a liquid formulation into the SCS to reduce the minimum force required to separate the sclera and the choroid. The reduction of the minimum force may permit greater control over one or more aspects of infusing a pharmaceutical agent, binding molecule, or a combination thereof into the SCS.

As used herein, the term "suprachoroidal space," or SCS, which is synonymous with suprachoroid or suprachoroidia, describes the potential space in the region of the eye disposed between the sclera and choroid. This region primarily is composed of packed layers of long pigmented processes derived from each of two adjacent tissues; however, a space can develop in this region as a result of fluid or other material buildup in the suprachoroidal space and the adjacent tissues. The "supraciliary space," as used herein, is encompassed by the SCS, and refers to the most anterior portion of the suprachoroidal space adjacent to the ciliary body, trabecular meshwork and limbus.

In some embodiments, the formulations herein are delivered to the SCS using non-surgical methods (e.g., microneedle devices and methods). As used herein, "non-surgical" methods refer to methods of drug delivery that do not require general anesthesia and/or retrobulbar anesthesia (also referred to as a retrobulbar block). Alternatively or additionally, a "non-surgical" method is performed with an instrument having a diameter of 28 gauge or smaller. Alternatively or additionally, "non-surgical" methods do not require a guidance mechanism that is typically required for ocular drug delivery via a shunt or cannula.

Fluid Formulations

Fluid formulations are provided herein that may be administered to a SCS of an eye of a patient. As used herein, the term "patient" refers to a mammal, including humans. In some embodiments, the patient is human, and may in some instances refer to other animals. The fluid formulations may include (i) a pharmaceutical agent, (ii) a binding molecule, or (iii) a pharmaceutical agent and a binding molecule.

When the fluid formulations include a pharmaceutical agent and a binding molecule, the pharmaceutical agent and the binding molecule may be covalently bonded to each other, non-covalently bonded to each other, or a combination thereof. The pharmaceutical agent and the binding molecule are covalently bonded to each other when the sharing of electrons by at least one atom of the pharmaceutical agent and at least one atom of the binding molecules results in the formation of a covalent bond. The pharmaceutical agent and the binding molecule are non-covalently bonded to each other when attractive interaction occurs between at least a portion of the pharmaceutical agent and at least a portion of the binding molecule. The attractive interaction may include ionic interaction, hydrogen bonding, pi-pi bonding, hydrophobic interaction, hydrophilic interaction, electrostatic interaction, van der Waals interaction, receptor/ligand interaction, or a combination thereof. When the pharmaceutical agent and the binding molecule are non-covalently bonded, the attractive interaction may prevent diffusion from being the only mechanism by which the pharmaceutical agent dissociates from the binding molecule. The pharmaceutical agent and the binding molecule may be covalently and non-covalently bonded to each other.

In some embodiments, the pharmaceutical agent and the binding molecule—independently or collectively—have one or more features configured to slow clearance from the SCS.

In some embodiments, the pharmaceutical agent and the binding molecule together have (i) a hydrodynamic radius of at least 7 nm, (ii) a combined molecular weight of at least 500 kDa, (iii) a combination thereof. In some embodiments, the pharmaceutical agent has (i) a hydrodynamic radius less than 7 nm and/or (ii) a molecular weight less than 500 kDa, and, upon bonding with the binding molecule covalently, non-covalently, or a combination thereof, the pharmaceutical agent and the binding molecule together have (i) a hydrodynamic radius of at least 7 nm and/or (ii) a combined molecular weight of at least 500 kDa.

When "the pharmaceutical agent and the binding molecule together have a hydrodynamic radius" of a particular value, the particular value may be satisfied by the complex formed by the pharmaceutical agent and the binding molecule; therefore, it may not be necessary for the binding molecule and the pharmaceutical agent to individually meet the limitation.

Not wishing to be bound by any particular theory, it is believed that a hydrodynamic radius may be increased by increasing the degree of branching, the number of double-bonds and/or triple-bonds, or a combination thereof. Therefore, the pharmaceutical agent and/or a binding molecule may have a degree of branching, number of non-single bonds, or a combination thereof that are effective to impart the pharmaceutical agent and/or binding molecule, respectively, with a desired hydrodynamic radius.

In some embodiments, the pharmaceutical agent and the binding molecule are covalently bonded to each other, and together have a hydrodynamic radius of at least 7 nm, at least 8 nm, at least 9 nm, at least 10 nm, at least 12 nm, at least 15 nm, at least 17 nm, at least 20 nm, at least 25 nm, at least 30 nm, at least 35 nm, at least 40 nm, at least 45 nm, at least 50 nm, at least 55 nm, at least 60 nm, at least 65 nm, at least 70 nm, at least 75 nm, at least 80 nm, at least 85 nm, at least 90 nm, at least 95 nm, or at least 100 nm. In particular embodiments, the pharmaceutical agent and the binding molecule are covalently bonded to each other, and have a combined molecular weight of at least 375 kDa and, together, a hydrodynamic radius of at least 7 nm, at least 8 nm, at least 9 nm, at least 10 nm, at least 12 nm, at least 15 nm, at least 17 nm, at least 20 nm, at least 25 nm, at least 30 nm, at least 35 nm, at least 40 nm, at least 45 nm, at least 50 nm, at least 55 nm, at least 60 nm, at least 65 nm, at least 70 nm, at least 75 nm, at least 80 nm, at least 85 nm, at least 90 nm, at least 95 nm, or at least 100 nm. In some embodiments, the pharmaceutical agent and the binding molecule are covalently bonded to each other, and have a combined molecular weight of at least 400 kDa and, together, a hydrodynamic radius of at least 7 nm, at least 8 nm, at least 9 nm, at least 10 nm, at least 12 nm, at least 15 nm, at least 17 nm, at least 20 nm, at least 25 nm, at least 30 nm, at least 35 nm, at least 40 nm, at least 45 nm, at least 50 nm, at least 55 nm, at least 60 nm, at least 65 nm, at least 70 nm, at least 75 nm, at least 80 nm, at least 85 nm, at least 90 nm, at least 95 nm, or at least 100 nm. In additional embodiments, the pharmaceutical agent and the binding molecule are covalently bonded to each other, and have a combined molecular weight of at least 425 kDa and, together, a hydrodynamic radius of at least 7 nm, at least 8 nm, at least 9 nm, at least 10 nm, at least 12 nm, at least 15 nm, at least 17 nm, at least 20 nm, at least 25 nm, at least 30 nm, at least 35 nm, at least 40 nm, at least 45 nm, at least 50 nm, at least 55 nm, at least 60 nm, at least 65 nm, at least 70 nm, at least 75 nm, at least 80 nm, at least 85 nm, at least 90 nm, at least 95 nm, or at least 100 nm. In particular embodiments, the pharmaceutical agent and the binding molecule are covalently bonded to each other, and have a combined molecular weight of at least 450 kDa and, together, a hydrodynamic radius of at least 7 nm, at least 8 nm, at least 9 nm, at least 10 nm, at least 12 nm, at least 15 nm, at least 17 nm, at least 20 nm, at least 25 nm, at least 30 nm, at least 35 nm, at least 40 nm, at least 45 nm, at least 50 nm, at least 55 nm, at least 60 nm, at least 65 nm, at least 70 nm, at least 75 nm, at least 80 nm, at least 85 nm, at least 90 nm, at least 95 nm, or at least 100 nm. In some embodiments, the pharmaceutical agent and the binding molecule are covalently bonded to each other, and have a combined molecular weight of at least 475 kDa and, together, a hydrodynamic radius of at least 7 nm, at least 8 nm, at least 9 nm, at least 10 nm, at least 12 nm, at least 15 nm, at least 17 nm, at least 20 nm, at least 25 nm, at least 30 nm, at least 35 nm, at least 40 nm, at least 45 nm, at least 50 nm, at least 55 nm, at least 60 nm, at least 65 nm, at least 70 nm, at least 75 nm, at least 80 nm, at least 85 nm, at least 90 nm, at least 95 nm, or at least 100 nm. In still further embodiments, the pharmaceutical agent and the binding molecule are covalently bonded to each other, and together have a hydrodynamic radius of at least 7 nm, and a combined molecular weight of at least 375 kDa, at least 400 kDa, at least 425 kDa, at least 450 kDa, or at least 475 kDa.

In some embodiments, the pharmaceutical agent and the binding molecule are covalently bonded to each other, and have a clearance time from the SCS of about 1 day to about 90 days, about 1 day to about 60 days, about 1 day to about 30 days, about 1 day to about 21 days, about 1 day to about 14 days, about 1 day to about 7 days, about 1 day to about 3 days, about 2 days to about 90 days, about 3 days to about 90 days, about 3 days to about 60 days, about 3 days to about 30 days, about 3 days to about 21 days, about 3 days to about 14 days, or about 3 days to about 7 days. In other embodiment, the pharmaceutical agent and the binding molecule are covalently bonded to each other, and have a clearance time from the SCS of about 3 days to about 365 days, about 3 days to about 300 days, about 3 days to about 200 days, about 3 days to about 150 days, about 3 days to about 125 days, about 7 days to about 365 days, about 7 days to about 300 days, about 7 days to about 200 days, about 7 days to about 150 days, about 7 days to about 125 days. The "clearance time from the SCS" of the pharmaceutical agent and the binding molecule is the time required for substantially all of the pharmaceutical agent to escape the SCS. If the pharmaceutical agent and the binding molecule disassociate from each other in the SCS, then the clearance time of the pharmaceutical agent and the binding molecule may differ, but the "clearance time" is the time required for substantially all of the pharmaceutical agent to escape the SCS.

In some embodiments, the pharmaceutical agent and the binding molecule are non-covalently bonded to each other, and together have a hydrodynamic radius of at least 7 nm, at least 8 nm, at least 9 nm, at least 10 nm, at least 12 nm, at least 15 nm, at least 17 nm, at least 20 nm, at least 25 nm, at least 30 nm, at least 35 nm, at least 40 nm, at least 45 nm, at least 50 nm, at least 55 nm, at least 60 nm, at least 65 nm, at least 70 nm, at least 75 nm, at least 80 nm, at least 85 nm, at least 90 nm, at least 95 nm, or at least 100 nm. In particular embodiments, the pharmaceutical agent and the binding molecule are non-covalently bonded to each other, and have a combined molecular weight of at least 375 kDa and, together, a hydrodynamic radius of at least 7 nm, at least 8 nm, at least 9 nm, at least 10 nm, at least 12 nm, at least 15 nm, at least 17 nm, at least 20 nm, at least 25 nm, at least 30 nm, at least 35 nm, at least 40 nm, at least 45 nm, at least 50 nm, at least 55 nm, at least 60 nm, at least 65 nm, at least 70 nm, at least 75 nm, at least 80 nm, at least 85 nm, at least 90 nm, at least 95 nm, or at least 100 nm. In some embodiments, the pharmaceutical agent and the binding molecule are non-covalently bonded to each other, and have a combined molecular weight of at least 400 kDa and, together, a hydrodynamic radius of at least 7 nm, at least 8 nm, at least 9 nm, at least 10 nm, at least 12 nm, at least 15 nm, at least 17 nm, at least 20 nm, at least 25 nm, at least 30 nm, at least 35 nm, at least 40 nm, at least 45 nm, at least 50 nm, at least 55 nm, at least 60 nm, at least 65 nm, at least 70 nm, at least 75 nm, at least 80 nm, at least 85 nm, at least 90 nm, at least 95 nm, or at least 100 nm. In additional embodiments, the pharmaceutical agent and the binding molecule are non-covalently bonded to each other, and have a combined molecular weight of at least 425 kDa and, together, a hydrodynamic radius of at least 7 nm, at least 8 nm, at least 9 nm, at least 10 nm, at least 12 nm, at least 15 nm, at least 17 nm, at least 20 nm, at least 25 nm, at least 30 nm, at least 35 nm, at least 40 nm, at least 45 nm, at least 50 nm, at least 55 nm, at least 60 nm, at least 65 nm, at least 70 nm, at least 75 nm, at least 80 nm, at least 85 nm, at least 90 nm, at least 95 nm, or at least 100 nm. In particular embodiments, the pharmaceutical agent and the binding molecule are non-covalently bonded to each other, and have a combined molecular weight of at least 450 kDa and, together, a hydrodynamic radius of at least 7 nm, at least 8 nm, at least 9 nm, at least 10 nm, at least 12 nm, at least 15 nm, at least 17 nm, at least 20 nm, at least 25 nm, at least 30 nm, at least 35 nm, at least 40 nm, at least 45 nm, at least 50 nm, at least 55 nm, at least 60 nm, at least 65 nm, at least 70 nm, at least 75 nm, at least 80 nm, at least 85 nm, at least 90 nm, at least 95 nm, or at least 100 nm. In some embodiments, the pharmaceutical agent and the binding molecule are non-covalently bonded to each other, and have a combined molecular weight of at least 475 kDa and, together, a hydrodynamic radius of at least 7 nm, at least 8 nm, at least 9 nm, at least 10 nm, at least 12 nm, at least 15 nm, at least 17 nm, at least 20 nm, at least 25 nm, at least 30 nm, at least 35 nm, at least 40 nm, at least 45 nm, at least 50 nm, at least 55 nm, at least 60 nm, at least 65 nm, at least 70 nm, at least 75 nm, at least 80 nm, at least 85 nm, at least 90 nm, at least 95 nm, or at least 100 nm. In still further embodiments, the pharmaceutical agent and the binding molecule are non-covalently bonded to each other, and together have a hydrodynamic radius of at least 7 nm, and a combined molecular weight of at least 375 kDa, at least 400 kDa, at least 425 kDa, at least 450 kDa, or at least 475 kDa.

Not wishing to be bound by any particular theory, it is believed that a pharmaceutical agent, a binding molecule, or a combination thereof having a hydrodynamic radius of at least 7 nm is less likely to be or incapable of being cleared from the SCS by choriocapillaris.

In some embodiments, the pharmaceutical agent and the binding molecule are non-covalently bonded to each other, and have a clearance time from the SCS of about 1 day to about 90 days, about 1 day to about 60 days, about 1 day to about 30 days, about 1 day to about 21 days, about 1 day to about 14 days, about 1 day to about 7 days, about 1 day to about 3 days, about 2 days to about 90 days, about 3 days to about 90 days, about 3 days to about 60 days, about 3 days to about 30 days, about 3 days to about 21 days, about 3 days to about 14 days, or about 3 days to about 7 days. In other embodiment, the pharmaceutical agent and the binding molecule are non-covalently bonded to each other, and have a clearance time from the SCS of about 1 day to about 365 days, about 3 days to about 365 days, about 3 days to about 300 days, about 3 days to about 200 days, about 3 days to about 150 days, about 3 days to about 125 days, about 7 days to about 365 days, about 7 days to about 300 days, about 7 days to about 200 days, about 7 days to about 150 days, about 7 days to about 125 days. The "clearance time from the SCS" of the pharmaceutical agent and the binding molecule is the time required for substantially all of the pharmaceutical agent administered to the SCS to escape the SCS. The pharmaceutical agent and the binding molecule may be cleared from the SCS at different rates, but the "clearance time" is the time required for substantially all of the pharmaceutical agent to escape the SCS.

In some embodiments, the pharmaceutical agent and the binding molecule are covalently bonded to each other, and have a combined molecular weight of at least 500 kDa, at least 750 kDa, at least 1 MDa, at least 1.5 MDa, or at least 2 MDa. In some embodiments, the pharmaceutical agent and the binding molecule are non-covalently bonded to each other, and have a combined molecular weight of at least 500 kDa, at least 750 kDa, at least 1 MDa, at least 1.5 MDa, or at least 2 MDa.

As used herein, the phrase "combined molecular weight" refers to the sum of the molecular weight of the pharmaceutical agent and the molecular weight of the binding agent. When the fluid formulations include a polydisperse polymer, the "molecular weight" refers to the number average molecular weight, unless indicated otherwise.

In some embodiments, the fluid formulations include a pharmaceutical agent and a binding molecule, and the pharmaceutical agent and the binding molecule are configured as a prodrug. As used herein, the term "prodrug" refers to a composition having at least two components that disassociate after administration to a site, such as the SCS. When the pharmaceutical agent and the binding molecule are configured as a prodrug, the pharmaceutical agent and the binding molecule, after administration to the SCS, may disassociate by chemical reaction, enzymatic activity, an alteration of an attractive and/or repulsive interaction, or a combination thereof. A chemical reaction may include any reaction that severs a covalent or non-covalent bond, including, but not limited to, hydrolysis. The pharmaceutical agent and the binding molecule may disassociate over a period of time that may commence at the time of administration to the SCS, or at a certain time after administration to the SCS.

In some embodiments, the fluid formulations provided herein include a pharmaceutical agent that includes at least one feature that is configured to bond the pharmaceutical agent to an ocular tissue, thereby slowing the rate of clearance of the pharmaceutical agent from the SCS. The at least one feature may bond the pharmaceutical agent to the ocular tissue covalently, non-covalently, or a combination thereof. The at least one feature of the pharmaceutical agent and the ocular tissue are covalently bonded to each other when the sharing of electrons by at least one atom of the at least one feature of the pharmaceutical agent and at least one atom of the ocular tissue results in the formation of a covalent bond. The at least one feature of the pharmaceutical agent and the ocular tissue are non-covalently bonded to each other when attractive interaction occurs between the at least one feature of the pharmaceutical agent and at least a portion of the binding molecule. The attractive interaction may include ionic interaction, hydrogen bonding, pi-pi bonding, hydrophobic interaction, hydrophilic interaction, electrostatic interaction, van der Waals interaction, receptor/ligand interaction, or a combination thereof. The ocular tissue generally may include any tissue in the SCS, such as a plurality of cells, an extracellular matrix material, a protein, a polysaccharide, a polynucleic acid, or a combination thereof.

In some embodiments, the at least one feature of the pharmaceutical agent includes a hydrophobic moiety. The hydrophobic moiety of the pharmaceutical agent may generally be any moiety having a hydrophobicity comparable to aliphatic hydrocarbons having at least four carbons, such as $C_4$ to $C_{20}$ alkyls and cycloalkyls; aromatic hydrocarbon groups, such as naphthyls; alkylaryls; haloalkyls of four or more carbons, such as perfluoroalkyls; or polyalkyleneoxy groups, wherein the alkylene is propylene or a higher alkylene. The hydrophobic moiety of the pharmaceutical agent may generally be any moiety having an octanol-water partition coefficient greater than about 1, about 10, about 100, or about 1000. In some embodiments, the hydrophobic moiety may include a hydrophobic monomer or an oligomer or polymer thereof. Suitable hydrophobic monomers include water-insoluble monomers. A "water-insoluble monomer" is a monomer wherein less than 0.2 parts by weight of the monomer will dissolve in 100 parts by weight of water. Non-limiting examples of hydrophobic monomers include the higher alkyl esters of α,β-ethylenically unsaturated carboxylic acids, such as dodecyl acrylate, dodecyl methacrylate, tridecyl acrylate, tridecyl methacrylate, tetradecyl acrylate, tetradecyl methacrylate, octadecyl acrylate, octadecyl methacrylate, ethyl half ester of maleic anhydride, diethyl maleate, and other alkyl esters derived from the reactions of alkanols having from 8 to 20 carbon atoms with ethylenically unsaturated carboxylic acids such as acrylic acid, methacrylic acid, maleic anhydride, fumaric acid, itaconic acid and aconitic acid, alkylaryl esters of ethylenically unsaturated carboxylic acids such as nonyl-α-phenyl acrylate, nonyl-α-phenyl methacrylate, dodecyl-α-phenyl acrylate and dodecyl-α-phenyl methacrylate; N-alkyl, ethylenically unsaturated amides such as N-octadecyl acrylamide, N-octadecyl methacrylamide, N,N-dioctyl acrylamide and similar derivatives thereof; α-olefins such as octene-1, decene-1, dodecene-1 and hexadecene-1; vinyl alkylates wherein alkyl has at least 8 carbons such as vinyl laurate and vinyl stearate; vinyl alkyl ethers such as dodecyl vinyl ether and hexadecyl vinyl ether; N-vinyl amides such as N-vinyl lauramide and N-vinyl stearamide; and ar-alkylstyrenes such as t-butyl styrene.

In some embodiments, the at least one feature of the pharmaceutical agent includes a charged moiety. The charged moiety may be created using any known technique, and generally may include a moiety that is altered to have a different charge (i.e., neutral to positive, neutral to negative, negative to positive, etc.), an increased charged, or decreased charge. In some embodiments, the charged moiety is a moiety that is positively charged under assay or physiological conditions, which are typically neutral or slightly acidic (pH about 5 to about 7). The positively charged moiety may include an amine. In another embodiment, the charged moiety is a moiety that is negatively charged under assay or physiological conditions. The negatively charged moiety may include a carboxylate, a phosphate, or a combination thereof.

In some embodiments, the at least one feature of the pharmaceutical agent includes a hydrophobic moiety and a charged moiety.

In some embodiments, the at least one feature of the pharmaceutical agent has a $pK_a$ effective to bond the pharmaceutical agent to the ocular tissue. The at least one feature may, upon administration to the SCS, alter the charge of the pharmaceutical agent, an ocular tissue, or a combination thereof. A fluid formulation may be configured to adjust the pH of a fluid surrounding the pharmaceutical agent in the SCS, for example, by including a pH buffer. A conventional pH buffer may be used, a binding molecule may be imparted with buffering capability, or a combination thereof.

In some embodiments, the at least one feature of the pharmaceutical agent includes a hydrophobic moiety and a $pK_a$ effective to bond the pharmaceutical agent to the ocular tissue. In some embodiments, the at least one feature of the pharmaceutical agent includes a charged moiety and a $pK_a$ effective to bond the pharmaceutical agent to the ocular tissue.

In some embodiments, the pharmaceutical agent including at least one feature that is configured to bond the pharmaceutical agent to an ocular tissue has a clearance time from the SCS of about 1 day to about 90 days, about 1 day to about 60 days, about 1 day to about 30 days, about 1 day to about 21 days, about 1 day to about 14 days, about 1 day to about 7 days, about 1 day to about 3 days, about 2 days to about 90 days, about 3 days to about 90 days, about 3 days to about 60 days, about 3 days to about 30 days, about 3 days to about 21 days, about 3 days to about 14 days, or about 3 days to about 7 days. In other embodiment, the pharmaceutical agent including at least one feature that is configured to bond the pharmaceutical agent to an ocular tissue has a clearance time from the SCS of about 1 day to about 365 days, about 3 days to about 365 days, about 3 days to about 300 days, about 3 days to about 200 days, about 3 days to about 150 days, about 3 days to about 125 days, about 7 days to about 365 days, about 7 days to about 300 days, about 7 days to about 200 days, about 7 days to about 150 days, about 7 days to about 125 days. The "clearance time from the SCS" of the pharmaceutical agent is the time required for substantially all of the pharmaceutical agent administered to the SCS to escape the SCS.

In some embodiments, the fluid formulations provided herein include a binding molecule having (i) a hydrodynamic radius of at least 7 nm, (ii) a molecular weight of at least 500 kDa, or (iii) a combination thereof. In some embodiments, the binding molecule is configured to bond to a material in the SCS covalently, non-covalently, or a combination thereof, to alter an effect of the material. In some embodiments, the binding molecule is configured to bond to a material in the SCS covalently, non-covalently, or a combination thereof, to delay or prevent an interaction of the material with another material in the eye. The binding molecule may act as a "molecular sponge" upon administration to the SCS. The material having an effect altered by the binding molecule may include any material that a binding molecule may encounter in an SCS. Not wishing to be bound by any particular theory, it is believed that the binding molecule may bond to the material in the SCS, thereby converting the material from an unbound state to a bound state. The bound state of the material may prevent or reduce the ability of the material to achieve one or more functions, including undesirable functions.

In some embodiments, the material in the SCS to which the binding molecule is configured to bond includes vascular endothelial growth factor (VEGF).

Not wishing to be bound by any particular theory, it is believed that it may be desirable in certain circumstances to lower the concentration of VEGF (or one or more other materials) in the eye, particularly the SCS, choroid, retina, or a combination thereof. Macular degeneration and other ocular indications may be treated by administering anti-VEGF antibodies, such as bevacizumab, ranibizumab, or aflibercept, but the anti-VEGF antibodies, or a significant portion thereof, typically are cleared from the SCS before binding with VEGF. The binding molecule, however, may be configured to remain in the SCS for a relatively long period before being cleared. For example, a binding molecule may be a gel prior to administration to the SCS, or form a gel upon administration to the SCS. The gels provided herein may be formed by or with the aid of covalent bonds, non-covalent bonds, or a combination thereof, and the gel may degrade as the bonds are broken. The bonds, as described herein, may be broken through chemical reaction, enzymatic activity, alteration of attractive and/or repulsive interaction, or a combination thereof.

In some embodiments, the binding molecule is configured to have a clearance time from the SCS of about 1 day to about 1 day to about 90 days, about 1 day to about 60 days, about 1 day to about 30 days, about 1 day to about 21 days, about 1 day to about 14 days, about 1 day to about 7 days, about 1 day to about 3 days, about 2 days to about 90 days, about 3 days to about 90 days, about 3 days to about 60 days, about 3 days to about 30 days, about 3 days to about 21 days, about 3 days to about 14 days, or about 3 days to about 7 days. In other embodiment, the binding molecule is configured to have a clearance time from the SCS of about 1 day to about 365 days, about 3 days to about 365 days, about 3 days to about 300 days, about 3 days to about 200 days, about 3 days to about 150 days, about 3 days to about 125 days, about 7 days to about 365 days, about 7 days to about 300 days, about 7 days to about 200 days, about 7 days to about 150 days, about 7 days to about 125 days. The "clearance time from the SCS" of the binding material is the time required for substantially all of the binding molecule administered to the SCS to escape the SCS.

In some embodiments, the binding molecule has a hydrodynamic radius of at least 7 nm, at least 8 nm, at least 9 nm, at least 10 nm, at least 12 nm, at least 15 nm, at least 17 nm, at least 20 nm, at least 25 nm, at least 30 nm, at least 35 nm, at least 40 nm, at least 45 nm, at least 50 nm, at least 55 nm, at least 60 nm, at least 65 nm, at least 70 nm, at least 75 nm, at least 80 nm, at least 85 nm, at least 90 nm, at least 95 nm, or at least 100 nm. In particular embodiments, the binding molecule has a molecular weight of at least 375 kDa and a hydrodynamic radius of at least 7 nm, at least 8 nm, at least 9 nm, at least 10 nm, at least 12 nm, at least 15 nm, at least 17 nm, at least 20 nm, at least 25 nm, at least 30 nm, at least 35 nm, at least 40 nm, at least 45 nm, at least 50 nm, at least 55 nm, at least 60 nm, at least 65 nm, at least 70 nm, at least 75 nm, at least 80 nm, at least 85 nm, at least 90 nm, at least 95 nm, or at least 100 nm. In some embodiments, the binding molecule has a molecular weight of at least 400 kDa and a hydrodynamic radius of at least 7 nm, at least 8 nm, at least 9 nm, at least 10 nm, at least 12 nm, at least 15 nm, at least 17 nm, at least 20 nm, at least 25 nm, at least 30 nm, at least 35 nm, at least 40 nm, at least 45 nm, at least 50 nm, at least 55 nm, at least 60 nm, at least 65 nm, at least 70 nm, at least 75 nm, at least 80 nm, at least 85 nm, at least 90 nm, at least 95 nm, or at least 100 nm. In additional embodiments, the binding molecule has a molecular weight of at least 425 kDa and a hydrodynamic radius of at least 7 nm, at least 8 nm, at least 9 nm, at least 10 nm, at least 12 nm, at least 15 nm, at least 17 nm, at least 20 nm, at least 25 nm, at least 30 nm, at least 35 nm, at least 40 nm, at least 45 nm, at least 50 nm, at least 55 nm, at least 60 nm, at least 65 nm, at least 70 nm, at least 75 nm, at least 80 nm, at least 85 nm, at least 90 nm, at least 95 nm, or at least 100 nm. In particular embodiments, the binding molecule has a molecular weight of at least 450 kDa and a hydrodynamic radius of at least 7 nm, at least 8 nm, at least 9 nm, at least 10 nm, at least 12 nm, at least 15 nm, at least 17 nm, at least 20 nm, at least 25 nm, at least 30 nm, at least 35 nm, at least 40 nm, at least 45 nm, at least 50 nm, at least 55 nm, at least 60 nm, at least 65 nm, at least 70 nm, at least 75 nm, at least 80 nm, at least 85 nm, at least 90 nm, at least 95 nm, or at least 100 nm. In some embodiments, the binding molecule has a molecular weight of at least 475 kDa and a hydrodynamic radius of at least 7 nm, at least 8 nm, at least 9 nm, at least 10 nm, at least 12 nm, at least 15 nm, at least 17 nm, at least 20 nm, at least 25 nm, at least 30 nm, at least 35 nm, at least 40 nm, at least 45 nm, at least 50 nm, at least 55 nm, at least 60 nm, at least 65 nm, at least 70 nm, at least 75 nm, at least 80 nm, at least 85 nm, at least 90 nm, at least 95 nm, or at least 100 nm. In still further embodiments, the binding molecule has a hydrodynamic radius of at least 7 nm, and a combined molecular weight of at least 375 kDa, at least 400 kDa, at least 425 kDa, at least 450 kDa, or at least 475 kDa.

In some embodiments, the binding molecule has molecular weight of at least 500 kDa, at least 750 kDa, at least 1 MDa, at least 1.5 MDa, or at least 2 MDa.

In some embodiments, the fluid formulation includes a pharmaceutical agent and a liquid medium in which the pharmaceutical agent is dissolved. The release of the pharmaceutical agent from the formulation may be controlled by the rate at which the pharmaceutical agent partitions from the liquid medium into an ocular fluid of the SCS. The fluid formulation may include a surfactant. The pharmaceutical agent also may include at least one feature that increases its solubility in the liquid medium. In some embodiments, the liquid medium, upon administration to the SCS, forms a discontinuous phase of an emulsion, which may be stabilized by a surfactant at the interface of the liquid medium and the continuous phase surrounding it (e.g., ocular fluid).

In some embodiments, a fluid formulation changes properties upon delivery to the SCS. For example, a fluid formulation in the form of a liquid may gel or solidify within the ocular tissue. The gelation or solidifying of such a formulation upon delivery into the SCS may be mediated, for example, by the presence of water, removal of solvent, change of temperature, change of pH, application of light, presence of ions, and the like. The gelation or solidification also may be achieved by cross-linking or using other covalent and/or non-covalent molecular interactions.

In still other embodiments, a fluid formulation transforms from a solid-state associated with a microneedle to a dissolved state in the SCS. In some such embodiments, the formulation may be administered to an SCS as a solid coating on the microneedle or as part of the microneedle structure itself. In such embodiments, the formulation associated with the microneedle can include other excipients that serve various other functions. For example, the excipients may function to stabilize a drug (e.g., protect the drug from damage during the process of making the microneedles and/or storage of the microneedles and/or use of the microneedles), provide mechanical strength to the microneedle (e.g., providing sufficient strength so that the microneedle can be pressed into tissue without inappropriate deformation or damage), enhance wetting or facilitate solubilization of materials during manufacturing and use, and the like.

Methods of Administering Fluid Formulations

In some embodiments, methods are provided for administering a fluid formulation to an eye of a patient. In some embodiments, the methods include inserting a microneedle into the eye at an insertion site; and infusing a volume of a fluid formulation through the microneedle into the SCS of an eye at the insertion site, wherein the fluid formulation is selected from those described herein. As used herein, the phrases "fluid formulation" and "liquid formulation" generally refer to compositions that are infusible, especially into an eye. Although the formulations have an infusible fluid or liquid character, the formulations may include non-fluid and non-liquid materials, respectively, including, but not limited to, solid particles (e.g., micro- or nano-particles) in suspension. In some embodiments, the formulations herein are delivered to the SCS using non-surgical methods (e.g., microneedle devices and methods).

In some embodiments, the fluid formulation administered by the methods provided herein includes a pharmaceutical agent and a binding molecule. In some embodiments, the pharmaceutical agent and the binding molecule are disposed in a single liquid. In another embodiment, the pharmaceutical agent and the binding molecule are disposed in separate parts of a fluid formulation. For example, a binding molecule may be included in a first part of a fluid formation, a pharmaceutical agent may be included in a second part of a fluid formulation, and the step of infusing a volume of a fluid formulation may include infusing into the SCS a first part of the fluid formulation comprising the binding molecule; and infusing into the SCS a second part of the fluid formulation comprising the pharmaceutical agent. The infusing of the first part of the fluid formulation and the infusing of the second part of the fluid formulation may be performed in any order, and could be repeated. For example, infusing a volume of a fluid formulation may include infusing a first part of the fluid formulation, infusing a second part of the fluid formulation, infusing an additional volume of the first part of the fluid formulation, etc.

In some embodiments, the fluid formulation administered by the methods provided herein include a pharmaceutical agent and a binding molecule, and the pharmaceutical agent administered has a clearance time that is at least 2 times greater, at least 3 times greater, at least 4 times greater, at least 5 times greater, at least 6 times greater, at least 7 times greater, at least 8 times greater, at least 9 times greater, at least 10 times greater, at least 15 times greater, at least 20 times greater, at least 50 times greater, or at least 100 times greater than a comparative pharmaceutical agent administered in the absence of the binding molecule.

In some embodiments, the fluid formulation administered by the methods provided herein include a pharmaceutical agent and a binding molecule, and the pharmaceutical agent has a clearance time from the SCS of about 1 day to about 90 days, about 1 day to about 60 days, about 1 day to about 30 days, about 1 day to about 21 days, about 1 day to about 14 days, about 1 day to about 7 days, about 1 day to about 3 days, about 2 days to about 90 days, about 3 days to about 90 days, about 3 days to about 60 days, about 3 days to about 30 days, about 3 days to about 21 days, about 3 days to about 14 days, or about 3 days to about 7 days. In some embodiments, the pharmaceutical agent administered according to the methods provided herein has a clearance time from the SCS of about 1 day to about 365 days, about 3 days to about 365 days, about 3 days to about 300 days, about 3 days to about 200 days, about 3 days to about 150 days, about 3 days to about 125 days, about 7 days to about 365 days, about 7 days to about 300 days, about 7 days to about 200 days, about 7 days to about 150 days, about 7 days to about 125 days. The "clearance time" of the pharmaceutical agent is the time required for substantially all of the pharmaceutical agent to escape the SCS.

Methods of Enhancing Delivery to SCS

Methods of enhancing the delivery of a pharmaceutical agent to a SCS of an eye of a patient also are provided. In some embodiments, the methods include inserting a microneedle into the eye at an insertion site; infusing through the microneedle into the SCS a volume of a liquid formulation sufficient to reduce by at least 25% the minimum force to separate the sclera and choroid; and then disposing a pharmaceutical agent in the SCS. In some embodiments, the minimum force to separate the sclera and choroid is reduced by about 30% to about 80%, about 40% to about 80%, about 45% to about 80%, about 45% to about 70%, about 45% to about 60%, about 45% to about 55%, or about 50%.

Not wishing to be bound by any particular theory, it is believed that the minimum force to separate the sclera and the choroid may be reduced due to the stretching and/or breaking of SCS fibrils that occurs due to the infusion of the liquid formulation.

The liquid formulation may include any biocompatible liquid formulation, and may include water or an aqueous formulation including one or more salts. In some embodiments, the liquid formulation is Hank's Balanced Salt Solution HBSS. The volume of the liquid formulation may be any volume capable of reducing the minimum force to separate the sclera and choroid. In some embodiments, the volume of the liquid formulation is about 50 µL to about 300 µL, about 50 µL to about 275 µL, about 50 µL to about 250 µL, about 50 µL to about 225 µL, about 50 µL to about 200 µL, about 50 µL to about 175 µL, about 50 µL to about 150 µL, about 60 µL to about 140 µL, about 70 µL to about 130 µL, about 80 µL to about 120 µL, about 90 µL to about 110 µL, or about 100 µL.

Methods of Expanding a SCS

Provided herein are methods of expanding a SCS of an eye. As used herein, the phrase "expanding of SCS" refers to the distension of the choroid off the sclera, which increases the thickness of the SCS.

In some embodiments, the methods include inserting a microneedle into the eye at an insertion site; and then infusing through the microneedle into the SCS a liquid formulation having a viscosity sufficient to expand at least a portion of the SCS to a thickness of at least 500 or about 500 µm to about 3 mm, for at least two hours after the infusing. In some embodiments, the viscosity of the liquid formulation is sufficient to expand the SCS to a thickness of about 750 µm to about 2.8 mm, about 750 µm to about 2.5 mm, about 750 µm to about 2 mm, or about 1 mm to about 2 mm. In another embodiment, the viscosity of the liquid formulation is sufficient to expand the SCS to a thickness of about 500 µm to about 3.0 mm for at least two hours, at least three hours, at least four hours, at least five hours, at least six hours, at least seven hours, at least eight hours, at least ten hours, at least twelve hours, at least eighteen hours, at least twenty-four hours, at least two days, at least three days, at least five days, at least ten days, at least twenty-one days, at least one month, at least six weeks, at least two months, at least three months, at least 4 months, at least 5 months, at least 6 months, at least 9 months, at least one year, at least three years, or at least five years after the infusing. In some embodiments, the viscosity of the liquid formulation is sufficient to expand the SCS to a thickness of about 1 mm to about 3 mm for at least two hours, at least three hours, at least four hours, at least five hours, at least six hours, at least seven hours, at least eight hours, at least ten hours, at least twelve hours, at least eighteen hours, or at least twenty-four hours after the infusing. In a still further embodiment, the viscosity of the liquid formulation is sufficient to expand the SCS to a thickness of about 1 mm to about 2 mm for at least two hours, at least three hours, at least four hours, at least five hours, at least six hours, at least seven hours, at least eight hours, at least ten hours, at least twelve hours, at least eighteen hours, at least twenty-four hours, at least two days, at least three days, at least five days, at least ten days, at least twenty-one days, at least one month, at least six weeks, at least two months, at least three months, at least 4 months, at least 5 months, at least 6 months, at least 9 months, at least one year, at least three years, or at least five years after the infusing. In yet another embodiment, the viscosity of the liquid formulation is sufficient to expand the SCS to a thickness of about 2 mm to about 3 mm for at least two hours, at least three hours, at least four hours, at least five hours, at least six hours, at least seven hours, at least eight hours, at least ten hours, at least twelve hours, at least eighteen hours, at least twenty-four hours, at least two days, at least three days, at least five days, at least ten days, at least twenty-one days, at least one month, at least six weeks, at least two months, at least three months, at least 4 months, at least 5 months, at least 6 months, at least 9 months, at least one year, at least three years, or at least five years after the infusing. In some embodiments, the viscosity of the liquid formulation is sufficient to expand the SCS to a thickness of about 750 µm to about 2.8 mm, about 750 µm to about 2.5 mm, about 750 µm to about 2 mm, or about 1 mm to about 2 mm for an indefinite period. An indefinite period may be achieved due, at least in part, to the stability of the liquid formulation in the SCS (e.g., crosslinking and/or other mechanisms result in a swollen, and very stable, gel).

In some embodiments, the methods include inserting a microneedle into the eye at an insertion site; infusing a volume of a first liquid formulation, wherein the volume of the first liquid formulation is sufficient to reduce by at least 25% the minimum force to separate the sclera and choroid bounding the SCS; and then infusing through the microneedle into the SCS a second liquid formulation having a viscosity sufficient to expand at least a portion of the SCS to a thickness of about 500 µm to about 3 mm for at least two hours after the infusing.

Not wishing to be bound by any particular theory, it is believed SCS thickness may be controlled at least in part by balancing the viscous forces of a liquid formulation and the biomechanical forces inherent to a tissue, such as the viscoelastic properties of the sclera and/or choroid, the viscoelastic and failure mechanics of the SCS fibrils, or a combination thereof. When fluid first enters the SCS, it can expand the thickness of the SCS at the site of injection and/or it can expand the area of the SCS that it occupies. The SCS may expand to accommodate the fluid when there is less physical resistance to increasing thickness. Increasing thickness may require, at least in part, overcoming one or more biomechanical forces (e.g., from fibrils connecting sclera to choroid), elastic restoring forces of the sclera and choroid tissues, intraocular pressure, or a combination thereof. Increasing area may require overcoming the viscous forces opposing flow of fluid circumferentially in the SCS. SCS expansion, therefore, may be controlled, in some embodiments, by balancing the viscous forces of the injected liquid formulation (which increase with fluid viscosity) and the biomechanical forces that hold the sclera and choroid together (which are unaffected by fluid viscosity or fluid volume). The forces that limit expansion of SCS thickness may be, at least in part, related to fibrils that bind the sclera and choroid and that may need to stretch and/or break to accommodate SCS expansion.

The liquid formulation having a viscosity sufficient to expand the SCS to a thickness of at least 500 µm, or about 500 µm to about 3 mm, may have a viscosity greater than the viscosity of water (i.e., about 1 cP). For example, the liquid formulation may have a viscosity that is at least $1 \times 10^3$ cP, at least $3 \times 10^3$ cP, at least $1 \times 10^4$ cP, at least $3 \times 10^4$ cP, at least $1 \times 10^5$ cP, at least $1.7 \times 10^5$ cP, at least $3 \times 10^5$ cP, at least $1 \times 10^6$ cP or at least $3 \times 10^6$ cP. Because viscosity depends on shear rate, the "viscosity" of the liquid formulation is the viscosity at any point between a shear rate of $0.01$ $s^{-1}$ to $1$ $s^{-1}$.

The liquid formulation having a viscosity sufficient to expand the SCS to a thickness of at least 500 µm, or about 500 µm to about 3 mm, generally may include water and a polysaccharide. In some embodiments, the liquid formulation includes water and a polysaccharide at a concentration of about 1% to about 50% by weight, based on the weight of the liquid formulation. In another embodiment, the liquid formulation includes water and a polysaccharide at a concentration of about 1% to about 40% by weight, based on the weight of the liquid formulation. In some embodiments, the liquid formulation includes water and a polysaccharide at a concentration of about 1% to about 30% by weight, based on the weight of the liquid formulation. In an additional embodiment, the liquid formulation includes water and a polysaccharide at a concentration of about 1% to about 20% by weight, based on the weight of the liquid formulation. In yet another embodiment, the liquid formulation includes water and a polysaccharide at a concentration of about 1% to about 10% by weight, based on the weight of the liquid formulation. In still another embodiment, the liquid formulation includes water and a polysaccharide at a concentration of about 1% to about 5% by weight, based on the weight of the liquid formulation. The polysaccharide generally may be selected from any biocompatible polysaccharide, such as carboxymethylcellulose, dextran, hyaluronic acid, chondroitin sulfate, or a combination thereof. A liquid formulation that exhibits non-Newtonian behavior may be desirable, as the viscosity is lower under high shear during infusion through a needle. The liquid formulation may be configured to solidify or form a crosslinked gel in the SCS. The crosslinking of the gel may include the formation of covalent and/or non-covalent bonds. If the liquid formulation solidifies or gels in the SCS, then the expansion of the SCS may be maintained for periods exceeding 24 hours. The liquid formulation also may include an additive at a concentration sufficient to draw a portion of one or more ocular fluids into the SCS. The drawing of one or more ocular fluids into the SCS may assist the expansion of the SCS. In particular embodiments, the one or more additives include a polysaccharide.

In some embodiments, the methods also include disposing a pharmaceutical agent and/or device in the expanded SCS. The pharmaceutical agent, as described herein, may include a drug. The device may include any apparatus or equipment useful in the SCS. For example, the device may include glaucoma drainage devices, suprachoroidal retinal prostheses, or a combination thereof. The expansion of the SCS may assist or permit the delivery of a pharmaceutical agent to a desired site in the SCS. It is believed that increasing liquid formulation viscosity may have a dual effect of expanding the SCS and localizing the circumferential spread at the site of injection, which may be useful in treating localized diseases. For example, anti-glaucoma agents may be placed in the anterior SCS near their site of action in the ciliary body, or anti-cancer agents may be localized in the SCS adjacent to intraocular tumors.

The methods of expanding an SCS provided herein also may be used to (i) change the geometry of ocular tissue, which can be used to alter refractive properties of the eye and/or otherwise alter the eye's interaction with light geometrically, (ii) treat myopia, for example, by shifting the position of the retina, (iii) treat presbyopia, for example, by shifting the position of the ciliary muscles, especially when the anterior portion of the SCS is expanded, (iv) re-appose the retina and choroid, (v) de-bulk tumors, for example, by expanding the SCS to isolate a tumor from its blood supply, (vi) treat retinopathy of prematurity (ROP), for example, by infusing a sufficient amount of a liquid in the peripheral SCS to promote an anti-angiogenic effect on an underdeveloped retinal/choroidal tissue, or (vii) a combination thereof.

Binding Molecule

The binding molecule of the fluid formulations provided herein generally may include any biocompatible molecule. In some embodiments, the binding molecule is a polymer. Non-limiting examples of polymers from which the binding molecule may be selected include carboxymethylcellulose, dextran, hyaluronic acid, polyethylene glycol, chondroitin sulfate, or a combination thereof. The polymer from which the binding molecule is selected may be configured to crosslink in the SCS. The crosslinking may be achieved by the formation of covalent bonds, non-covalent bonds, or a combination thereof. The polymer from which the binding molecule is selected may be configured to form a gel in the SCS.

In some embodiments, the binding molecule has a non-particulate structure. The phrase "non-particulate structure" refers to a material that is not in the form of discrete, solid particles.

In some embodiments, the binding molecule is in the form of a gel. The binding molecule may be in the form of a gel prior to infusion into the SCS, after infusion into the SCS, or a combination thereof. In some embodiments, the binding molecule is bonded to a pharmaceutical agent covalently, non-covalently, or a combination thereof, and the binding molecule and the pharmaceutical agent are components of a gel.

In some embodiments, the binding molecule is configured to precipitate in the SCS. The precipitation may occur immediately upon infusion into the SCS, or at a desired time after infusion into the SCS.

In some embodiments, the binding molecule is configured to bond to an ocular tissue covalently, non-covalently, or a combination thereof. The binding molecule may include at least one feature configured to bond to an ocular tissue covalently, non-covalently, or a combination thereof, and the at least one feature may include a hydrophobic moiety, a charged moiety, a $pK_a$ effective to bond the binding molecule to the ocular tissue, or a combination thereof. The hydrophobic moiety, the charged moiety, the $pK_a$ effective to bond the binding molecule to the ocular tissue, or a combination thereof may be selected from those that described herein.

Pharmaceutical Agent

The pharmaceutical agent of the fluid formulations and methods provided herein may refer to a suitable prophylactic, therapeutic, or diagnostic agent, i.e., an ingredient useful for medical applications. The pharmaceutical agent may include a drug. The drug may be an active pharmaceutical ingredient. For example, the drug may be selected from small molecules or suitable proteins, peptides and fragments thereof, which can be naturally occurring, synthesized or recombinantly produced, including antibodies and antibody fragments (e.g., a Fab, Fv or Fc fragment). For example, the drug may be a small molecule drug, an endogenous protein or fragment thereof, or an endogenous peptide or fragment thereof. The drug may be selected from suitable oligonucleotides (e.g., antisense oligonucleotide agents), polynucleotides (e.g., therapeutic DNA), ribozymes, dsRNAs, siRNA, RNAi, gene therapy vectors, and/or vaccines for therapeutic use. The drug may be an aptamer (e.g., an oligonucleotide or peptide molecule that binds to a specific target molecule).

In some embodiments, the pharmaceutical agent includes a monoclonal antibody.

Representative examples of types of drugs for delivery to ocular tissues include antibiotics, antiviral agents, analgesics, anesthetics, antihistamines, anti-inflammatory agents, immunosuppressives, T-cell inhibitors, alkylating agents, biologics, and antineoplastic agents. Non-limiting examples of specific drugs and classes of drugs include β-adrenoceptor antagonists (e.g., carteolol, cetamolol, betaxolol, levobunolol, metipranolol, timolol), miotics (e.g., pilocarpine, carbachol, physostigmine), sympathomimetics (e.g., adrenaline, dipivefrine), calcium channel blockers, antimetabolites (e.g., carboplatin, episodium, vinblastine), carbonic anhydrase inhibitors (e.g., acetazolamide, dorzolamide), prostaglandins, anti-microbial compounds, including anti-bacterials and anti-fungals (e.g., chloramphenicol, chlortetracycline, ciprofloxacin, framycetin, fusidic acid, gentamicin, neomycin, norfloxacin, ofloxacin, polymyxin, propamidine, tetracycline, tobramycin, quinolines), anti-viral compounds (e.g., acyclovir, cidofovir, idoxuridine, interferons), aldose reductase inhibitors, anti-inflammatory and/or anti-allergy compounds (e.g., steroidal compounds such as triamcinolone, betamethasone, clobetasone, dexamethasone, fluorometholone, hydrocortisone, prednisolone and non-steroidal compounds such as antazoline, bromfenac, diclofenac, indomethacin, lodoxamide, saprofen, sodium cromoglycate), artificial tear/dry eye therapies, local anesthetics (e.g., amethocaine, lignocaine, oxbuprocaine, proxymetacaine), cyclosporine, diclofenac, urogastrone and growth factors such as epidermal growth factor, mydriatics and cycloplegics, mitomycin C, and collagenase inhibitors and treatments of age-related macular degeneration such as pegaptanib sodium, ranibizumab, bevacizumab, and afilbercept.

In certain some embodiments, the drug is an anti-glaucoma agent, such as prostaglandins including the active ingredients in Xalatan (Pfizer), Lumigan (Allergan), Travatan Z (Alcon) and Rescula (Novartis); beta-blockers, including the active ingredients in Timoptic XE (Merck), Istalol (ISTA) and Betoptic S (Alcon); alpha-adrenergic agonists, including the active ingredients in Iopidine (Alcon), Alphagan (Allergan), and Alphagan-P (Allergan); carbonic anhydrase inhibitors, including the active ingredients in Trusopt (Merck), Azopt (Alcon), Diamox (Sigma), Neptazane (Wyeth-Ayerst) and Daranide (Merck, Sharp, & Dohme), parasympathomimetics, including pilocarpine, carbachol, echothiophate and demecarium; epinephrine, including epinephrine and dipivalyl epinephrine; and the active ingredients in marijuana.

In certain some embodiments, the drug is an integrin antagonist, a selectin antagonist, an adhesion molecule antagonist (e.g., Intercellular Adhesion Molecule (ICAM)-1, ICAM-2, ICAM-3, Platelet Endothelial Adhesion Molecule (PCAM), Vascular Cell Adhesion Molecule (VCAM), or lymphocyte function-associated antigen 1 (LFA-1)), a basic fibroblast growth factor antagonist, or a leukocyte adhesion-inducing cytokine or growth factor antagonist (e.g., Tumor Neucrosis Factor-α (TNF-α), Interleukin-1β (IL-1β), Monocyte Chemotactic Protein-1 (MCP-1), Platelet-Derived Growth Factor (PDGF), and a Vascular Endothelial Growth Factor (VEGF)). For example, in some embodiments the drug is an integrin antagonist that is a small molecule integrain antagonist, such as that described by Paolillo et al. (*Mini Rev Med Chem*, 2009, vol. 12, pp. 1439-46) or a vascular endothelial growth factor, as described in U.S. Pat. No. 6,524,581. In certain other embodiments, the drug is sub-immunoglobulin antigen-binding molecules, such as Fv immunoglobulin fragments, minibodies, and the like, as described in U.S. Pat. No. 6,773,916 to Thiel, et al. In some embodiments, the drug is a humanized antibody or a fragment thereof. In another embodiment, the drug is a diagnostic agent, such as a contrast agent.

In some embodiments, the fluid formulations provided herein further include an agent effective to degrade collagen or glycosaminoglycan (i.e., GAG) fibers in the sclera, which may enhance penetration/release of the drug into the ocular tissues. This agent may be, for example, an enzyme, such a hyaluronidase, a collagenase, or a combination thereof. In a variation of this method, the enzyme is administered to the ocular tissue in a separate step from—preceding or following—infusion of a pharmaceutical agent. The enzyme and drug are administered at the same site.

The pharmaceutical agents and methods provided herein may be used to treat a wide range of ocular disorders and maladies in patients, including both adult and child human patients. Non-human patients also may be treated. Non-limiting examples of posterior ocular disorders amenable for treatment by the formulations and methods described herein include uveitis, glaucoma, macular edema, diabetic macular edema, retinopathy, age-related macular degeneration (for example, wet AMD or dry AMD), scleritis, optic nerve degeneration, geographic atrophy, choroidal disease, ocular sarcoidosis, optic neuritis, choroidal neovascularization, ocular cancer, genetic disease(s), autoimmune diseases affecting the posterior segment of the eye, retinitis (e.g., cytomegalovirus retinitis) and corneal ulcers. Such disorders may be acute or chronic. For example, the ocular disease may be acute or chronic uveitis. Acute uveitis occurs suddenly and may last for up to about six weeks, whereas with chronic uveitis the onset of signs and/or symptoms is gradual and the symptoms last longer than about six weeks. The ocular disorders may be caused by an infection from viruses, fungi, or parasites; the presence of noninfectious foreign substances in the eye; autoimmune diseases; or surgical or traumatic injury. Particular disorders caused by pathogenic organisms that can lead to uveitis or other types of ocular inflammation include, but are not limited to, toxoplasmosis, toxocariasis, histoplasmosis, herpes simplex or herpes zoster infection, tuberculosis, syphilis, sarcoidosis, Vogt-Koyanagi-Harada syndrome, Behcet's disease, idiopathic retinal vasculitis, Vogt-Koyanagi-Harada Syndrome, acute posterior multifocal placoid pigment epitheliopathy (APMPPE), presumed ocular histoplasmosis syndrome (POHS), birdsliot chroiclopathy, Multiple Sclerosis, sympathetic opthalmia, punctate inner choroidopathy, pars planitis, or iridocyclitis.

A variety of choroidal maladies are amenable for treatment by the formulations and methods described herein, including but not limited to, choroidal neovascularization, choroidal sclerosis, polypoidal choroidal vasculopathy, central sirrus choroidopathy, a multifocal choroidopathy or a choroidal dystrophy. The choroidal dystrophy, for example, is central gyrate choroidal dystrophy, serpiginous choroidal dystrophy or total central choroidal atrophy. In some embodiments, a patient in need of treatment of a choroidal malady experiences subretinal exudation and bleeding, and the methods provided herein lessen the subretinal exudation and/or bleeding, compared to the subretinal exudation and/or bleeding experienced by the patient prior to administration of a pharmaceutical agent. In another embodiment, a patient in need of treatment experiences subretinal exudation and bleeding, and the subretinal exudation and bleeding experienced by the patient, after undergoing one of the non-surgical treatment methods provided herein, is less than the subretinal exudation and bleeding experienced by the patient after intravitreal therapy with the same drug at the same dose.

In an exemplary embodiment, the methods provide for administration of a pharmaceutical agent comprising an effective amount of an angiogenesis inhibitor to the SCS of an eye of a patient in need thereof. In some embodiments, the angiogenesis inhibitor may be interferon gamma 1β, interferon gamma 1β (Actimmune®) with pirfenidone, ACUHTR028, αVβ5, aminobenzoate potassium, amyloid P, ANG1122, ANG1170, ANG3062, ANG3281, ANG3298, ANG4011, anti-CTGF RNAi, Aplidin, *Astragalus membranaceus* extract with salvia and *Schisandra chinensis*, atherosclerotic plaque blocker, Azol, AZX100, BB3, connective tissue growth factor antibody, CT140, danazol, Esbriet, EXC001, EXC002, EXC003, EXC004, EXC005, F647, FG3019, Fibrocorin, Follistatin, FT011, a galectin-3 inhibitor, GKT137831, GMCT0I, GMCT02, GRMD01, GRMD02, GRN510, Heberon Alfa R, interferon-2β, ITMN520, JKB119, JKB121, JKB122, KRX168, LPA1 receptor antagonist, MGN4220, MIA2, microRNA 29a oligonucleotide, MMI0100, noscapine, PBI4050, PBI4419, PDGFR inhibitor, PF-06473871, PGN0052, Pirespa, Pirfenex, pirfenidone, plitidepsin, PRM151, Px102, PYN17, PYN22 with PYN17, Relivergen, rhPTX2 fusion protein, RXI109, secretin, STX100, TGF-β inhibitor, transforming growth factor, β-receptor 2 oligonucleotide, VA999260, or XV615.

Specific endogenous angiogenesis inhibitors may include endostatin, a 20 kDa C-terminal fragment derived from type XVIII collagen, angiostatin (a 38 kDa fragment of plasmin), or a member of the thrombospondin (TSP) family of proteins. In some embodiments, the angiogenesis inhibitor is a TSP-1, TSP-2, TSP-3, TSP-4 and TSP-5. Other endogenous angiogenesis inhibitors may include a soluble VEGF receptor, e.g., soluble VEGFR-1 and neuropilin 1 (NPR1), angiopoietin-1, angiopoietin-2, vasostatin, calreticulin, platelet factor-4, a tissue inhibitor of metalloproteinase (TIMP) (e.g., TIMP 1, TIMP2, TIMP3, TIMP4), cartilage-derived angiogenesis inhibitor (e.g., peptide troponin I and chrondomodulin I), a disintegrin and metalloproteinase with thrombospondin motif 1, an interferon (IFN) (e.g., IFN-α, IFN-β, IFN-γ), a chemokine, (e.g., a chemokine having the C-X-C motif (e.g., CXCL10, also known as interferon gamma-induced protein 10 or small inducible cytokine B10)), an interleukin cytokine (e.g., IL-4, IL-12, IL-18), prothrombin, antithrombin III fragment, prolactin, the protein encoded by the TNFSFJ5 gene, osteopontin, maspin, canstatin, or proliferin-related protein.

In some embodiments, the angiogenesis inhibitor delivered via the methods described herein to treat a choroidal malady is an antibody. In some embodiments, the antibody is a humanized monoclonal antibody. In some embodiments, the humanized monoclonal antibody is bevacizumab.

In some embodiments, the formulations and methods provided herein are used to treat a choroidal malady. For example, the pharmaceutical agent may be a nucleic acid administered to inhibit gene expression for treatment of the choroidal malady. The nucleic acid, in some embodiments, is a micro-ribonucleic acid (microRNA), a small interfering RNA (siRNA), a small hairpin RNA (shRNA), or a double stranded RNA (dsRNA), that targets a gene involved in angiogenesis. Thus, in some embodiments, the method to treat a choroidal malady includes administering an RNA molecule to the SCS of a patient in need thereof. The RNA molecule may be delivered to the SCS via one of the microneedles described herein. For example, in some embodiments, the patient is being treated for PCV, and the RNA molecule targets HTRA1, CFH, elastin or ARMS2, such that the expression of the targeted gene is downregulated in the patient, upon administration of the RNA. In some embodiments, the targeted gene is CFH, and the RNA molecule targets a polymorphism selected from rs3753394, rs800292, rs3753394, rs6680396, rs1410996, rs2284664, rs1329428, and rs1065489. In another embodiment, the patient is being treated for a choroidal dystrophy, and the RNA molecule targets the PRPH2 gene. In some embodiments, the RNA molecule targets a mutation in the PRPH2 gene.

In some embodiments, the VEGF antagonist delivered via the methods described herein is an antagonist of a VEGF receptor (VEGFR), i.e., a drug that inhibits, reduces, or modulates the signaling and/or activity of a VEGFR. The VEGFR may be a membrane-bound or soluble VEGFR. In some embodiments, the VEGFR is VEGFR-1, VEGFR-2 or VEGFR-3. In some embodiments, the VEGF antagonist targets the VEGF-C protein. In some embodiments, the VEGF modulator is an antagonist of a tyrosine kinase or a tyrosine kinase receptor. In some embodiments, the VEGF modulator is a modulator of the VEGF-A protein. In some embodiments, the VEGF antagonist is a monoclonal antibody. In some embodiments, the monoclonal antibody is a humanized monoclonal antibody.

In some embodiments, the pharmaceutical agent delivered to the SCS of an eye of a patient in need thereof via the methods described herein includes an effective amount of vascular permeability inhibitor. In some embodiments, the vascular permeability inhibitor is a vascular endothelial growth factor (VEGF) antagonist or an angiotensin converting enzyme (ACE) inhibitor. In some embodiments, the vascular permeability inhibitor is an angiotensin converting enzyme (ACE) inhibitor and the ACE inhibitor is captopril.

In some embodiments, the pharmaceutical agent delivered to the SCS of an eye of a patient in need thereof via the methods described herein includes a steroidal compound, which may include hydrocortisone, hydrocortisone-17-butyrate, hydrocortisone-17-aceponate, hydrocortisone-17-buteprate, cortisone, tixocortol pivalate, prednisolone, methylprednisolone, prednisone, triamcinolone, triamcinolone acetonide, mometasone, amcinonide, budesonide, desonide, fluocinonide, halcinonide, bethamethasone, bethamethasone dipropionate, dexamethasone, fluocortolone, hydrocortisone-17-valerate, halometasone, alclometasone dipropionate, prednicarbate, clobetasone-17-butyrate, clobetasol-17-propionate, fluocortolone caproate, fluocortolone pivalate, fluprednidene acetate or prednicarbate.

In some embodiments, the pharmaceutical agent delivered is a specific class of NSAID, non-limiting examples of which include salicylates, propionic acid derivatives, acetic acid derivatives, enolic acid derivatives, fenamic acid derivatives and cyclooxygenase-2 (COX-2) inhibitors. In some embodiments, one or more of the following NSAIDs are provided in the formulations: acetylsalicylic acid, diflunisal, salsalate, ibuprofen, dexibuprofen, naproxen, fenoprofen, keotoprofen, dexketoprofen, flurbiprofen, oxaprozin, loxaprofen, indomethacin, tolmetin, sulindac, etodolac, ketorolac, diclofenac or nabumetone, piroxicam, meloxicam, tenoxicam, droxicam, lornoxicara or isoxicam, mefanamic acid, meclofenamic acid, flufenamic acid, tolfenamic acid, celecoxib, refecoxib, valdecoxib, parecoxib, lumiracoxib, etoricoxib, or firocoxib.

Other examples of anti-inflammatory drugs, that can be used to treat a posterior ocular disorder or a choroidal malady, choroidal neovascularization, or subretinal exudation, include, but are not limited to: mycophenoiate, remicase, nepafenac, 19AV agonist(s), 19GJ agonists, 2MD analogs, 4SC101, 4SC102, 57-57, 5-HT2 receptor antagonist, 64G12, A804598, A967079, AAD2004, AB1010, AB224050, abatacept, etaracizumab (Abegrin™) Abevac®, AbGn134, AbGn168, Abki, ABN912, ABR215062, ABR224050, cyclosporine (Abrammune®), docosanol (behenyl alcohol, Abreva®), ABS15, ABS4, ABS6, ABT122, ABT325, ABT494, ABT874, ABT963, ABXIL8, ABXRB2, AC430, Accenetra, lysozyme chloride (Acdeam®), ACE772, aceclofenac (Aceblock, Acebid, Acenac), acetaminophen, chlorzoxazone, serrapeptase, tizanidine hydrochloride, betadex, Aceclogesic Plus, Aceclon, Acecloren, Aceclorism, acecrona, Aceffein, acemetacin, asprin (Acenterine), Acetal-SP (Aceclofenac-combination), Acetyl-G, acetylsalicylate dl-lysine, acetylsalicylic acid, Acicot, Acifine, Acik, Aclocen, Acloflam-P, Aclomore, Aclon, A-CQ, ACS15, actarit, Actemra, Acthelea liofilizado, Actifast, Actimab-B, Actiquim, Actirin, Actis PLUS, activated leukocyte cell adhesion molecule antibody, Acular X, AD452, adalimumab, ADAMTSS inhibitor, ADC1001, Adco-Diclofenac, Adco-Indomethacin, Adco-Meloxicam, Adco-Naproxen, Adco-Piroxicam, Adcort, Adco-Sulindac, adenosine triphosphate disodium, AdenosineA2a Receptor Agonist, Adimod, Adinos, Adioct, Adiodol, Adipoplus, adipose derived stem and/or regenerative cells, Adizen, Adpep, Advacan, Advagraf, Advel, Adwiflam, AEB071, Aental, Afenac, Affen Plus, Afiancen, Afinitor, Aflamin, Aflazacort, Aflogen, Afloxan, AFM15, AFM16, AFM17, AFM23, Afpred-Dexa, AFX200, AG011, Agafen, aganirsen, AGI1096, Agidex, AGS010, Agudol, A-Hydrocort, AIK1, AIN457, Airtal, AIT110, AJM300, ajulemic acid, AK106, AL-24-2A1, AL4-1A1, Ala Cort, Alanz, Albumin immune-globulin, alclometasone dipropionate, ALD518, aldesleukin, Aldoderma, alefacept, alemtuzmab, Alequel™, Alergolon, Alergosone, Aletraxon, Alfenac, Algason, Algin vek coat, Algioflex, Algirex, Aigivin Plus, alicaforsen sodium, Alin, Alinia, Aliviodol, Aliviosin, alkaline phosphatase, ALKS6931, allantoin, Allbupen, Allmol, Allochrysine, allogeneic endothelial cells, allogeneic mesenchymal precursor cells, allogeneic mesenchymal stem cells, alminoprofen, alpha 1 antitrypsin, Alpha 7 nicotinic agonists, alpha amylase, alpha chymotrypsin, alpha fetoprotein, alpha linolenic acid, alpha-1-antitrypsin, α2β1 integrin inhibitors, Alphacort, Alphafen, alpha-hexidine, alpha-trypsin, Alphintern, Alpinamed mobility omega 3, Alpoxen, AL-Revl, Alterase, ALX0061, ALX0761, ALXN1007, ALXN1102, AM3840, AM3876, AMAB, AMAP102, Amason, Ambene, AmbezimG, amcinonide, AME133v, Amecin, Ameloteks, A-Methapred, Amevive, AMG108, AMG139, AMG162, AMG181, AMG191, AMG220, AMG623, AMG674, AMG714, AMG719, AMG729, AMG827, Amidol, amifampridine phosphate, diclofenac (Emifenac®), Amimethacin, amiprilose hydrochloride, Amiprofen, Ammophos, Amoflam, AMP 110, Ampikyy, Ampion, ampiroxicam, amtolmetin guacil, AMX256, AN6415, ANA004, ANA506, Anabu, Anacen, Anaflam, Anaflex ACI, Anaida, anakinra, Analgen Artritis, Anapan, Anaprox, Anavan, Anax, Anco, andrographis, Ancol, Anergix, Anervax.RA™ (therapeutic peptide vaccine), Anflene, ANG797, Anilixin, Anmerushin, Annexin 1 peptides, annexin A5, Anodyne, Ansaid, Anspirin, Antarene, anti BST2 antibody, anti C5a MAb, anti ILT7 antibody, anti VLA1 antibody, anti-alpha1 1 antibody, anti-CD4 802-2, anti-CD86 monoclonal antibody, anti-chemokine, anti-DC-SIGN, anti-HMGB-1 MAb, anti-IL-18 Mab, anti-IL-1R MAb, anti-IL-1R MAb, anti-IL23 BRISTOL, anti-interleukin-1β antibody, anti-LIGHT antibody, anti-MIF antibody, anti-miR181a, antioxidant inflammation modulators, Antiphlamine, AntiRAGE MAb, antithrombin III, Anti-TIRC-7 MAb, Anusol-HC, Anyfen, AP105, AP1089, AP1189, AP401, AP501, apazone, APD334, Apentac, APG103, Apidone, apilimod mesylate, Apitac, Apitoxin, Apizel, APN inhibitor, apo-azathioprine, Apo-dexamethasone, ApoE mimetics, ApoFasL, apo-Indomethacin, apo-mefenamic, apo-methotrexate, apo-nabumetone, Apo-Napro-NA, apo-Naproxen, aponidin, apo-Phenylbutazone, apo-Piroxicam, apo-Sulin, Apo-Tenoxicam, apo-Tiaprofenic, Apranax, apremilast, apricoxib, Aprofen, Aprose, Aproxen, APX001 antibody, APX007 antibody, APY0201, AqvoDex, AQX108, AQX1125, AQX131135, AQX140, AQX150, AQX200, AQX356, AQXMN100, AQXMN106, ARA290, Arava, Arcalyst, Arcoxia, Arechin, Arflur, ARG098, ARG301, arginine aescin, arginine deiminase (pegylated), ARGX109 antibody, ARGX110, Arheuma, Aristocort, Aristospan, Ark-AP, ARN4026, Arofen, Aroff EZ, Arolef, Arotal, Arpibru, Arpimune, Arpu Shuangxin, ARQ101, Arrestin SP, Arrox, ARRY162, ARRY371797, ARRY614, ARRY872, ART621, Artamin, Arthfree, Artho Tech, Arthrexin, Arthrispray, Arthrotec, aeterna shark cartilage extract (Arthrovas™, Neoretna™ Psovascar™), Artifit, Artigo, Artin, Artinor, Artisid, Artoflex, Artren Hipergel, Artridol, Artrilase, Artrocaptin, Artrodiet, Artrofen, Artropan, Artrosil, Artrosilene, Artrotin, Artrox, Artyflam, Arzerra, AS604850, AS605858, Asacol, ASA-Grindeks, Asazipam, Aseclo, ASF1096, ASK8007, ASKP1240, ASLAN003, Asmo ID, Asonep, ASP015K, ASP2408, ASP2409, Aspagin, Aspeol, Aspicam, Aspirimex, AST120, astaxanthin, Astro-Cort, Aszes, AT002 antibody, AT007, AT008 antibody, AT010, AT1001, atacicept, Ataspin, Atepadene, Atgam, ATG-Fresenius, Athrofen, ATIO03, atiprimod, ATL1222, ATN103, ATN192, ATR107, Atri, Atrmin, Atrosab antibody, ATX3105, AU801, auranofin, Aurobin, Auropan, Aurothio, aurotioprol, autologous adipose derived regenerative cells, Autonec, Avandia, AVE9897, AVE9940, Avelox, Avent, AVI3378, Avloquin, AVP13546, AVP13748, AVP28225, AVX002, Axcel Diclofenac, Axcel Papain, Axen, AZ17, AZ175, Azacortid, AZA-DR, Azafrine, Azamun, Azanin, Azap, Azapin, Azapren, Azaprin, Azaram, Azasan, azathioprine, AZD0275, AZD0902, AZD2315, AZD5672, AZD6703, AZD7140, AZD8309, AZD8566, AZD9056, Azet, Azintrel, azithromycin, Az-od, Azofit, Azolid, Azoran, Azulene, Azulfidine, Azulfin, B1 antagonists, Baclonet, BAF312, BAFF Inhibitor, Bages, Baily S.P., Baleston, Balsolone, baminercept alfa, bardoxolone methyl, baricitinib, Barotase, Basecam, basiliximab, Baxmune, Baxo, BAY869766, BB2827, BCX34, BCX4208, Becfine, Beclate-C, Beclate-N, Beclolab Q, beclomethasone dipropionate, Beclorhin, Becmet-CG, Begita, Begti, belatacept, belimumab, Belosalic, Bemetson, Ben, Benevat, Benexam, Benflogin, Benisan, Benlysta, benorilate, Benoson, benoxaprofen, Bentol, benzydamine hydrochloride, Benzymin, Beofenac, Berafen, Berinert, Berlofen, Bertanel, Bestamine, Bestofen, Beta Nicip, Betacort, Betacorten G, Betafoam, beta-glucan, Betalar, Beta-M, Betamed, Betamesol, betamethasone, betamethasone dipropionate, betamethasone sodium, betamethasone sodium phosphate, betamethasone valerate, Betane, Betanex, Betapanthen, Betapar, Betapred, Betason, Betasonate, Betasone, Betatrinta, Betaval, Betazon, Betazone, Betesil, Betnecort, Betnesol, Betnovate, Bextra, BFPC13, BFPC18, BFPC21, BFPT6864, BG12, BG9924, BI695500, BI695501, BIA12, Big-Joint-D, BIIB023 antibody, Bi-ksikam, Bingo, BioBee, Bio-Cartilage, Bio-C-Sinkki, Biodexone, Biofenac, Bioreucarn, Biosone, Biosporin, BIRB796, Bitnoval, Bitvio, Bivigam, BKT140, BKTP46, BL2030, BL3030, BL4020, BL6040, BL7060, BL11300, blisibimod, Blokium B12, Blokium Gesic, Blokium, BMS066, BMS345541, BMS470539, BMS561392, BMS566419, BMS582949, BMS587101, BMS17399, BMS936557, BMS945429, BMS-A, BN006, BN007, BNP166, Bonacort, Bonas, bone marrow stromal cell antigen 2 antibody, Bonflex, Bonifen, Boomiq, Borbit, Bosong, BR02001, BR3-FC, Bradykinin B1 Receptor Antagonist, Bredinin, Brexecam, Brexin, Brexodin, briakinumab, Brimani, briobacept, Bristaflam, Britten, Broben, brodalumab, Broen-C, bromelains, Bromelin, Bronax, Bropain, Brosiral, Bruace, Brufadol, Brufen, Brugel, Brukil, Brusil, BT061, BT19, BT kinase inhibitors, BTT1023 antibody, BTT1507, bucillamine, Bucillate, Buco Reigis, bucolome, Budenofalk, budesonide, Budex, Bufect, Bufencon, Bukwang Ketoprofen, Bunide, Bunofen, Busilvex, busulfan, Busulfex, Busulipo, Butartrol, Butarut B12, Butasona, Butazolidin, Butesone, Butidiona, BVX10, BXL628, BYM338, B-Zone, C1 esterase inhibitor, C243, c4462, c5997, CSaQb, c7198, c9101, C9709, c9787, CAB101, cadherin 11 antibody, caerulomycin A, CAL263, Calcort, Calmatel, CAM3001, Camelid Antibodies, Camlox, Camola, Campath, Camrox, Camtenam, canakinumab, *Candida albicans* antigen, Candin, cannabidiol, CAP 1.1, CAP1.2, CAP2.1, CAP2.2, CAP3.1, CAP3.2, Careram, Carimune, Cariodent, Cartifix, CartiJoint, Cartilago, Cartisafe-DN, Cartishine, Cartivit, Cartril-S, Carudol, CaspaCIDe, Casyn, CAT1004, CAT1902, CAT2200, Cataflam, Cathepsin S inhibitor, Catlep, CB0114, CB2 agonist CC0478765, CC10004, CC10015, CC1088, CC11050, CC13097, CC15965, CC16057, CC220, CC292, CC401, CC5048, CC509, CC7085, CC930, CCR1 antagonist, CCR6 inhibitor, CCR7 antagonist, CCRL2 antagonist, CCX025, CCX354, CCX634, CD Diclofenac, CD102, CD103 antibody, CD137 antibody, CD16 antibody, CD18 antibody, CD19 antibody, CD1d antibody, CD20 antibody, CD200Fc, CD209 antibody, CD24, CD3 antibody, CD30 antibody, CD32A antibody, CD32B antibody, CD4 antibody, CD40 ligand, CD44 antibody, CD64 antibody, CDC839, CDC998, CDIM4, CDIM9, CD 9-Inhibitor, CDP146, CDP323, CDP484, CDP6038, CDP870, CDX1135, CDX301, CE224535, Ceanel, Cebedex, Cebutid, Ceclonac, Ceex, CEL2000, Celact, Celbexx, Celcox, Celebiox, Celebrex, Celebrin, Celecox, celecoxib, Celedol, Celestone, Celevex, Celex, CELG4, Cell adhesion molecule antagonists, Cell-Cept, Cellmune, Celosti, Celoxib, Celprot, Celudex, cenicriviroc mesylate, cenplacel-1, CEP11004, CEP37247, CEP37248, Cephyr, Ceprofen, Certican, certolizumab pegol, Cetofenid, Cetoprofeno, cetylpyridimum chloride, CF10I, CF402, CF502, CG57008, CGEN15001, CGEN15021, CGEN 15051, CGEN15091, CGEN25017, CGEN25068, CGEN40, CGEN54, CGEN768, CGEN855, CGI1746, CGI560, CGI676, Cgtx-Peptides, CHI504, CH4051, CH4446, chaperonin 10, chemokine C-C motif ligand 2, chemokine C-C motif ligand 2 antibody, chemokine C-C motif ligand 5 antibody, chemokine C-C motif receptor 2 antibody, chemokine C-C motif receptor 4 antibody, chemokine C-X-C motif ligand 10 antibody, chemokine C-X-C motif ligand 12 aptamer, Chemotaxis Inhibitor, Chillmetacin, chitinase 3-like 1, Chlocodemin, Chloquin, chlorhexidine gluconate, chloroquine phosphate, choline magnesium trisalicylate, chondroitin sulfate, Chondroscart, CHR3620, CHR4432, CHR5154, Chrysalin, Chuanxinlian, Chymapra, Chymotase, chymotrypsin, Chytmutrip, CI202, CI302, Cicloderm-C, Cicloren, Cicporal, Cilamin, Cimzia, cinchophen, cinmetacin, cinnoxicam, Cinoderm, Cinolone-S, Cinryze, Cipcorlin, cipemastat, Cipol-N, Cipridanol, Cipzen, Citax F, Citogan, Citoken T, Civamide, CJ042794, CJ14877, c-Kit monoclonal antibody, cladribine, Clafen, Clanza, Ciaversal, clazakizumab, Clearoid, Clease, Clevegen, Clevian, Clidol, Clindac, Clinoril, Cliptol, Clobenate, Clobequad, clobetasol butyrate, clobetasol propionate, Clodol, clofarabine, Clofen, Clofenal LP, Clolar, Clonac, Clongamma, clonixin lysine, Clotasoce, Clovacort, Clovana, Cloxin, CLT001, CLT008, C-MAF Inhibitor, CMPXIO23, Cnac, CNDO201, CNI1493, CNTO136, CNT0148, CNT01959, Cobefen, CoBenCoDerm, Cobix, Cofenac, COG241, COL179, colchicine, Colchicum Dispert, Colchimax, Colcibra, Coledes A, Colesol, Coiifoam, Colirest, collagen, type V, Comcort, complement component (3b/4b) receptor 1, complement component C1s inhibitors, complement component C3, complement factor 5a receptor antibody, complement factor D antibody, Condrosulf, Condrotec, Condrothin, conestat alfa, connective tissue growth factor antibody, Coolpan, Copaxone, Copiron, Cordefla, Corhydron, Cort S, Cortan, Cortate, Cort-Dome, Cortecetine, Cortef, Corteroid, Corticap, Corticas, Cortic-DS, corticotropin, Cortiderm, Cortidex, Cortiflam, Cortinet M, Cortinil, Cortipyren B, Cortiran, Cortis, Cortisolu, cortisone acetate, Cortival, Cortone acetate, Cortopin, Cortoral, Cortril, Cortypiren, Cosamine, Cosone, cosyntropin, COT Kinase Inhibitor, Cotilam, Cotrisone, Cotson, Covox, Cox B, COX-2/5-LO Inhibitors, Coxeton, Coxflam, Coxicam, Coxitor, Coxtral, Coxypar, CP195543, CP412245, CP424174, CP461, CP629933, CP690550, CP751871, CPSI2364, C-quin, CR039, CR074, CR106, CRA102, CRAC channel inhibitor, CRACM ion channel inhibitor, Cratisone, CRB15, CRC4273, CRC4342, C-reactive protein 2-methoxyethyl phosphorothioate oligonucleotide, CreaVax-RA, CRH modulators, critic-aid, Crocam, Crohnsvax, Cromoglycic acid, cromolyn sodium, Cronocorteroid, Cronodicasone, CRTX803, CRx119, CRx139, CRx150, CS502, CS670, CS706, CSFIR Kinase inhibitors, CSL324, CSL718, CSL742, CT112, CT1501R, CT200, CT2008, CT2009, CT3, CT335, CT340, CT5357, CT637, CTP05, CTP10, CT-P13, CTP17, Cuprenil, Cuprimine, Cuprindo, Cupripen, Curaquin, Cutfen, CWF0808, CWP271, CX1020, CX1030, CX1040, CX5011, Cx611, Cx621, Cx911, CXC chemokine receptor 4 antibody, CXCL13 antibodies, CXCR3 antagonists, CXCR4 antagonist, Cyathus 1104 B, Cyclo-2, Cyclocort, cyclooxygenase-2 inhibitor, cyclophosphamide, Cyclorine, Cyclosporin A Prodrug, Cyclosporin analogue A, cyclosporine, Cyrevia, Cyrin CLARIS, CYT007TNFQb, CYT013ILlbQb, CYT015IL17Qb, CYTO2OTNFQb, CYT107, CYT387, CYT99007, cytokine inhibitors, Cytopan, Cytoreg, CZC24832, D1927, D942IC, daclizumab, danazol, Danilase, Dantes, Danzen, dapsone, Dase-D, Daypro, Daypro Alta, Dayrun, Dazen, DB295, DBTP2, D-Cort, DD1, DD3, DE096, DE098, Debio0406, Debio0512, Debio0615, Debio0618, Debio1036, Decaderm, Decadrale, Decadron, Decadronal, Decalon, Decan, Decason, Decdan, Decilone, Declophen, Decopen, Decorex, Decorten, Dedema, Dedron, Deexa, Defcort, De-flam, Deflamat, Defian, Deflanil, Deflaren, Deflaz, deflazacort, Defnac, Defnalone, Defnil, Defosalic, Defsure, Defza, Dehydrocortison, Dekort, Delagil delcasertib, delmitide, Delphicort, Deltacorsolone prednisolone (Deltacortril), Deltafluorene, Deltasolone, Deltasone, Deltastab, Deltonin, Demarin, Demisone, Denebola, denileukin diftitox, denosumab, Denzo, Depocortin, Depo-medrol, Depomethotrexate, Depopred, Deposet, Depyrin, Derinase, Dermol, Dermolar, Dermonate, Dermosone, Dersone, Desketo, desonide, desoxycorticosterone acetate, Deswon, Dexa, Dexabene, Dexacip, Dexacort, dexacortisone, Dexacotisil, dexadic, dexadrin, Dexadron, Dexafar, Dexahil, Dexalab, Dexalaf, Dexalet, Dexalgen, dexallion, dexalocal, Dexalone, Dexa-M, Dexamecortin, Dexamed, Dexamedis, dexameral, Dexameta, dexamethasone, dexamethasone acetate, dexamethasone palmitate, dexamethasone phosphate, dexamethasone sodium metasulfobenzoate, dexamethasone sodium phosphate, Dexamine, Dexapanthen, Dexa-S, Dexason, Dexatab, Dexatopic, Dexaval, Dexaven, Dexazolidin, Dexazona, Dexazone, Dexcor, Dexibu, dexibuprofen, Dexico, Dexifen, Deximune, dexketoprofen, dexketoprofen trometamol, Dexmark, Dexomet, Dexon I, Dexonalin, Dexonex, Dexony, Dexoptifen, Dexpin, Dextan-Plus, dextran sulfate, Dezacor, Dfz, diacerein, Diannexin, Diastone, Dicarol, Dicasone, Dicknol, Diclo, Diclobon, Diclobonse, Diclobonzox, Diclofast, Diclofen, diclofenac, diclofenac beta-dimethylaminoethanol, diclofenac deanol, diclofenac diethylamine, diclofenac epolamine, diclofenac potassium, diclofenac resinate, diclofenac sodium, Diclogen AGIO, Diclogen Plus, Diclokim, Diclomed, Diclo-NA, Diclonac, Dicloramin, Dicloran, Dicloreum, Diclorism, Diclotec, Diclovit, Diclowal, Diclozem, Dico P, Dicofen, Dicoliv, Dicorsone, Dicron, Dicser, Difena, Diffutab, diflunisal, dilmapimod, Dilora, dimethyl sulfone, Dinac, D-Indomethacin, Dioxaflex Protect, Dipagesic, Dipenopen, Dipexin, Dipro AS, Diprobeta, Diprobetasone, Diproklenat, Dipromet, Dipronova, Diprosone, Diprovate, Diproxen, Disarmin, Diser, Disopain, Dispain, Dispercam, Distamine, Dizox, DLT303, DLT404, DM199, DM99, DMI9523, dnaJP1, DNX02070, DNX04042, DNX2000, DNX4000, docosanol, Docz-6, Dolamide, Doclaren, Dolchis, Dolex, Dolflam, Dolfre, Dolgit, Dolmax, Dolmina, Dolo Ketazon, Dolobest, Dolobid, Doloc, Dolocam, Dolocartigen, Dolofit, Dolokind, Dolomed, Dolonac, Dolonex, Dolotren, Dolozen, Dolquine, Dom0100, Dom0400, Dom0800, Domet, Dometon, Dominadol, Dongipap, Donica, Dontisanin, doramapimod, Dorixina Relax, Dormelox, Dorzine Plus, Doxatar, Doxtran, DP NEC, DP4577, DP50, DP6221, D-Penamine, DPIV/ APN Inhibitors, DR1 Inhibitors, DR4 Inhibitors, DRA161, DRA162, Drenex, DRF4848, DRL15725, Drossadin, DSP, Duexis, Duo-Decadron, Duoflex, Duonase, DV1079, DV1179, DWJ425, DWP422, Dymol, DYN15, Dynapar, Dysmen, E5090, E6070, Easy Dayz, Ebetrexat, EBI007, ECO286, EC0565, EC0746, Ecax, *Echinacea purpurea* extract, EC-Naprosyn, Econac, Ecosprin 300, Ecridoxan, eculizumab, Edecam, efalizumab, Efcortesol, Effigel, Eflagen, Efridol, EGFR Antibody, EGS21, eIF5A1 siRNA, Ekarzin, elafin, Eldoflam, Elidel, Eliflam, Elisone, Elmes, Elmetacin, ELND001, ELND004, elocalcitol, Elocom, elsibucol, Emanzen, Emcort, Emifen, Emifenac, emorfazone, Empynase, emricasan, Emtor, Enable, Enbrel, Enceid, EncorStat, Encortolon, Encorton, Endase, Endogesic, Endoxan, Enkorten, Ensera, Entocort, Enzylan, Epanova, Eparang, Epatec, Epicotil, epidermal growth factor receptor 2 antibody, epidermal growth factor receptor antibody, Epidixone, Epidron, Epiklin, EPPA1, epratuzumab, EquiO, Erac, Erazon, ERB041, ERB196, Erdon, EryDex, *Escherichia coli* enterotoxin B subunit, Escin, E-Selectin Antagonists, Esfenac, ESN603, esonarimod, Esprofen, estetrol, Estopein, Estrogen Receptor beta agonist, etanercept, etaracizumab, ETC001, ethanol propolis extract, ETI511, etiprednol dicloacetate, Etodin, Etodine, Etodol, etodolac, Etody, etofenamate, Etol Fort, Etolac, Etopin, etoricoxib, Etorix, Etosafe, Etova, Etozox, Etura, Eucob, Eufans, eukaryotic translation initiation factor 5A oligonucleotide, Eunac, Eurocox, Eurogesic, everolimus, Evinopon, EVT401, Exaflam, EXEL9953, Exicort, Expen, Extra Feverlet, Extrapan, Extrauma, Exudase, F16, F991, Falcam, Falcol, Falzy, Farbovil, Farcomethacin, Farnerate, Farnezone, Farotrin, fas antibody, Fastflam, FasTRACK, Fastum, Fauldmetro, FcgammaRlA antibody, FE301, Febrofen, Febrofid, felbinac, Feldene, Feldex, Feloran, Felxicam, Fenac, Fenacop, Fenadol, Fenaflan, Fenarnic, Fenaren, Fenaton, Fenbid, fenbufen, Fengshi Gutong, Fenicort, Fenopine, fenoprofen calcium, Fenopron, Fenris, Fensupp, Fenxicam, fepradinol, Ferovisc, Feverlet, fezakinumab, FG3019, FHT401, FHTCT4, FID114657, figitumumab, Filexi, filgrastim, Fillase, Final, Findoxin, fingolimod hydrochloride, firategrast, Firdapse, Fisiodar, Fivasa, FK778, Flacoxto, Fladalgin, Flagon, Flamar, Flamcid, Flamfort, Flamide, Flaminase, Flamirex Gesic, Flanid, Flanzen, Flaren, Flash Act, Flavonoid Anti-inflammatory Molecule, Flebogamma DIF, Flenac, Flex, Flexafen 400, Flexi, Flexidol, Flexium, Flexon, Flexono, Flogene, Flogiatrin B12, Flogomin, Flogoral, Flogosan, Flogoter, Flo-Pred, Flosteron, Flotrip Forte, Flt3 inhibitors, fluasterone, Flucam, Flucinar, fludrocortisone acetate, flufenamate aluminum, flumethasone, Flumidon, flunixin, fluocinolone, fluocinolone acetonide, fluocinonide, fluocortolone, Fluonid, fluorometholone, Flur, flurbiprofen, Fluribec, Fluromethone, Flutal, fluticasone, fluticasone propionate, Flutizone, Fluzone, FM101 antibody, fms-related tyrosine kinase 1 antibody, Folitrax, fontolizumab, formic acid, Fortecortin, Fospeg, fostamatinib disodium, FP1069, FP13XX, FPA008, FPA031, FPT025, FR104, FR167653, Framebin, Frime, Froben, Frolix, FROUNT Inhibitors, Fubifen PAP, Fucole ibuprofen, Fulamotol, Fulpen, Fungifin, Furotalgin, fusidate sodium, FX002, FX141L, FX201, FX300, FX87L, Galectin modulators, gallium maltolate, Gamimune N, Gammagard, Gamma-I.V., GammaQuin, Gamma-Venin, Gamunex, Garzen, Gaspirin, Gattex, GBR500, GBR500 antibody, GBT009, G-CSF, GED0301, GED0414, Gefenec, Gelofen, Genepril, Gengraf, Genimune, Geniquin, Genotropin, Genz29155, Gerbin, gevokizumab, GF01564600, Gilenia, Gilenya, givinostat, GL0050, GL2045, glatiramer acetate, Globulin, Glortho Forte, Glovalox, Glovenin-I, GLPG0259, GLPG0555, GLPG0634, GLPG0778, GLPG0974, Gluco, Glucocerin, glucosamine, glucosamine hydrochloride, glucosamine sulfate, Glucotin, Gludex, Glutilage, GLY079, GLY145, Glycanic, Glycefort up, Glygesic, Glysopep, GMCSF Antibody, GMI1010, GMI1011, GMI1043, GMR321, GN4001, Goanna Salve, Goflex, gold sodium thiomalate, golimumab, GP2013, GPCR modulator, GPR15 Antagonist, GPR183 antagonist, GPR32 antagonist, GPR83 antagonist, G-protein Coupled Receptor Antagonists, Graceptor, Graftac, granulocyte colony-stimulating factor antibody, granulocyte-macrophage colony-stimulating factor antibody, Gravx, GRC4039, Grelyse, GS101, GS9973, GSC100, GSK1605786, GSK1827771, GSK2136525, GSK2941266, GSK315234, GSK681323, GT146, GT442, Gucixiaotong, Gufisera, Gupisone, gusperimus hydrochloride, GW274150, GW3333, GW406381, GW856553, GWB78, GXP04, Gynestrel, Haloart, halopredone acetate, Haloxin, HANALL, Hanall Soludacortin, Havisco, Hawon Bucillamin, HB802, HC31496, HCQ 200, HD104, HD203, HD205, HDAC inhibitor, HE2500, HE3177, HE3413, Hecoria, Hectomitacin, Hefasolon, Helen, Helenil, HemaMax, Hematom, hematopoietic stem cells, Hematrol, Hemner, Hemril, heparinoid, Heptax, HER2 Antibody, Herponil, hESC Derived Dendritic Cells, hESC Derived Hematopoietic stem cells, Hespercorbin, Hexacorton, Hexadrol, hexetidine, Hexoderm, Hexoderm Salic, HF0220, HF 1020, HFT-401, hG-CSFR ED Fc, Hiberna, high mobility group box 1 antibody, Hiloneed, Hinocam, hirudin, Hirudoid, Hison, Histamine H4 Receptor Antagonist, Hitenercept, Hizentra, HL036, HL161, HMPL001, HMPL004, HMPL011, HMPL342, HMPL692, honey bee venom, Hongqiang, Hotemin, HPH116, HTI101, HuCAL Antibody, Human adipose mesenchymal stem cells, anti-MHC class II monoclonal antibody, Human Immunoglobulin, Human Placenta Tissue Hydrolysate, HuMaxCD4, HuMax-TAC, Humetone, Humicade, Humira, Huons Betamethasone sodium phosphate, Huons dexamethasone sodium phosphate, Huons Piroxicam, Huons Talniflumate, Hurofen, Huruma, Huvap, HuZAF, HX02, Hyalogel, hyaluronate sodium, hyaluronic acid, hyaluronidase, Hyaron, Hycocin, Hycort, Hy-Cortisone, hydrocortisone, hydrocortisone acetate, hydrocortisone butyrate, hydrocortisone hemisuccinate, hydrocortisone sodium, phosphate, hydrocortisone sodium succinate, Hydrocortistab, Hydrocortone, Hydrolin, Hydroquine, Hydro-Rx, Hydrosone HIKMA, hydroxychloroquine, hydroxychloroquine sulfate, Hylase Dessau, HyMEX, Hypen, HyQ, Hysonate, HZN602, I.M.75, IAP Inhibitors, Ibalgin, Ibalgix, Ibex, ibrutinib, IBsolvMIR, Ibu, Ibucon, Ibudolor, Ibufen, Ibuflam, Ibuflex, Ibugesic, Ibu-Hepa, Ibukim, Ibumal, Ibunal, Ibupental, Ibupril, Ibuprof, ibuprofen, Ibuscent, Ibusoft, Ibusuki Penjeong, Ibususpen, Ibutard, Ibutop, Ibutrex, IC487892, ichthammol, ICRAC Blocker, IDEC131, IDECCE9.1, Ides, Idicin, Idizone, IDN6556, Idomethine, IDR1, Idyl SR, Ifen, iguratimod, IK6002, IKK-beta inhibitor, IL17 Antagonist, IL-17 Inhibitor, IL-17RC, IL18, IL1Hyl, IL1R1, IL-23 Adnectin, IL23 Inhibitor, IL23 Receptor Antagonist, IL-31 mAb, IL-6 Inhibitor, IL6Qb, Ilacox, Ilaris, ilodecakin, ILV094, 1LV095, Imaxetil, IMD0560, IMD2560, Irnesel Plus, Iminoral, Immodin, IMMUI03, IMMU106, Immucept, Immufine, Immunex Syrup, immunoglobulin, immunoglobulin G, Immunoprin, ImmunoRel, Immurin, IM08400, IMP731 antibody, Implanta, Imunocell, Imuran, Imurek, Imusafe, Imusporin, Imutrex, IN0701, Inal, INCB039110, INCB18424, INCB28050, INCB3284, INCB3344, Indexon, Indic, Indo, indo-A, Indobid, Indo-Bros, Indocaf, Indocarsil, Indocid, Indocin, Indomehotpas, Indomen, Indomet, Indometacin, indomethacin, Indomethasone, Indometin, Indomin, Indopal, Indoron, Indotroxin, INDUS830, INDUS83030, Infladase, Inflamac, Inflammasome inhibitor, Inflavis, Inflaxen, Inflectra, infliximab, Ingalipt, Inicox dp, Inmecin, Inmunoartro, Innamit, InnoD06006, IN07997, Inocin, Inoten, Inovan, Inpra, Inside Pap, Insider-P, Instacyl, Instracool, Intafenac, Intaflam, Inteban, Inteban Spansule, integrin, alpha 1 antibody, integrin, alpha 2 antibody, Intenurse, interferon alfa, interferon beta-1a, interferon gamma, interferon gamma antibody, Interking, interleukin 1 Hyl, interleukin 1 antibody, interleukin 1 receptor antibody, interleukin 1 beta antibody, interleukin 10, interleukin 10 antibody, interleukin 12, interleukin 12 antibody, interleukin 13 antibody, interleukin 15 antibody, interleukin 17 antibody, interleukin 17 receptor C, interleukin 18, interleukin 18 binding protein, interleukin 18 antibody, interleukin 2 receptor, alpha antibody, interleukin 20 antibody, Interleukin 21 mAb, interleukin 23 aptamer, interleukin 31 antibody, interleukin 34, Interleukin 6 Inhibitor, interleukin 6 antibody, interleukin 6 receptor antibody, interleukin 7, interleukin 7 receptor antibody, interleukin 8, interleukin 8 antibody, interleukin-18 antibody, Intidrol, Intradex, Intragam P, Intragesic, Intraglobin F, Intratect, Inzel, Iomab B, IOR-T3, IP75I, IPH2201, IPH2301, IPH24, IPH33, IPI145, Ipocort, IPP201007, I-Profen, Iprox, Ipson, Iputon, IRAK4 Inhibitor, Iremod, Irtonpyson, IRX3, IRX5183, ISA247, ISIS104838, ISIS2302, ISISCRPRx, Ismafron, IsoQC inhibitor, Isox, ITF2357, Iveegam EN, Ivepred, WIG-SN, IW001, Izilox, J607Y, J775Y, JAK Inhibitor, JAK3 inhibitor, JAK3 kinase inhibitor, JI3292, JI4135, Jinan Lida, JNJ10329670, JNJ18003414, JNJ26528398, JNJ27390467, JNJ28838017, JNJ31001958, JNJ38518168, JNJ39758979, JNJ40346527, JNJ7777120, JNT-Plus, Joflam, Joint, Glucosamin, Jointec, Jointstem, Joinup, JPE1375, JSM10292, JSM7717, JSM8757, JTE051, JTE052, JTE522, JTE607, Jusgo, K412, K832, Kaflam, KAHR101, KAHR102, KAI9803, Kalymin, Kam Predsol, Kameton, KANAb071, Kappaproct, KAR2581, KAR3000, KAR3166, KAR4000, KAR4139, KAR4141, KB002, KB003, KD7332, KE298, keliximab, Kemanat, Kemrox, Kenacort, Kenalog, Kenaxir, Kenketsu Venoglobulin-IH, Keplat, Ketalgipan, Keto Pine, Keto, Ketobos, Ketofan, Ketofen, Ketolgan, Ketonal, Ketoplus Kata Plasma, ketoprofen, Ketores, Ketorin, ketorolac, ketorolac tromethamine, Ketoselect, Ketotop, Ketovail, Ketricin, Ketroc, Ketum, Keyi, Keyven, KF24345, K-Fenac, K-Fenak, K-Gesic, Kifadene, Kilcort, Kildrol, KIM127, Kimotab, Kinase Inhibitor 4SC, Kinase N, Kincort, Kindorase, Kineret, Kineto, Kitadol, Kitex, Kitolac, KLK1 inhibitor, Klofen-L, Klotaren, KLS-40or, KLS-40ra, KM277, Knavon, Kodolo orabase, Kohakusanin, Koide, Koidexa, Kolbet, Konac, Kondro, Kondromin, Konshien, Kontab, Kordexa, Kosa, Kotase, KPE06001, KRP107, KRP203, KRX211, KRX252, KSB302, K-Sep, Kv 1.3 Blocker, Kv 1.3 4SC, Kv1.3 inhibitor, KVK702, Kynol, L156602, Labizone, Labohydro, Labopen, Lacoxa, Lamin, Lamit, Lanfetil, laquinimod, larazotide acetate, LAS186323, LAS187247, LAS41002, Laticort, LBEC0101, LCP3301, LCP-Siro, LCP-Tacro, LCsA, LDP392, Leap-S, Ledercort, Lederfen, Lederlon, Lederspan, Lefenine, leflunomide, Leflux, Lefno, Lefra, Leftose, Lefumide, Lefunodin, Lefva, lenalidomide, lenercept, LentiRA, LE015520, Leodase, Leukine, Leukocyte function-associated antigen-1 antagonist, leukocyte immunoglobulin-like receptor, subfamily A, member 4 antibody, Leukothera, leuprolide acetate, levalbuterol, levomenthol, LFA-1 Antagonist, LFA451, LFA703, LFA878, LG106, LG267 Inhibitors, LG688 Inhibitors, LGD5552, Li Life, LidaMantle, Lidex, lidocaine, lidocaine hydrochloride, Lignocaine hydrochloride, LIM0723, LIM5310, Limethason, Limus, Limustin, Lindac, Linfonex, Linola acute, Lipcy, lisofylline, Listran, Liver X Receptor modulator, Lizak, LJP1207, LJP920, Lobafen, Lobu, Locafluo, Localyn, Locaseptil-Neo, Locpren, Lodine, Lodotra, Lofedic, Loflani, Lofnac, Lolcam, Lonac, lonazolac calcium, Loprofen, Loracort, Lorcam, Lorfenamin, Lorinden Lotio, Lorncrat, lornoxicam, Lorox, losmapimod, loteprednol etabonate, Loteprednol, Lotirac, Low Molecular Ganoderma Lucidum Polysaccharide, Loxafen, Loxfenine, Loxicam, Loxofen, Loxonal, Loxonin, loxoprofen sodium, Loxoron, LP183A1, LP183A2, LP204A1, LPCN1019, LT1942, LT1964, LTNS101, LTNS103, LTNS106, LTNS108, LTS1115, LTZMP001, Lubor, lumiracoxib, Lumitect, LX2311, LX2931, LX2932, LY2127399, LY2189102, LY2439821, LY294002, LY3009104, LY309887, LY333013, lymphocyte activation gene 3 antibody, Lymphoglobuline, Lyser, lysine aspirin, Lysobact, Lysoflam, Lysozvme hydrochloride, M3000, M834, M923, mAb hG-CSF, MABP1, macrophage migration inhibitory factor antibody, Maitongna, Majamil prolongatum, major histocompatibility complex class II DR antibody, major histocompatibility complex class II antibody, Malidens, Malival, mannan-binding lectin, mannan-binding lectin-associated serine protease-2 antibody, MapKap Kinase 2 Inhibitor, maraviroc, Marlex, masitinib, Maso, MASP2 antibody, MAT304, Matrix Metalloprotease Inhibitor, mavrilimumab, Maxiflam, Maxilase, Maximus, Maxisona, Maxius, Maxpro, Maxrel, Maxsulid, Maxyl 2, Maxy30, MAXY4, Maxy735, Maxy740, Mayfenamic, MB11040, MBPY003b, MCAF5352A, McCam, McRofy, MCS18, MD707, MDAM, MDcort, MDR06155, MDT012, Mebicam, Mebuton, meclofenamate sodium, Meclophen, Mecox, Medacomb, Medafen, Medamol, Medesone, MEDI2070, MEDI5117, MEDI541, MED1552, MEDI571, Medicox, Modifen, Medisolu, Medixon, Mednisol, Medrol, Medrolon, medroxyprogesterone acetate, Mefalgin, mefenamic acid, Mefenix, Mefentan, Meflen, Mefnetra forte, Meftagesic-DT, Meftal, Megakaryocyte Growth and Development Factor, Megaspas, Megaster, megestrol acetate, Meite, Meksun, Melbrex, Melcam, Melflam, Melic, Melica, Melix, Melocam, Melocox, Mel-One, Meloprol, Melosteral, Melox, Meloxan, Meloxcam, Meloxic, Meloxicam, Meloxifen, Meloxin, Meloxiv, Melpred, Melpros, Melurjin, Menamin, Menisone, Menthomketo, Menthoneurin, Mentocin, Mepa, Mepharen, meprednisone, Mepresso, Mepsolone, mercaptopurine, Mervan, Mesadoron, mesalamine, Mesasal, Mesatec, Mesenchymal Precursor Cells, mesenchymal stem cell, Mesipol, Mesren, Mesulan, Mesulid, Metacin, Metadaxan, Metaflex, Metalcaptase, metalloenzyme inhibitors, Metapred, Metax, Metaz, Meted, Metedic, Methacin, Methaderm, Methasone, Methotrax, methotrexate, methotrexate sodium, Methpred, Methyl prednisolone acetate, methyl salicylate, methyl sulphonyl methane, Methylon, Methylpred, methylprednisolone, methylprednisolone acetate, methylprednisolone sodium succinate, methylprednisolone succinate, Methysoi, Metindol, Metoart, Metojеct, Metolate, Metoral, Metosyn, Metotab, Metracin, Metrex, metronidazole, Metypred, Mevamox, Mevedal, Mevilox, Mevin SR, Mexilal, Mexpharm, Mext, Mextran, MF280, M-FasL, MHC class II beta chain peptide, Micar, Miclofen, Miclofenac, Micofenolato Mofetil, Micosone, Microdase, microRNA 181a-2 oligonucleotide, MIF Inhibitors, MIFQb, MIKA-Ketoprofen, Mikametan, milodistim, Miltax, Minafen, Minalfen, Minalfene, Minesulin, Minocort, Mioflex, Miolox, Miprofen, Miridacin, Mirloks, Misoclo, Misofenac, MISTB03, M1STB04, Mitilor, mizoribine, MK0359, MK0812, MK0873, MK2 Inhibitors, MK50, MK8457, MK8808, MKC204, MLN0002, MLN0415, MLN1202, MLN273, MLN3126, MLN3701, MLN3897, MLNM002, MM093, MM7XX, MN8001, Mobic, Mobicam, Mobicox, Mobifen Plus, Mobilat, Mobitil, Mocox, Modigraf, Modrasone, Modulin, Mofecept, Mofetyl, mofezolac sodium, Mofilet, Molace, molgramostim, Molslide, Momekin, Momen Gele, Moment 500, Momesone, Momesun, Mometamed, mometasone, mometasone furoate, Monimate, monosodium alpha-luminol, Mopik, MOR103, MOR104, MOR105, MOR208 antibody, MORAb022, Moricam, momiflumate, Mosuolit, Motoral, Movaxin, Mover, Movex, Movix, Movoxicarn, Mox Forte, Moxen, moxifloxacin hydrochloride, Mozobil, MP, MP0210, MP0270, MP1000, MP 1031, MP196, MP435, MPA, mPGES-1 inhibitor, MPSS, MRX7EAT, MSL, MT203, MT204, mTOR Inhibitor, MTRX1011A, Mucolase, Multicort, MultiStem, muramidase, muramidase hydrochloride, muromonab-CD3, Muslax, Muspinil, Mutaze, Muvera, MX68, Mycept, Mycocell, Mycocept, Mycofenolatmofetil Actavis, Mycofet, Mycofit, Mycolate, Mycoldosa, Mycomun, Myconol, mycophenolate mofetil, mycophenolate sodium, mycophenolic acid, Mycotil, myeloid progenitor cells, Myfenax, Myfetil, Myfortic, Mygraft, Myochrysine, Myocrisin, Myprodol, Mysone, nab-Cyclosporine, Nabentac, nabiximols, Nabton, Nabuco, Nabucox, Nabuflam, Nabumet, nabumetone, Nabuton, Nac Plus, Nacta, Nacton, Nadium, Naklofen SR, NAL1207, NAL1216, NAL1219, NAL1268, NAL8202, Nalfon, Nalgesin S, namilumab, Namsafe, nandrolone, Nanocort, Nanogam, Nanosomal Tacrolimus, Napageln, Napilac, Naprelan, Napro, Naprodil, Napronax, Napropal, Naproson, Naprosyn, Naproval, Naprox, naproxen, naproxen sodium, Naproxin, Naprozen, Narbon, Narexsin, Naril, Nasida, natalizumab, Naxdom, Naxen, Naxin, Nazovel, NC2300, ND07, NDC01352, Nebumetone, NecLipGCSF, Necsulide, Necsunim, Nelsid-S, Neo Clobenate, Neo Swiflox FC, Neocoflan, Neo-Drol, Neo-Eblimon, Neo-Hydro, Neoplanta, Neoporine, Neopreol, Neoprox, Neoral, Neotrexate, Neozen, Nepra, Nestacort, Neumega, Neupogen, Neuprex, Neurofenac, Neurogesic, Neurolab, Neuroteradol, Neuroxicam, Neutalin, neutrazumab, Neuzym, New Panazox, Newfenstop, NewGam, Newmafen, Newmatal, Newsicam, NEX1285, sFcRIM, Nextomab, NF-kappaB Inhibitor, NGD20001, NHP554B, NHP554P, NI0101 antibody, NI0401, NI0501 antibody, NI0701, NI071, NI1201 antibody, NI1401, Nicip, Niconas, Nicool, NiCord, Nicox, Niflumate, Nigaz, Nikam, Nilitis, Nimace, Nimaid, Nimark-P, Nimaz, Nimcet Juicy, Nime, Nimed, Nimepast, nimesulide, Nimesulix, Nimesulon, Nimica Plus, Nimkul, Nimlin, Nimnat, Nimodol, Nimpidase, Nimsaid-S, Nimser, Nimsy-SP, Nimupep, Nimusol, Nimutal, Nimuwin, Nimvon-S, Nincort, Niofen, Nipan, Nipent, Nise, Nisolone, Nisopred, Nisoprex, Nisulid, nitazoxanide, Nitcon, nitric oxide, Nizhvisal B, Nizon, NL, NMR1947, NN8209, NN8210, NN8226, NN8555, NN8765, NN8828, NNV014100000100, NNCO51869, Noak, Nodevex, Nodia, Nofenac, Noflagma, Noflam, Noflamen, Noflux, Non-antibacterial Tetracyclines, Nonpiron, Nopain, Normferon, Notpel, Notritis, Novacort, Novagent, Novarin, Novigesic, NOXA12, NOXD19, Noxen, Noxon, NPI1302a-3, NP1342, NPI1387, NPI1390, NPRCS1, NPRCS2, NPRCS3, NPRCS4, NPRCSS, NPRCS6, NPS3, NPS4, nPT-ery, NU3450, nuclear factor NF-kappa-B p65 subunit oligonucleotide, Nucort, Nulojix, Numed-Plus, Nurokind Ortho, Nusone-H, Nutrikemia, Nuvion, NVO7alpha, NX001, Nyclobate, Nyox, Nysa, Obarcort, 00002417, OC2286, ocaratuzumab, OCTSG815, Oedemase, Oedemase-D, ofatumumab, Ofgy1-O, Ofvista, OHR118, OKi, Okifen, Oksamen, Olai, olokizumab, Omeprose E, Omnacortil, Omneed, Omniclor, Omnigel, Omniwel, onercept, 0N04057, ONS1210, ONS1220, Ontac Plus, Ontak, ONX0914, OPC6535, opebacan, OPN101, OPN201, OPN302, OPN305, OPN401, oprelvekin, OPT66, Optifer, Optiflur, OptiMIRA, Orabase Hca, Oradexon, Oraflex, OralFenac, Oralog, Oralpred, Ora-sed, Orasone, orBec, Orbone forte, Orel, ORE10002, Orencia, Org214007, Org217993, Org219517, Org223119, Org37663, Org39141, Org48762, Org48775, Orgadrone, Ormoxen, Orofen Plus, Oromylase Biogaran, Orthal Forte, Ortho Flex, Orthoclone OKT3, Orthofen, Orthoflam, Orthogesic, Orthoglu, Ortho-II Orthomac, Ortho-Plus, Ortinims, Ortofen, Orudis, Oruvail, OS2, Oscart, Osmetone, Ospain, Ossilife, Ostelox, Osteluc, Osteocerin, osteopontin, Osteral, otelixizumab, Otipax, Ou Ning, OvaSave, OX40 Ligand Antibody, Oxa, Oxagesic CB, Oxalgin DP, oxaprozin, OXCQ, Oxeno, Oxib MD, Oxibut, Oxicam, Oxiklorin, Oximal, Oxynal, oxyphenbutazone, ozoralizumab, P13 peptide, P1639, P21, P2X7 Antagonists, p38 Alpha Inhibitor, p38 Antagonist, p38 MAP kinase inhibitor, p38alpha MAP Kinase Inhibitor, P7 peptide, P7170, P979, PA40I, PA517, Pabi-dexamethasone, PAC, PAC10649, paclitaxel, Painoxam, Paldon, Palima, pamapimod, Pamatase, Panafcort, Panafcortelone, Panewin, Pan-Graf, Panimun Bioral, Panmesone, Panodin SR, Panslay, Panzem, Panzem NCD, PAP1, papain, Papirzin, Pappen K Pap, Paptinim-D, paquinimod, PAR2 Antagonist, Paracetamol, Paradic, Parafen TAJ, Paramidin, Paranac, Parapar, Parci, parecoxib, Parixam, Parry-S, Partaj ect Busulfan, pateclizumab, Paxceed, PBI0032, PBI1101, PBI1308, PBI1393, PBI1607, PBI1737, PBI2856, PBI4419, P-Cam, PCI31523, PCI32765, PCI34051, PCI45261, PCI45292, PCI45308, PD360324, PDA001, PDE4 inhibitor, PDL241 antibody, PDL252, Pediapred, Pefree, pegacaristim, Peganix, Peg-Interleukin 12, pegsunercept, PEGylated arginine deiminase, peldesine, pelubiprofen, Penacle, penicillamine, Penostop, Pentalgin, Pentasa, Pentaud, pentostatin, Peon, Pepdase, Pepser, Peptirase, Pepzen, Pepzol, Percutalgine, Periochip, Peroxisome Proliferator Activated Receptor gamma modulators, Petizene, PF00344600, PF04171327, PF04236921, PF04308515, PF05230905, PF05280586, PF251802, PF3475952, PF3491390, PF3644022, PF4629991, PF4856880, PF5212367, PF5230896, PF547659, PF755616, PF9184, PG27, PG562, PG760564, PG8395, PGE3935199, PGE527667, PHS, PH797804, PHA408, Pharmaniaga Mefenamic acid, Pharmaniaga Meloxicam, Pheldin, Phenocept, phenylbutazone, PHY702, PI3K delta inhibitor, PI3 Gamma/Delta Inhibitor, PI3K Inhibitor, Picalm, pidotimod, piketoprofen, Pilelife, Pilopil, Pilovate, pimecrolimus, Pipethanen, Piractam, Pirexyl, Pirobet, Piroc, Pirocam, Pirofel, Pirogel, Piromed, Pirosol, Pirox, Piroxen, Piroxicam, piroxicam betadex, Piroxifar, Piroxil, Piroxim, Pixim, Pixykine, PKC Theta Inhibitor, PL3100, PL5100 Diclofenac, Placenta Polypeptide, Plaquenil, plerixafor, Plocfen, PLR14, PLR18, Plutin, PLX3397, PLX5622, PLX647, PLX-BMT, pms-Diclofenac, pms-Ibuprofen, pms-Leflunomide, pms-Meloxicam, pms-Piroxicam, pms-Prednisolone, pms-Sulfasalazine, pms-Tiaprofenic, PMX53, PN0615, PN100, PN951, podofilox, POL6326, Polcortolon, Polyderm, Polygam S/D, Polyphlogin, Poncif, Ponstan, Ponstil Forte, Porine-A Neoral, Potaba, potassium aminobenzoate, Potencort, Povidone, povidone iodine, pralnacasan, Prandin, Prebel, Precodil, Precortisyl Forte, Precortyl, Predfoam, Predicort, Predicorten, Predilab, Predilone, Predmetil, Predmix, Predna, Prednesol, Predni, prednicarbate, Prednicort, Prednidib, Prednifarma, Prednilasea, prednisolone, Deltacortril (prednisolone), prednisolone acetate, prednisolone sodium phosphate, prednisolone sodium succinate, prednisone, prednisone acetate, Prednitop, Prednol-L, Prednox, Predone, Predonema, Predsol, Predsolone, Predsone, Predval, Preflam, Prelon, Prenaxol, Prenolone, Preservex, Preservin, Presol, Preson, Prexige, Priliximab, Primacort, Primmuno, Primofenac, prinaberel, Privigen, Prixam, Probuxil, Procarne, Prochymal, Procider-EF, Proctocir, Prodase, Prodel B, Prodent, Prodent Verde, Proepa, Profecom, Profenac L, Profenid, Profenol, Proflam, Proflex, Progesic Z, proglumetacin, proglumetacin maleate, Prograf, Prolase, Prolixan, promethazine hydrochloride, Promostem, Promune, PronaB, pronase, Pronat, Prongs, Pronison, Prontoflam, Propaderm-L, Propodezas, Propolisol, Proponol, propyl nicotinate, Prostaloc, Prostapol, Protacin, Protase, Protease Inhibitors, Protectan, Proteinase Activated Receptor 2 Inhibitor, Protofen, Protrin, Proxalyoc, Proxidol, Proxigel, Proxil, Proxym, Prozym, PRT062070, PRT2607, PRTX100, PRTX200, PRX106, PRX167700, Prysolone, PS031291, PS375179, PS386113, PS540446, PS608504, PS826957, PS873266, Psorid, PT, PT17, PTL101, P-Transfer Factor peptides, PTX3, Pulminiq, Pulsonid, Purazen, Pursin, PVS40200, PX101, PX106491, PX114, PXS2000, PXS2076, PYM60001, Pyralvex, Pyranim, pyrazinobutazone, Pyrenol, Pyricam, Pyrodex, Pyroxi-Kid, QAX576, Qianbobiyan, QPI1002, QR440, qT3, Quiacort, Quidofil, R107s, R125224, R1295, R132811, R1487, R1503, R1524, R1628, R333, R348, R548, R7277, R788, rabeximod, Radix Isatidis, Radofen, Raipeck, Rambazole, Randazima, Rapacan, Rapamune, Raptiva, Ravax, Rayos, RDEA119, RDEA436, RDP58, Reactine, Rebif, REC200, Recartix-DN, receptor for advanced glycation end products antibody, Reclast, Reclofen, recombinant HSA-TTMP-2, recombinant human alkaline phosphatase, recombinant Interferon Gamma, Recombinant human alkaline phosphatase, Reconil, Rectagel HC, Recticin, Recto Menaderm, Rectos, Redipred, Redolet, Refastin, Regenica, REGN88, Relafen, Relaxib, Relev, Relex, Relifen, Relifex, Relitch, Rematof, remestemcel-1, Remesulidum, Remicade® (infliximab), Remsima, ReN1869, Renacept, Renfor, Renodapt, Renodapt-S, Renta, Reosan, Repare-AR, Reparilexin, reparixin, Repertaxin, Repisprin, Resochin, Resol, resolvin El, Resurgil, Re-tin-colloid, Retoz, Reumacap, Reumacon, Reumadolor, Reumador, Reumanisal, Reumazin, Reumel, Reumotec, Reuquinol, revamilast, Revascor, Reviroc, Revlimid, Revmoksikam, Rewalk, Rexalgan, RG2077, RG3421, RG4934 antibody, RG7416, RG7624, Rheila, Rheoma, Rheprox, Rheudenolone, Rheufen, Rheugesic, Rheumacid, Rheumacort, Rheumatrex, Rheumesser, Rheumid, Rheumon, Rheumox, Rheuoxib, Rhewlin, Rhucin, RhuDex, Rhulef, Ribox, Ribunal, Ridaura, rifaximin, rilonacept, rimacalib, Rimase, Rimate, Rimatil, Rimesid, risedronate sodium, Ritamine, Rito, Rituxan, rituximab, RNS60, RO1138452, Ro313948, RO3244794, RO5310074, Rob803, Rocamix, Rocas, Rofeb, rofecoxib, Rofee, Rofewal, Roficip Plus, Rojepen, Rokam, Rolodiquim, Romacox Fort, Romatim, romazarit, Ronaben, ronacaleret, Ronoxcin, RDR Gamma T Antagonist, ROR gamma t inverse agonists, Rosecin, rosiglitazone, Rosmarinic acid, Rotan, Rotec, Rothacin, Roxam, Roxib, Roxicam, Roxopro, Roxygin DT, RP54745, RPI78, RPI78M, RPI78MN, RPIMN, RQ00000007, RQ00000008, RTA402, R-Tyflam, Rubicalm, Rubifen, Ruma pap, Rumalef, Rumidol, Rumifen, Runomex, rusalatide acetate, ruxolitinib, RWJ445380, RX10001, Rycloser MR, Rydol, S1P Receptor Agonists, S1P Receptor Modulators, S1P1 Agonist, S1P1 receptor agonist, S2474, S3013, SA237, SA6541, Saaz, S-adenosyl-L-methionine-sulfate-p-toluene sulfonate, Sala, Salazidin, Salazine, Salazopyrin, Salcon, Salicam, salsalate, Sameron, SAN300, Sanaven, Sandimmun, Sandoglobulin, Sanexon, SangCya, SAR153191, SAR302503, SAR479746, Sarapep, sargramostim, Sativex, Savantac, Save, Saxizon, Sazo, SB1578, SB210396, SB217969, SB242235, SB273005, SB281832, SB683698, SB751689, SBI087, SC080036, SC12267, SC409, Scaflam, SCD ketoprofen, SCI0323, SCI0469, SD-15, SD281, SDP051 antibody, Sd-rxRNA, secukinumab, Sedase, Sedilax, Sefdene, Seizyme, SEL113, Seladin, Selecox, selectin P ligand antibody, Glucocorticoid Receptor Agonist, Selectofen, Selektine, SelK1 antibody, Seloxx, Selspot, Selzen, Selzenta, Selzentry, semapimod, semapimod hydrochloride, semparatide, Senafen, Sendipen, Senterlic, SEP119249, Sepdase, Septirose, Seractil, Serafen-P, Serase, Seratid D, Seratiopeptidase, Serato-M, Seratoma Forte, Serazyme, Serezon, Sero, Serodase, Serpicam, Serra, serrapeptase, Serratin, Serratiopeptidase, Serrazyme, Servisone, Seven E P, SGI1252, SGN30, SGN70, SGX203, shark cartilage extract, Sheril, Shield, Shifazen, Shifazen-Fort, Shincort, Shiosol, ShK186, Shuanghuangxiaoyan, SI615, SI636, Sigmasporin, SIM916, Simpone, Simulect, Sinacort, Sinalgia, Sinapol, Sinatrol, Sinsia, siponimod, Sirolim, sirolimus, Siropan, Sirota, Sirova, sirukmnab, Sistal Forte, SKF105685, SKF105809, SKF106615, SKF86002, Skinalar, Skynim, Skytrip, SLAM family member 7 antibody, Slo-Indo, SM101, SM201 antibody, SM401, SMAD family member 7 oligonucleotide, SMART Anti-IL-12 Antibody, SMP114, SN0030908, SNO070131, sodium aurothiomalate, sodium chondroitin sulfate, sodium deoxyribonucleotide, sodium gualenate, sodium naproxen, sodium salicylate, Sodixen, Sofeo, Soleton, Solhidrol, Solicam, Soliky, Soliris, Sol-Melcort, Solomet, Solondo, Solone, Solu-Cort, Solu-Cortef, Solu-Decortin H, Solufen, Solu-Ket, Solumark, Solu-Medrol, Solupred, Somalgen, somatropin, Sonap, Sone, sonepeizumab, Sonexa, Sonim, Sonim P, Soonil, Soral, Sorenil, sotrastaurin acetate, SP-10, SP600125, Spanidin, SP-Cortil, SPD550, Spedace, sperm adhesion molecule 1, Spictol, spleen tyrosine kinase oligonucleotide, Sporin, S-prin, SPWF1501, SQ641, SQ922, SR318B, SR9025, SRT2104, SSR150106, SSR180575, SSSO7 antibody, ST1959, STA5326, stabilin 1 antibody, Stacort, Stalogesic, stanozolol, Staren, Starmelox, Stedex IND-SWIFT, Stelara, Stemin, Stenirol, Sterapred, Steriderm S, Sterio, Sterisone, Steron, stichodactyla helianthus peptide, Stickzenol A, Stiefcortil, Stimulan, STNM01, Store Operated Calcium Channel (SOCC) Modulator, STP432, STP900, Stratasin, Stridimmune, Strigraf, SU Medrol, Subreum, Subuton, Succicort, Succimed, Sulan, Sulcolon, Sulfasalazin Heyl, Sulfasalazin, Sulfovit, Sulidac, Sulide, sulindac, Sulindex, Sulinton, Sulphafine, Surnilu, SUN597, Suprafen, Supretic, Supsidine, Surgam, Surgamine, Surugamu, Suspen, Suton, Suvenyl, Suwei, SW Dexasone, Syk Family Kinase Inhibitor, Syn1002, Synacran, Synacthen, Synalar C, Synalar, Synavive, Synercort, Sypresta, T cell cytokine-inducing surface molecule antibody, T cell receptor antibody, T5224, T5226, TA101, TA112, TA383, TA5493, tabalumab, Tacedin, Tacgraf, TACIFc5, Tacrobell, Tacrograf, Tacrol, tacrolimus, Tadekinig alpha, Tadolak, TAFA93, Tafirol Artro, Taizen, TAK603, TAK715, TAK783, Takfa, Taksta, talarozole, Talfin, Talmain, talmapimod, Talmea, Talnif, talniflumate, Talos, Talpain, Talumat, Tamalgen, Tamceton, Tamezon, Tandrilax, tannins, Tannosynt, Tantum, tanzisertib, Tapain-beta, Tapoein, Tarenac, tarenflurbil, Tarimus, Tarproxen, Tauxib, Tazomust, TBR652, TC5619, T-cell, immune regulator 1, ATPase, H+ transporting, lysosomal V0 subunit A3 antibody, TCK1, T-cort, T-Dexa, Tecelac, Tecon, teduglutide, Teecort, Tegeline, Tementil, temoporfin, Tencam, Tendrone, Tenefuse, Tenfly, tenidap sodium, Tenocam, Tenoflex, Tenoksan, Tenotil, tenoxicam, Tenoxim, Tepadina, Teracort, Teradol, tetomilast, TG0054, TG1060, TG20, TG20, tgAAC94, Th1/Th2 Cytokine Synthase Inhibitor, Th-17 cell inhibitors, Thalido, thalidomide, Thalomid, Themisera, Thenii, Therafectin, Therapyace, thiarabine, Thiazolopyrimi dines, thioctic acid, thiotepa, THR090717, THR0921, Threenofen, Thrombate III, Thymic peptide, Thymodepressin, Thymogam, Thymoglobulin, Thymoglobuline, Thymoj ect thymic peptides, thymoniodulin, thymopentin, thymopolypetides, tiaprofenic acid, tibezonium iodide, Ticoflex, tilmacoxib, Tilur, T-immune, Timocon, Tiorase, Tissop, TKB662, TL011, TLR4 antagonists, TLR8 inhibitor, TM120, TM400, TMX302, TNF Alpha inhibitor, TNF alpha-TNF receptor antagonist, TNF antibody, TNF receptor superfamily antagonists, TNF TWEAK Bi-Specific, TNF-Kinoid, TNFQb, TNFR1 antagonist, TNR001, TNX100, TNX224, TNX336, TNX558, tocilizumab, tofacitinib, Tokuhon happ, TOL101, TOL102, Tolectin, ToleriMab, Tolerostem, Tolindol, toll-like receptor 4 antibody, toll-like receptor antibody, tolmetin sodium, Tongkeeper, Tonmex, Topflame, Topicort, Topleucon, Topnac, Toppin Ichthammol, toralizumab, Toraren, Torcoxia, Toroxx, Tory, Toselac, Totaryl, Touch-med, Touchron, Tovok, Toxic apis, Toyolyzom, TP4179, TPCA1, TPI526, TR14035, Tradil Fort, Traficet-EN, Tramace, tramadol hydrochloride, tranilast, Transimune, Transporina, Tratul, Trexall, Triacort, Triakort, Trialon, Triam, triamcinolone, triamcinolone acetate, triamcinolone acetonide, triamcinolone acetonide acetate, triamcinolone hexacetonide, Triamcort, Triamsicort, Trianex, Tricin, Tricort, Tricortone, TricOs T, Triderm, Trilac, Trilisate, Trinocort, Trinolone, Triolex, triptolide, Trisfen, Trivaris, TRK170, TRK530, Trocade, trolamine salicylate, Trolovol, Trosera, Trosera D, Trovcort, TRX1 antibody, TRX4, Trymoto, Trymoto-A, TT301, TT302, TT32, TT33, TTI314, tumor necrosis factor, tumor necrosis factor 2-methoxyethyl phosphorothioate oligonucleotide, tumor necrosis factor antibody, tumor necrosis factor kinoid, tumor necrosis factor oligonucleotide, tumor necrosis factor receptor superfamily, member I B antibody, tumor necrosis factor receptor superfamilyIB oligonucleotide, tumor necrosis factor superfamily, member 12 antibody, tumor necrosis factor superfamily, member 4 antibody, tumor protein p53 oligonucleotide, tumour necrosis factor alpha antibody, TuNEX, TXA127, TX-RAD, TYK2 inhibitors, Tysabri, ubidecarenone, Ucerase, ulodesine, Ultiflam, Ultrafastin, Ultrafen, Ultralan, U-Nice-B, Uniplus, Unitrexate, Unizen, Uphaxicam, UR13870, UR5269, UR67767, Uremol-HC, Urigon, U-Ritis, ustekinumab, V85546, Valcib, Valcox, valdecoxib, Yaldez, Valdixx, Valdy, Valentac, Vaioxib, Valtune, Valus AT, Valz, Valzer, Vamid, Vantal, Vantelin, VAP-1 SSAO Inhibitor, vapaliximab, varespladib methyl, Varicosin, Varidase, vascular adhesion protein-1 antibody, VB110, VB120, VB201, VBY285, Vectra-P, vedolizumab, Vefren, VEGFR-1 Antibody, Veldona, veltuzumab, Vendexine, Venimmun N, Veno forte, Venoglobulin-IH, Venozel, Veral, Verax, vercirnon, vero-dexamethasone, Vero-Kladribin, Vetazone, VGX1027, VGX750, Vibex MTX, vidofludimus, Vifenac, Vimovo, Vimultisa, Vincort, Vingraf, Vioform-HC, Vioxl, Vioxx, Virobron, visilizumab, Vivaglobin, Vivalde Plus, Vivian-A, VLST002, VLST003, VLST004, VLST005, VLST007, Voalla, voclosporin, Vokam, Vokmor, Volmax, Volna-K, Voltadol, Voltagesic, Voltanase, Voltanec, Voltaren, Voltarile, Voltic, Voren, vorsetuzumab, Votan-SR, VR909, VRA002, VRP1008, VRS826, VT111, VT214, VT224, VT310, VT346, VT362, VTX763, Vurdon, VX30 antibody, VX467, VXS, VX509, VX702, VX740, VX745, VX850, W54011, Walacort, Walix, WC3027, Wilgraf, Winflam, Winmol, Winpred, Winsolve, Wintogeno, WIP901, Woncox, WSB711 antibody, WSB712 antibody, WSB735, WSB961, X071NAB, X083NAB, Xantomicin Forte, Xedenol, Xefo, Xefocam, Xenar, Xepol, X-Flam, Xibra, Xicam, Xicotil, Xifaxan, XL499, XmAb5483, XmAb5485, XmAb5574, XmAb5871, XOMA052, Xpress, XProl 595, XtendTNF, XToll, Xtra, Xylex-H, Xynofen SR, Yang Shu-IVIG, YHB14112, YM974, Youfeline, Youfenac, Yuma, Yumerol, Yuroben, YY piroxicam, Z104657A, Zacy, Zaltokin, zaltoprofen, Zap70 Inhibitor, Zeepain, Zeloxim Fort, Zema-Pak, Zempack, Zempred, Zenapax, Zenas, Zenol, Zenos, Zenoxone, Zerax, Zerocam, Zerospasm, ZFNs, zinc oxide, Zipsor, ziralimumab, Zitis, Zix-S, Zocort, Zodixam, Zoftadex, zoledronic acid, Zolfin, Zolterol, Zopyrin, Zoralone, ZORprin, Zortress, ZP1848, zucapsaicin, Zunovate, Zwitterionic polysaccharides, ZY1400, Zybodies, Zycel, Zyrofen, Zyrogen Inhibitors, Zyser, Zytrim, and Zywin-Forte. In addition, the anti-inflammatory drugs, as listed above, may be combined with one or more agents listed above or herein or with other agents known in the art.

In some embodiments, the anti-inflammatory drug is delivered to the SCS of the eye using the microneedle devices and methods disclosed herein, and is used to treat, prevent, and/or ameliorate a posterior ocular disorder in a human or animal patient in need thereof. For example, the posterior ocular disorder or disorder selected from macular degeneration (e.g., age related macular degeneration, dry age related macular degeneration, exudative age-related macular degeneration, geographic atrophy associated with age related macular degeneration, neovascular (wet) age-related macular degeneration, neovascular maculopathy and age related macular degeneration, occult with no classic choroidal neovascularization (CNV) in age-related macular degeneration, Stargardt's disease, subfoveal wet age-related macular degeneration, and Vitreomacular Adhesion (VMA) associated with neovascular age related macular degeneration), macular edema, diabetic macular edema, uveitis, scleritis, chorioretinal inflammation, chorioretinitis, choroiditis, retinitis, retinochoroiditis, focal chorioretinal inflammation, focal chorioretinitis, focal choroiditis, focal retinitis, focal retinochoroiditis, disseminated chorioretinal inflammation, disseminated chorioretinitis, disseminated choroiditis, disseminated retinitis, disseminated reinochoroiditis, posterior cyclitis, Harada's disease, chorioretinal scars (e.g., macula scars of posterior pole, solar retinopathy), choroidal degeneration (e.g., atrophy, sclerosis), hereditary choroidal dystrophy (e.g., choroidermia, choroidal dystrophy, gyrate atrophy), choroidal hemorrhage and rupture, choroidal detachment, retinal detachment, retinoschisis, hypersentitive retinopathy, retinopathy, retinopathy of prematurity, epiretinal membrane, peripheral retinal degeneration, hereditary retinal dystrophy, retinitis pigmentosa, retinal hemorrhage, separation of retinal layers, central serous retinopathy, glaucoma, ocular hypertension, glaucoma suspect, primary open-angle glaucoma, primary angle-closure glaucoma, floaters, Leber's hereditary optic neropathy, optic disc drusen, inflammatory disorders of the eye, inflammatory lesions in fungal infections, inflammatory lesions, inflammatory pain, inflammatory skin diseases or disorders, Sjogren's syndrome, opthalmic for Sjogren's syndrome.

Examples of drugs that may be used to treat, prevent, and/or ameliorate macular degeneration that can be delivered to the SCS via the formulations and methods described herein include, but are not limited to: A0003, A36 peptide, AAV2-sFLT01, ACE041, ACU02, ACU3223, ACU4429, AdPEDF, aflibercept, AG13958, aganirsen, AGN150998, AGN745, AL39324, AL78898A, AL8309B, ALN-VEG01, alprostadil, AM1101, amyloid beta antibody, anecortave acetate, Anti-VEGFR-2 Alterase, Aptocine, APX003, ARC 1905, ARC 1905 with Lucentis, ATG3, ATP-binding cassette, sub-family A, member 4 gene, ATXS10, Avastin with Visudyne, AVT1O1, AVT2, bertilimumab, bevacizumab with verteporfin, bevasiranib sodium, bevasiranib sodium with ranibizumab, brimonidine tartrate, BVA301, canakinumab, Cand5, Cand5 with Lucentis, CERE 140, ciliary neurotrophic factor, CLT009, CNT02476, collagen monoclonal antibody, complement component 5 aptamer (pegylated), complement component 5 aptamer (pegylated) with ranibizumab, complement component C3, complement factor B antibody, complement factor D antibody, copper oxide with lutein, vitamin C, vitamin E, and zinc oxide, dalantercept, DE109, bevacizumab, ranibizumab, triamcinolone, triamcinolone acetonide, triamcinolone acetonide with verteporfin, dexamethasone, dexamethasone with ranibizumab and verteporfin, disitertide, DNA damage inducible transcript 4 oligonucleotide, E10030, E10030 with Lucentis, EC400, eculizumab, EGP, EHT204, embryonic stem cells, human stem cells, endoglin monoclonal antibody, EphB4 RTK Inhibitor, EphB4 Soluble Receptor, ESBA1008, ETX6991, Evizon, Eyebar, EyePromise Five, Eyevi, Eylea, F200, FCFD4514S, fenretinide, fluocinolone acetonide, fluocinolone acetonide with ranibizumab, fms-related tyrosine kinase 1 oligonucleotide, fms-related tyrosine kinase 1 oligonucleotide with kinase insert domain receptor 169, fosbretabulin tromethamine, Gamunex, GEM220, GS101, GSK933776, HC31496, Human n-CoDeR, HYB676, IBI-20089 with ranibizumab (Lucentis®), iCo-008, Iconl, I-Gold, Ilaris, Iluvien, Iluvien with Lucentis, immunoglobulins, integrin alpha5beta1 immunoglobulin fragments, Integrin inhibitor, IRIS Lutein, I-Sense Ocushield, Isonep, isopropyl unoprostone, JPE1375, JSM6427, KH902, LentiVue, LFG316, LP590, LPO1010AM, Lucentis, Lucentis with Visudyne, Lutein ekstra, Lutein with myrtillus extract, Lutein with zeaxanthin, M200, M200 with Lucentis, Macugen, MC1101, MCT355, mecamylamine, Microplasmin, motexafin lutetium, MP0112, NADPH oxidase inhibitors, aeterna shark cartilage extract (Arthrovas™, Neoretna™, Psovascar™), neurotrophin 4 gene, Nova21012, Nova21013, NT501, NT503, Nutri-Stulln, ocriplasmin, OcuXan, Oftan Macula, Optrin, ORA102 with bevaciziunab (Avastin®), P144, P17, Palomid 529, PAN90806. Panzem, PARP inhibitors, pazopanib hydrochloride, pegaptanib sodium, PF4523655, PG11047, piribedil, platelet-derived growth factor beta polypeptide aptamer (pegylated), platelet-derived growth factor beta polypeptide aptamer (pegylated) with ranibizumab, PLG101, PMX20005, PMX53, POT4, PRS055, PTK787, ranibizumab, ranibizumab with triamcinolone acetonide, ranibizumab with verteporfin, ranibizumab with volociximab, RD27, Rescula, Retaane, retinal pigment epithelial cells, RetinoStat, RG7417, RN6G, RT101, RTU007, SB267268, serpin peptidase inhibitor, Glade F, member 1 gene, shark cartilage extract, Shefl, SIR1046, SIR1G76, Sirna027, sirolimus, SMTD004, Snelvit, SOD Mimetics, Solaris, sonepcizumab, squalamine lactate, ST602, StarGen, T2TrpRS, TA106, talaporfin sodium, Tauroursodeoxycholic acid, TG100801, TK1, TLCx99, TRC093, TRC105, Trivastal Retard, TT30, Ursa, ursodiol, Vangiolux, VAR10200, vascular endothelial growth factor antibody, vascular endothelial growth factor B, vascular endothelial growth factor kinoid, vascular endothelial growth factor oligonucleotide, VAST Compounds, vatalanib, VEGF antagonist (e.g., as described herein), verteporfm, Visudyne, Visudyne with Lucentis and dexamethasone, Visudyne with triamcinolone acetonide, Vivis, volociximab, Votrient, XV615, zeaxanthin, ZFP TF, zinc-monocysteine and Zybrestat. In some embodiments, one or more of the macular degeneration treating drugs described above is combined with one or more agents listed above or herein or with other agents known in the art.

In some embodiments, the pharmaceutical agent delivered to the SCS using the methods described herein is an antagonist of a member of the platelet derived growth factor (PDGF) family, for example, a drug that inhibits, reduces or modulates the signaling and/or activity of PDGF-receptors (PDGFR). For example, the PDGF antagonist delivered to the SCS for the treatment of one or more posterior ocular disorders or choroidal maladies, in some embodiments, is an anti-PDGF aptamer, an anti-PDGF antibody or fragment thereof an anti-PDGFR antibody or fragment thereof or a small molecule antagonist. In some embodiments, the PDGF antagonist is an antagonist of the PDGFRa or PDGFRp. In some embodiments, the PDGF antagonist is the anti-PDGF-β aptamer E10030, sunitnib, axitinib, sorefenib, imatinib, imatinib mesylate, nintedanib, pazopanib HCl, ponatinib, MK-2461, Dovitinib, pazopanib, crenolanib, PP-121, telatinib, KRN 633, CP 673451, TSU-68, Ki8751, amuvatinib, tivozanib, masitinib, motesanib diphosphate, dovitinib dilactic acid, linifanib (ABT-869).

In some embodiments, a pharmaceutical agent that treats, prevents and/or ameliorates fibrosis is used in conjunction with the formulations and methods described herein and is delivered to the SCS of the eye. In some embodiments, the drug is interferon gamma 1b (Actimmune®) with pirfenidone, ACUHTR028, AlphaVBetaS, aminobenzoate potassium, amyloid P, ANG1122, ANG1170, ANG3062, ANG3281, ANG3298, ANG4011, Anti-CTGF RNAi, Aplidin, *Stragalus membranaceus* extract with salvia and *Schisandra chinensis*, atherosclerotic plaque blocker, Azof, AZX100, BB3, connective tissue growth factor antibody, CT140, danazol, Esbriet, EXC001, EXC002, EXC003, EXC004, EXC005, F647, FG3019, Fibrocorin, Follistatin, FT011, Galectin-3 inhibitors, GKT137831, GMCT01, GMCT02, GRMD01, GRMD02, GRN510, Heberon Alfa R, interferon alfa-2b, interferon gamma-1b with pirfenidone, ITMN520, JKB 119, JKB121, JKB122, KRX168, LPA1 receptor antagonist, MGN4220, MIA2, microRNA 29a oligonucleotide, MMI0100, noscapine, PBI4050, PBI4419, PDGFR inhibitor, PF-06473871, PGN0052, Pirespa, Pirfenex, pirfenidone, plitidepsin, PRM151, Px102, PYN17, PYN22 with PYN17, Relivergen, rhPTX2 Fusion Proteins, RXI109, secretin, STX100, TGF-beta Inhibitor, transforming growth factor, beta receptor 2 oligonucleotide, VA999260 or XV615. In some embodiments, one or more of the fibrosis treating drugs described above is combined with one or more agents listed above or herein or with other agents known in the art.

In some embodiments, a pharmaceutical agent that treats, prevents and/or ameliorates diabetic macular edema is used in conjunction with the formulations and methods described herein and is delivered to the SCS of the eye. In some embodiments, the drug is AKB9778, bevasiranib sodium, Candy, choline fenofibrate, Cortij ect, c-raf 2-methoxyethyl phosphorothioate oligonucleotide, DE109, dexamethasone, DNA damage inducible transcript 4 oligonucleotide, FOV2304, iCo007, KH902, MP0112, NCX434, Optina, Ozurdex, PF4523655, SAR1118, sirolimus, SK0503 or Tri-Lipix. In some embodiments, one or more of the diabetic macular edema treating drugs described above is combined with one or more agents listed above or herein or with other agents known in the art.

In some embodiments, a pharmaceutical agent that treats, prevents and/or ameliorates macular edema is used in conjunction with the formulations and methods described herein and is delivered to the SCS of the eye. In some embodiments, the drug is delivered to the SCS of a human subject in need of treatment of a posterior ocular disorder or choroidal malady via a hollow microneedle. In some embodiments, the drug is denufosol tetrasodium, dexamethasone, ecallantide, pegaptanib sodium, ranibizumab or triamcinolone. In addition, the drugs delivered to ocular tissues using the microneedle devices and methods disclosed herein which treat, prevent, and/or ameliorate macular edema, as listed above, may be combined with one or more agents listed above or herein or with other agents known in the art.

In some embodiments, a pharmaceutical agent that treats, prevents and/or ameliorates ocular hypertension is used in conjunction with the formulations and methods described herein and is delivered to the SCS of the eye. In some embodiments, the drug is 2-MeS-beta gamma-CC12-ATP, Aceta Diazol, acetazolamide, Aristomol, Arteoptic, AZD4017, Betalmic, betaxolol hydrochloride, Betimol, Betoptic S, Brimodin, Brimonal, brimonidine, brimonidine tartrate, Brinidin, Calte, carteolol hydrochloride, Cosopt, CS088, DE092, DE104, DE111, dorzolamide, dorzolamide hydrochloride, Dorzolamide hydrochloride with Timolol maleate, Droptimol, Fortinol, Glaumol, Hypadil, Ismotic, isopropyl unoprostone, isosorbide, Latalux, latanoprost, Latanoprost with Timolol maleate, levobunolol hydrochloride, Lotensin, Mannigen, mannitol, metipranolol, mifepristone, Mikelan, Minims Metipranolol, Mirol, nipradilol, Nor Tenz, Ocupress, olmesartan, Ophtalol, pilocarpine nitrate, Piobaj, Rescula, RU486, Rysmon TG, SAD448, Saflutan, Shemol, Taflotan, tafluprost, tafluprost with timolol, Thiaboot, Timocomod, timolol, Timolol Actavis, timolol hemihydrate, timolol maleate, Travast, travoprost, Unilat, Xalacom, Xalatan or Zomilol. In addition, the drugs delivered to the SCS using the microneedle devices and methods described herein which treat, prevent, and/or ameliorate ocular hypertension, as listed above, may be combined with one or more agents listed above or herein or with other agents known in the art.

Microneedles

The microneedle devices used for administration of the formulations provided herein include one or more microneedles. The microneedles may be hollow (e.g., where a fluid formulation is infused through the microneedle bore) or solid (e.g., where the fluid formulation is coated onto the microneedle or is contained within the microneedles such as within a porous matrix). The device also may include an elongated housing for holding the proximal end of the microneedle.

As used herein, the terms "proximal" and "distal" refer to a position that is closer to and away from, respectively, a relative position. For example, an operator (e.g., surgeon, physician, nurse, technician, etc.) inserting the microneedle device into the patient would insert the tip-end portion of the microneedle device into the ocular tissue first. Thus, the tip-end portion of the microneedle would be referred to as the distal end, while the opposite end of the microneedle (e.g., the base or end of the microneedle device being manipulated by the operator) would be the proximal end.

As used herein, the term "microneedle" refers to a structure having a base, a shaft, and a tip end suitable for insertion into the ocular tissue and has dimensions suitable for minimally invasive insertion and administration of the formulations described herein. That is, the microneedle has a length or effective length from about 50 μm to about 2000 microns and a width (or diameter) from about 20 μm to about 500 μm.

In various embodiments, the microneedle may have a length of from about 50 μm, about 75 μm, about 100 μm, about 200 μm, about 300 μm, about 400 μm, or about 500 μm up to about 1500 μm, about 1250 μm, about 1000, about 999 μm, about 900 μm, about 800 μm, about 700 μm, about 600 μm, or about 500 μm. For example, in some embodiments the microneedle may have a length from about 600 μm to about 1300 μm, about 700 μm to about 1200 μm, or about 800 μm to about 1100 μm.

In various embodiments, the proximal portion of the microneedle (i.e., the portion nearest its base) may have a width or cross-sectional dimension of from about 20 μm, about 40 μm, about 60 μm, about 80 μm, about 100 μm, about 150 μm, or about 200 μm up to about 500 μm, about 400 μm, about 350 μm, about 300 μm, about 250 μm, or about 200 μm. For example, in some embodiments the microneedle may have a width at its base from about 100 μm to about 400 μm, from about 150 μm to about 400 μm, from about 200 μm to about 300 μm, or from about 250 μm to about 400 μm.

In some embodiments, the tip end of the microneedle may have a planar or curved bevel. For example, a curved bevel may have a radius of curvature at its tip that is specially configured for the type of tissue that is being targeted. In one aspect, the tip end of the microneedle may have a radius of curvature at its tip of from about 100 nm to about 50 μm. For example, the tip end of the microneedle may have a radius of curvature at its tip of from about 200 nm, about 500 nm, about 1000 nm, about 2000 nm, about 5000 nm, or about 10,000 nm up to about 40 μm, about 30 μm, about 20 μm, or about 10,000 nm.

In some embodiments, the microneedle extends from a base that may be integral with or separate from the microneedle. The base may be rigid or flexible and substantially planar or curved. For example, the base may be shaped to minimize contact between the base and the ocular tissue at the point of insertion and/or so as to counteract the deflection of the ocular tissue and facilitate insertion of the microneedle into the ocular tissue (e.g., extending toward the tip portion of the microneedle so as to "pinch" the ocular tissue). In other embodiments, a base tapers away from the tissue into which it is being inserted, which may permit the base to accommodate the tissue surface deformation that occurs during microneedle insertion.

In some embodiments, the microneedle device includes a single hollow microneedle. As used herein, the term "hollow" includes a single straight bore through the center of the microneedle, as well as multiple bores, bores that follow complex paths through the microneedles, multiple entry and exit points from the bore(s), and intersecting or networks of bores. That is, a hollow microneedle has a structure that includes one or more continuous pathways from the base of the microneedle to an exit in the shaft and/or tip portion of the microneedle distal to the base. In such embodiments, the device may further include a means for conducting a fluid formulation through the hollow microneedle. For example, the means may be a flexible or rigid conduit in fluid connection with the base or proximal end of the microneedle. The means may also include a pump or other devices for creating a pressure gradient for inducing fluid flow through the device. The conduit may be in operable connection with a source of the fluid formulation. For example, the source may be any suitable container, such as a conventional syringe or a disposable unit dose container. The microneedle device may further include a fluid reservoir for containing a fluid formulation or liquid formulation, the fluid formulation or liquid formulation being in operable communication with the bore of the microneedle at a location distal to the tip end of the microneedle. The fluid reservoir may be integral with the microneedle, integral with the adaptor, or separate from both the microneedle and adaptor. The fluid reservoir may be the interior of a syringe.

In some embodiments, the microneedle device may include an assembly or array of two or more microneedles. For example, the device may include an array of between two and 100 microneedles (e.g., any number from two, three, five, 10, 20, and 50). In some embodiments, the array of microneedles may include a combination of different microneedles. For instance, the array may include microneedles of various lengths, base portion diameters, tip portion shapes, spacings, coatings, and the like.

The microneedles can be formed/constructed of different biocompatible materials, including metals, glasses, semiconductor materials, ceramics, or polymers. Exemplary metals include pharmaceutical grade stainless steel, gold, titanium, nickel, iron, gold, tin, chromium, copper, and alloys thereof. Exemplary polymers may be biodegradable or non-biodegradable. Non-limiting examples of biodegradable polymers include polylactides, polyglycolides, polylactide-co-glycolides (PLGA), polyanhydrides, polyorthoesters, polyetheresters, polycaprolactones, polyesteramides, poly (butyric acid), poly(valeric acid), polyurethanes and copolymers and blends thereof. Non-limiting examples of non-biodegradable polymers include various thermoplastics or other polymeric structural materials known in the fabrication of medical devices, such as nylons, polyesters, polycarbonates, polyacrylates, polymers of ethylene-vinyl-acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, and blends and copolymers thereof. Biodegradable microneedles may be beneficial by providing an increased level of safety as compared to non-biodegradable ones, such that the microneedles are essentially harmless even if inadvertently broken off into the ocular tissue or are rendered unsuitable for use.

The microneedle can be fabricated by a variety of methods known in the art or as described in the examples. In some embodiments, the microneedle is fabricated using a laser or similar optical energy source. For example, a hollow microneedle may be fabricated from a microcannula cut using a laser to the desired microneedle length. The laser may also be used to shape single or multiple tip openings for hollow microneedles. Single or multiple cuts may be performed on a single microcannula to shape the desired microneedle structure (e.g., to obtain the desired radius of curvature at the microneedle tip). In one example, the microcannula may be made of metal such as stainless steel and cut using a laser with a wavelength in the infrared region of the light spectrum (0.7-300 µm wavelength). Further refinement may be performed using metal electropolishing techniques familiar to those in the field. In another embodiment, the microneedle length and optional bevel shape is formed by a physical grinding process, which for example, may include grinding a metal cannula against a moving abrasive surface. The fabrication process may further include precision grinding, micro-bead jet blasting and ultrasonic cleaning to form the shape of the desired precision tip of the microneedle.

Further details of possible manufacturing techniques are described, for example, in PCT Publication No. WO 2014/036009, U.S. Patent Application Publication No. 2006/0086689 to Raju et al., U.S. Patent Application Publication No. 2006/0084942 to Kim et al., U.S. Patent Application Publication No. 2005/0209565 to Yuzhakov et al., U.S. Patent Application Publication No. 2002/0082543 to Park et al., U.S. Pat. No. 6,334,856 to Allen et al., U.S. Pat. No. 6,611,707 to Prausnitz et al., or U.S. Pat. No. 6,743,211 to Prausnitz et al.

Targeted delivery using the formulations and methods provided herein is enabled at least in part due to the small size of the microneedles and ability to position the microneedles near specific tissues. In some embodiments, to target a specific tissue, the microneedle is positioned on the surface of the eye near the target tissue and then inserted to a controlled depth into the eye such that it reaches the tissue of interest. The depth of microneedle insertion can be controlled by the length of the microneedle, the force that is applied to the microneedle, the presence of additional device elements associated with the microneedle that controls its penetration depth, and by use of feedback mechanisms. In addition, the depth of insertion can be influenced by the thickness and mechanical properties of tissues in the path of the microneedle insertion. Specifically, deformation of the tissue can influence the depth of insertion, where tissue deformation can lead to less deep insertion if, for example, an indentation or dimple is formed on the surface of the tissue.

Feedback mechanisms that may be used to provide information about depth of insertion include one or more imaging techniques, such as ultrasound, optical coherence tomography, optical microscopy including fluorescence, confocal and other methods, and other imaging methods known in the art. These imaging techniques can also be used to provide information, such as tissue thickness, to guide subsequent microneedle use. Thus, feedback can be information obtained in advance of, during, or following insertion of the microneedle. Other forms of feedback can include electrical measurements, optical measurements, mechanical measurements, and the like. For example, as a microneedle passes through different tissues, the mechanical properties of the tissues may vary such that mechanical feedback about the microneedle's location with respect to the tissues can be obtained. Likewise, different tissues can have different electrical properties such that measurement of electrical properties can provide information about location in tissues.

In the descriptions provided herein, the terms "includes," "is," "containing," "having," and "comprises" are used in an open-ended fashion, and thus should be interpreted to mean "including, but not limited to." When methods and metal interconnects are claimed or described in terms of "comprising" various components or processing features, the composite materials and methods can also "consist essentially of" or "consist of" the various components or processing features, unless stated otherwise.

The terms "a," "an," and "the" are intended to include plural alternatives, e.g., at least one. For instance, the disclosure of "a pharmaceutical agent," "a binding molecule," "a fluid formulation", and the like, is meant to encompass one, or mixtures or combinations of more than one pharmaceutical agent, binding molecule, fluid formulation, and the like, unless otherwise specified.

Various numerical ranges may be disclosed herein. When Applicant discloses or claims a range of any type, Applicant's intent is to disclose or claim individually each possible number that such a range could reasonably encompass, including end points of the range as well as any sub-ranges and combinations of sub-ranges encompassed therein, unless otherwise specified. Moreover, all numerical end points of ranges disclosed herein are approximate. As a representative example, Applicant discloses, in some embodiments, that "the pharmaceutical agent has a clearance time from the suprachoroidal space of 3 days to 21 days." This range should be interpreted as encompassing values of "clearance" in a range of about 3 days to about 21 days, and further encompasses "about" each of 4 days, 5 days, 6 days, 7 days, 8 days, 9 days, 10 days, 11 days, 12 days, 13 days, 14 days, 15 days, 16 days, 17 days, 18 days, 19 days, and 20 days, including any ranges and sub-ranges between any of these values.

The term "about," as used herein, indicates the value of a given quantity can include quantities ranging within 10% of the stated value, or optionally within 5% of the value, or in some embodiments within 1% of the value, or in some embodiments within 0.1% of the value. For example, about 0.5 may include about 0.45 and 0.55, about 10 may include 9 and 11, about 1000 may include 900 to 1100.

EXAMPLES

The present invention is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may suggest themselves to one of ordinary skill in the art without departing from the spirit of the present invention or the scope of the appended claims. Thus, other aspects of this invention will be apparent to those skilled in the art from consideration of the specification and practice of the invention disclosed herein.

Example 1—Distribution of Particles and Molecules in the SCS

The tests of this example determined the effect of injection volume, formulation composition, and time on circumferential spread of particles, small molecules and polymeric formulation excipients in the SCS after microneedle injection into New Zealand White rabbit eyes ex vivo and in vivo.

Microneedle injections of 25-150 µL Hank's Balanced Salt Solution (HBSS) containing 0.2 µm red-fluorescent particles and a model small molecule (fluorescein) were performed in rabbit eyes ex vivo, and visualized via flat mount. Particles with diameters of 0.02-2 µm were co-injected into SCS in vivo with fluorescein or a polymeric formulation excipient: fluorescein isothiocyanate (FITC)-labeled DisCoVisc® or FITC-labeled carboxymethyl cellulose (CMC). Fluorescent fundus images were acquired over time to determine area of particle, fluorescein and polymeric formulation excipient spread, as well as their co-localization. It was determined that fluorescein covered a significantly larger area than co-injected particles when suspended in HBSS, and that this difference was present from 3 minutes post-injection onwards. It also was demonstrated that there was no difference in initial area covered by FITC-DisCoVisc® and particles; the transport time (i.e., the time until the FITC-DisCoVisc® and particle area began dissociating) was 2 days. There was also no difference in initial area covered by FITC-CMC and particles; the transport time in FITC-CMC was 4 days. It also was determined that particle size (20 nm-2 µm) had no effect on spreading area when delivered in HBSS or DisCoVisc®.

Therefore, the tests of this example demonstrated that (i) the area of particle spread in SCS during injection generally increased with increasing injection volume, was unaffected by particle size and was significantly less than the area of fluorescein spread, (ii) particles suspended in low-viscosity HBSS formulation were entrapped in the SCS after injection, whereas fluorescein was not and (iii) particles co-injected with viscous polymeric formulation excipients co-localized near the site of injection in the SCS, continued to co-localize while spreading over larger areas for 2-4 days, and then no longer co-localized as the polymeric formulation excipients were cleared within 1-3 weeks and the particles remained largely in place. These data suggest that particles encounter greater barriers to flow in SCS compared to molecules and that co-localization of particles and polymeric formulation excipients allow spreading over larger areas of the SCS until the particles and excipients dissociate.

In this example, tests were performed to determine if the circumferential area of particle coverage increases with increasing injection volume, and whether small molecules (fluorescein) spread more than particles. The percentage area of the SCS that had red and green fluorescence greater than threshold after injection of increasing volumes into the rabbit SCS ex vivo using flat mounts was calculated, as shown at FIG. 1. It was discovered that, with HBSS as the formulation, the area covered by fluorescein was larger than the area covered by particles for all injection volumes tested immediately after injection. On average, the fluorescein occupied an area twice as large as that occupied by particles ex vivo and in vivo. The difference in area covered may have been due either to barriers in the SCS that preferentially limited movement of particles or to increased diffusion of fluorescein in the SCS post-injection relative to the particles. Since the contribution of fluorescein diffusion was estimated to increase coverage by only ~20%, entrapment of particles is the more likely explanation. Because molecules distributed to cover a larger area than particles in the SCS in this example, the delivery of molecules may be preferred if the goal is to achieve full coverage of the SCS. However, the use of particles (e.g., containing drug molecules for slow release over time) may, in some instances, be preferable to injecting free drug molecules, which are usually cleared from the SCS within a day.

The area covered by fluorescein and particles generally increased with increasing injection volume, although the rate of increase was larger at lower volumes (see FIG. 1). A linear fit to the data yielded a poor correlation ($r^2$=0.51 for particles and 0.67 for fluorescein), whereas an exponential fit was better ($r^2$=0.90 for particles and $r^2$=0.69 for fluorescein), which is consistent with the observation that area initially increased and appeared to approach a plateau value slightly below 50% area coverage for particles and slightly above 50% for fluorescein. This apparent plateauing behavior may have been due to anatomical barriers that inhibit coverage in the inferior hemisphere, especially for particles.

For all injection volumes, the fluorescein occupied a larger area than the red-fluorescent particles (p<0.0001, ANOVA). The ratio of area covered by fluorescein versus particles was 2.05±0.24 (mean±SEM), which, at least in this example, did not significantly depend on injection volume (p=0.36, F test). This difference in area may have been due to the higher diffusivity of fluorescein versus particles (which are assumed to transport only by convection). However, diffusion of fluorescein for 3 minutes after injection is expected to account for an area increase of only ~20% (based on a calculation assuming a fluorescein diffusivity of $4.3 \times 10^{-6}$ cm$^2$/s and a covered SCS area of ~200 mm$^2$ in the rabbit eye. Because this small predicted increase is much less than the roughly two-fold measured increase, this result suggests that there may be additional factors at play in the SCS that limit movement of particles relative to small molecules (i.e., fluorescein).

Also investigated was the role of formulation and time on particle distribution in the SCS. The distribution of red-fluorescent particles suspended with green fluorescently-tagged formulation excipients in HBSS after injection into the SCS of live rabbits was imaged using red and green fluorescence simultaneously. Fluorescence was imaged using RetCam imaging, which was preferred to other non-contact fundus imaging methods, since it enabled visualization of the posterior pole as well as the far periphery (i.e., the injection site). The percentage of the SCS area in the composite images that had red/green fluorescence values at least 0.1% of the starting concentration was then calculated, and this calculation was used as a proxy of true coverage; and determined the incidence of co-localization of the red and green fluorescence greater than chance.

To determine the distribution of red-fluorescent particles and green-fluorescent fluorescein molecules injected in HBSS (FIG. 2), the SCS area over which the particles and fluorescein spread for 21 days after injection in vivo was determined. The particle area coverage was constant at all time points from 3 minutes to 14 days post-injection (p=0.99, Sidak's multiple comparison test), with a small decrease in area at 21 days. In contrast, the fluorescein area increased from 3 minutes to 1 hour post-injection before being cleared by 2 days. At the 3 minute and 1 hour time points, fluorescein covered a larger area than the red particles (p<0.01, Sidak's multiple comparison test). At later time points (14 days and 21 days), there was a decrease in thresholded area, which may have been due to photobleaching. Moreover, the time point at which the maximum fluorescein coverage was measured was later than the red particle maximum. Statistical analysis showed that the particles co-localized with fluorescein immediately after injection, but not at later time points. Taken together with the ex vivo data, it was concluded that particles suspended in HBSS became immobilized immediately post-injection even though fluorescein was able to move within the SCS well after the injection, and was ultimately cleared within 2 days.

Also investigated was how the addition of viscous polymeric formulation excipients affected particle distribution over time. When the formulation consisted of red particles suspended in 5% FITC-CMC in HBSS (FIG. 3), particle area coverage increased from 3 minutes until 2 days post-injection (p<0.01, Sidak's multiple comparison test). Then, from 2 days to 35 days, there was no significant change in particle distribution in the SCS (p=0.61, Sidak's multiple comparison test). The co-injected FITC-labeled CMC initially followed a pattern similar to the particles, increasing in area for the first two days (p<0.005, Sidak's multiple comparison test). However, from 2 days until 21 days, the area of FITC-CMC decreased (p<0.005, Sidak's multiple comparison), and from 21 days until 35 days, there was essentially no detectable FITC-CMC in the SCS. The FITC-CMC never occupied an area larger than the red particles (p>0.07, Sidak's multiple comparison test). The maximum red particle coverage and maximum FITC-CMC coverage occurred at the same time point, i.e., 2 days post injection. The last time point of co-localization was at 4 days. This likely suggested that the particles and FITC-CMC were transported together during the injection and for up to 2 days thereafter, after which the particles remained immobilized and the FITC-CMC was cleared.

When the formulation consisted of red particles suspended in FITC-DisCoVisc® (FIG. 4), particle coverage was constant from 3 minutes to 1 hour (p=0.98, Sidak's multiple comparison test), and then increased by 2 days (p<0.05, Sidak's multiple comparison test). There was no significant change in particle coverage from 2 days to 21 days (p>0.24, Sidak's multiple comparison test). The co-injected FITC-labeled DisCoVisc® molecules initially followed a pattern similar to the particles, increasing in area for the first two days (p<0.005, Sidak's multiple comparison test). However, from 2 days until 7 days, the area of FITC-DisCoVisc® decreased (p<0.005, Sidak's multiple comparison), and from 7 days until 21 days, there was essentially no detectable FITC-DisCoVisc® in the SCS. The FITC-DisCoVisc® never occupied an area larger than the red particles (p>0.05, Sidak's multiple comparison test). The maximum red particle coverage and maximum FITC-Discovisc coverage occurred at the same time point, i.e., 2 days post injection. The last time point of co-localization was at 2 days. This appeared to suggest behavior similar to that seen with FITC-CMC, where the particles and FITC-DisCoVisc® were transported together during the injection and for up to 2 days thereafter, after which the particles remained immobilized and the FITC-DisCoVisc® was cleared, although the FITC-DisCoVisc® was cleared faster than the FITC-CMC and, on an absolute scale, the area coverage of FITC-DisCoVisc® and co-injected particles was roughly twice as large as the area coverage of FITC-CMC and co-injected particles.

Figure 2:
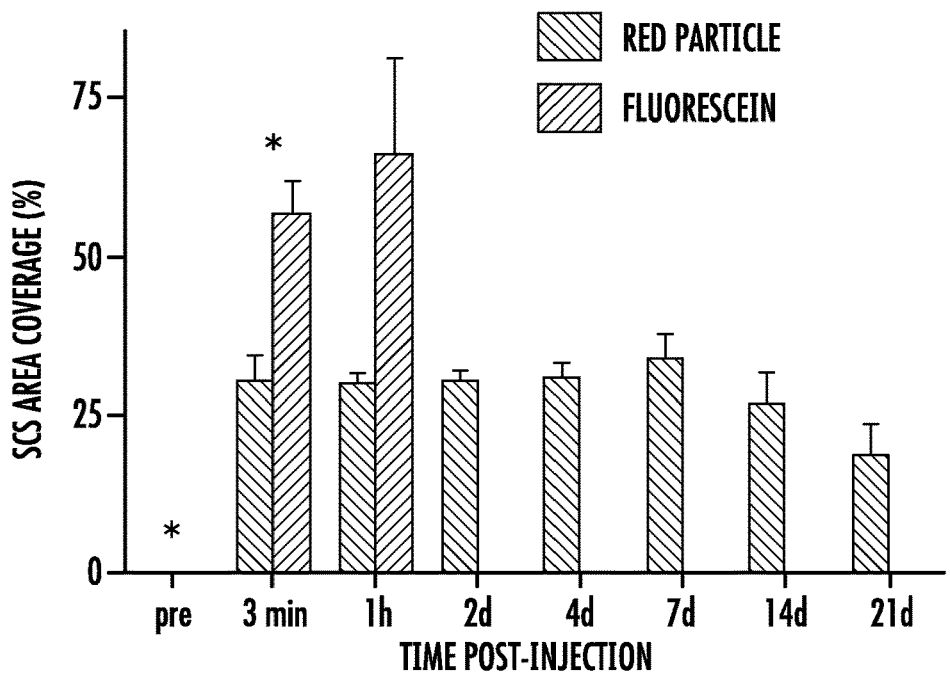
FIG. 2 depicts a quantification of area covered (mean±SEM, N=3) by red-fluorescent particles and fluorescein in HBSS in several embodiments.
Figure 3:
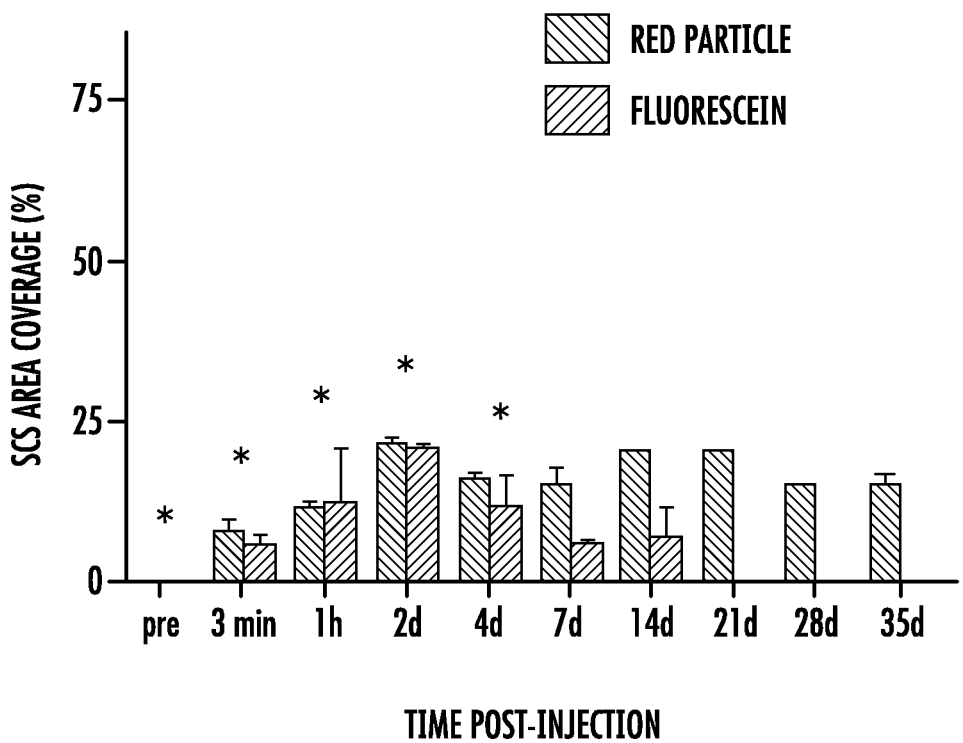
FIG. 3 depicts a quantification of area covered (mean±SEM, N=2-4) by red fluorescent particles and FITC-CMC in HBSS in several embodiments.
Figure 4:
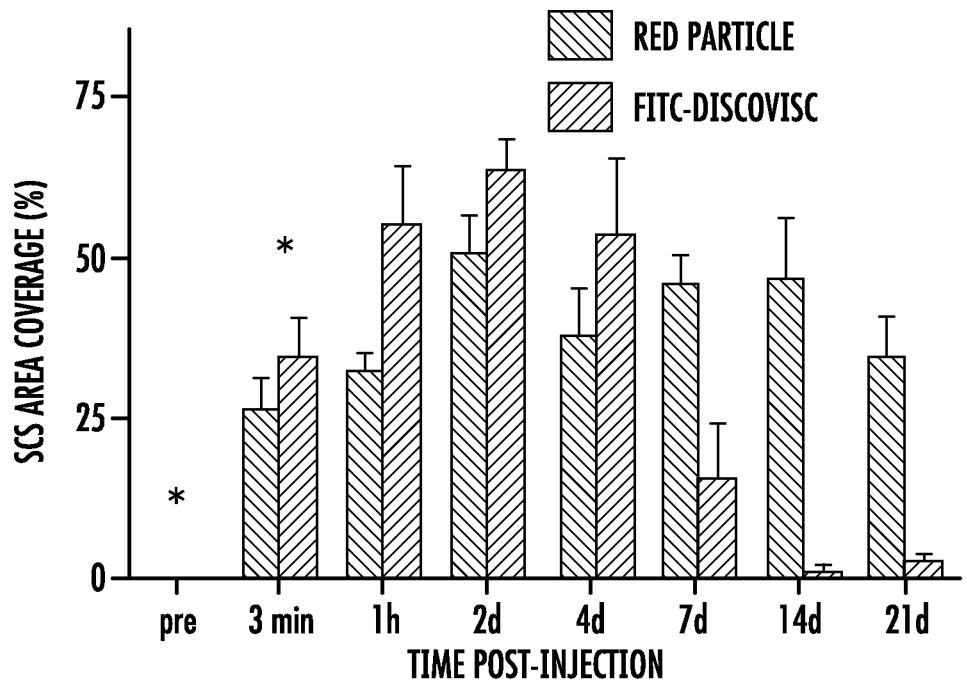
FIG. 4 depicts a quantification of area covered (mean±SEM, N=2-4) by red fluorescent particles and FITC-DisCoVisc® (Alcon, USA) in HBSS in several embodiments.

Considering all of the data depicted at FIG. 2, FIG. 3, and FIG. 4, the spread of particles immediately after injection appeared to depend on formulation composition, such that spreading went from smallest to largest with the following: FITC-CMC (8.5%)<FITC-DisCoVisc® (26%)<HBSS (30%).

At 14 days, the rank list for particle coverage for the tested excipients was FITC-CMC (20%)<HBSS (27%)<FITC-DisCoVisc® (46%). The maximum area coverage was achieved at 3 minutes when formulated only in HBSS, and at 2 days for FITC-CMC and FITC-DisCoVisc®. The particles injected with a low-viscosity formulation (i.e. HBSS only) did not experience a change in area coverage over time in this example. On the other hand, particles injected with viscous polymeric formulations (FITC-CMC and FITC-DisCoVisc®) experienced an increase in coverage of two-fold when comparing coverages at 3 minutes and 14 days post-injection. Thus, it was concluded that the viscous polymeric formulations prolonged particle transport time compared with the low-viscosity formulation. In this example, there was a strong association between transport time compared with viscosity. Initial viscosity of the formulation was a poor predictor of final spread of particles, possibly due to physical crosslinking of CMC that effectively increased viscosity after injection and thereby limited spreading.

Fluorescein in HBSS occupied 66% of the visible SCS, which was the largest area of all the fluorescent species injected. In comparison, peak FITC-CMC spreading was 20% of SCS area, and occurred at 2 days. Peak FITC-DisCoVisc® coverage was 63% and occurred at 2 days. Total clearance of the fluorescently-tagged formulation excipients occurred by 2 days for HBSS, 21 days for FITC-CMC, and 14 days for FITC-DisCoVisc®.

Co-localization of particles and the formulation excipients was seen at 3 minutes for HBSS, from 3 minutes up until 4 days for FITC-CMC, and 3 minutes for FITC-DisCoVisc®.

Figure 5:
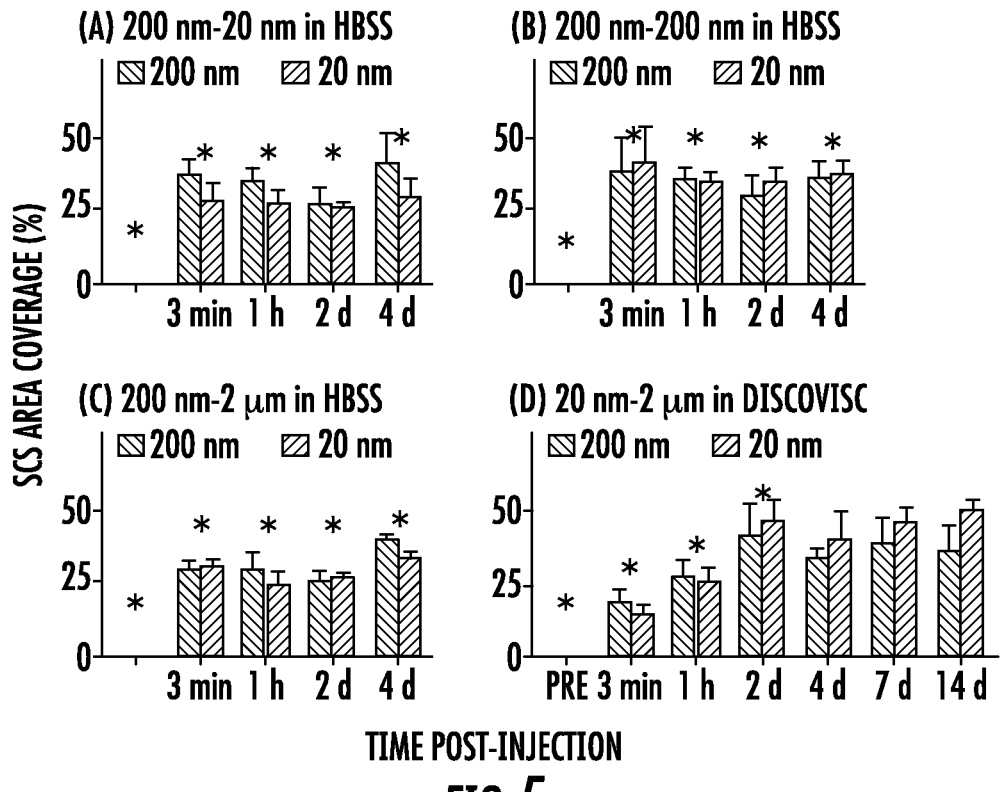
FIG. 5 depicts quantifications of areas covered (mean±SEM, N=3-4) after SCS injection with (A) 200 nm red- and 20 nm green-fluorescent particles in HBSS, (B) 200 nm red- and 200 nm green-fluorescent particles in HBSS, (C) 200 nm red- and 2 μm green-fluorescent particles in HBSS, and (D) 20 nm red- and 2 μm green-fluorescent particles in DisCoVisc® over time in vivo.

Effect of Particle Size on Particle Distribution Over Time after Injection into the SCS in Vivo:

To determine the effect of particle size on distribution, particles of different sizes (20 nm-2 µm) were suspended in HBSS and DisCoVisc® and co-injected into the rabbit SCS in vivo. Injections used pairwise combinations of red- and green-fluorescent particles of different sizes to determine whether the particles co-localized in the SCS. In all cases, the pairs of co-injected particles all co-localized for at least 4 days post-injection (FIG. 5). With all HBSS conditions, particle area did not change with time (p>0.06, 2-way ANOVA). For particles in DisCoVisc®, the particle area increased until 2 days for both the 20 nm and 2 µm particles.

Effect of Formulation on Distribution of Particles:

For the purposes of the kinetic studies of this example on the effects of polymeric formulation excipients in vivo, transport time was defined as the greater of (a) the time at which particle area stopped changing and (b) the time at which co-localization of particles and formulation excipients stopped. These two criteria demonstrated when the particle and formulation dissociated. The data showed that there was a strong association between transport time and viscosity of the liquid formulation, where increased viscosity facilitated longer transport time (i.e., for days after the injection). In contrast, viscosity of the formulation had a much weaker association with area coverage, probably because certain viscous formulations like CMC may have become physically crosslinked, effectively increasing viscosity after injection and thereby limiting spread.

Effect of Particle Size on Distribution of Particles:

Particles with diameters ranging from 2 nm to 2 µm co-localized within the SCS independent of particle size in this example. Furthermore, the size of the particles did not influence transport time. Particles of different sizes may be preferred for different applications, such as micron-scale particles to serve as slow-releasing drug delivery systems, nanoscale virus particles as gene delivery vectors, and micron-sized cells as cell-based therapies. The particles spanning two orders of magnitude in size distributed on the SCS to a similar extent with similar kinetics, which should simplify design of particle delivery to the SCS. Other particle parameters, however, may also play a role, such as particle density, shape, surface properties and composition, or a combination thereof.

All reagents and chemicals were purchased from Sigma-Aldrich (St. Louis, Mo.) unless otherwise specified. Red-fluorescent polystyrene particles (Excitation: 580 nm; Emission: 605 nm) and green-fluorescent polystyrene particles (Excitation: 505 nm; Emission: 515 nm) with diameters ranging from 0.02-2 µm were purchased from Life Technologies (Fluosphere, Carlsbad, Calif.). Eyes of pigmented Silver Fox and American Blue rabbits (Broad River Pastures, Elberton, Ga.) and albino New Zealand White rabbits (Pel Freeze, Rogers, Ark.) were obtained within 1 day after euthanasia and stored in a −80° C. freezer until use. All in vivo experiments were carried out in albino New Zealand White rabbits (Charles River Laboratories, Wilmington, Mass.). Four replicates per experimental group were performed unless otherwise specified.

Ex Vivo Injection Procedure:

Extraocular tissues were carefully removed from the rabbit ocular globe. To simulate a physiological intraocular pressure (IOP) of 10-12 mmHg, a water column was raised to ~14 cm and connected to the eye via a 25-gauge needle penetrated through the optic nerve. A microneedle (750 µm in length, 33-gauge; Clearside Biomedical, Alpharetta, Ga.) attached to a 250 µL glass chromatography syringe (National Scientific, Rockwood, Tenn.) was used to make injections. Injections were performed 3 mm posterior to the limbus at the 12 o'clock position (superior) to be as far as possible from anatomical barriers created by the long posterior ciliary artery that impede circumferential flow.

Depending on the experimental condition, each injection consisted of 25 to 150 µL of 0.5% (w/v) red-fluorescent particles (0.2 µm diameter; Excitation: 580 nm; Emission: 605 nm) and 0.025% (w/v) fluorescein suspended in Hank's Balanced Salt Solution (HBSS; Gibco, Life Technologies). After each injection, the needle was held in place for 1 minute to minimize reflux. The eye was then frozen via submersion in 100% ethanol chilled over dry ice 3 minutes post-injection depending on experimental condition.

Flat Mount to Characterize 2D Circumferential Spread:

After SCS injection and freezing, eyes were prepared to assess the 2D spread of particles and fluorescein. The frozen eye was sliced open from the limbus to the posterior pole to generate eight approximately equidistant scleral flaps. The resulting scleral flaps were splayed open and the frozen vitreous humor, lens, and aqueous humor were removed.

A digital SLR camera (Canon 60D, Canon, Melville, N.Y.) with a 100 mm lens (Canon) was used to acquire brightfield and fluorescence images. Camera parameters were held constant at a shutter speed of 1/15 s and an aperture of F/2.8. To acquire the area of fluorescein spread, a green optical band-pass filter (520±10 nm; Edmunds Optics, Barrington, N.J.) was placed on the lens, and the sample was illuminated by a lamp with the violet setting of a multicolor LED bulb (S Series RGB MR16/E26, HitLights, Baton Rouge, La.). To visualize the location of the red-fluorescent particles, a red filter (610±10 nm; Edmunds Optics) was placed on the lens, and the sample was illuminated with the same lamp switched to green light. The area of green and red fluorescence that was above threshold was calculated for each eye using ImageJ (National Institutes of Health, Bethesda, Md.). Thresholding was set manually based on visual inspection of background signal.

Fluorescent Tagging of Excipient Formulation:

To visualize the spread of polymer formulation excipients, polysaccharides that have been shown to significantly influence spread of particles within the SCS were fluorescently labeled using known methods. Carboxymethyl cellulose (CMC; 700 kDa high viscosity, Sigma-Aldrich) has been shown to impede spread of particles, allowing for localized delivery of particles that stay near the injection site. On the other hand, DisCoVisc® (1.65 MDa hyaluronic acid; Alcon Laboratories, Fort Worth, Tex.) and hyaluronic acid have been shown to promote spread up to 100% of SCS area by a slow process after injection.

To label CMC, 250 mg of CMC and 10 mg of fluorescein isothiocyanate (FITC) were added to 25 mL of 0.1 M NaOH in DI water. The solution was mixed in the dark at room temperature (22° C.) for 4.5 days. The solution was then transferred into a dialysis tube (30 kDa cutoff, Spectra/Por, Spectrum Laboratories, Rancho Dominguez, Calif.) in a DI water bath. The water bath was changed daily for 5 days to remove unreacted FITC. The contents of the dialysis tube were transferred into a 50 mL centrifuge tube and frozen prior to vacuum drying. Care was taken to minimize light exposure at all steps to minimize photobleaching. A similar procedure was performed with DisCoVisc® (1.65 MDa hyaluronic acid); 500 µL of DisCoVisc® and 1 mg of FITC were added to 2.5 mL of 0.1 NaOH. The other methods were the same as those used for FITC labeling of CMC.

In Vivo SCS Injections and Image Acquisition:

Albino rabbits were anesthetized with isoflurane and treated with proparacaine eye drops (Bausch & Lomb, Rochester, N.Y.). All injections were 50 µL in volume and performed 3 mm posterior to the limbus at the supranasal quadrant (4 mm nasal to the edge of the superior rectus extraocular muscle).

To determine the effect of polymeric formulation on particle spread, the following injections (N=4 eyes per group) were performed: [i] 50 µL of 2% (w/v) red-fluorescent particles (0.2 µm diameter) and 0.025% fluorescein (332 Da) in HBSS; [ii] 50 µL of 2% (w/v) red-fluorescent particles (0.2 µm diameter) and 5% FITC-CMC (~700 kDa) in HBSS; [iii] 50 µL of 2% (w/v) red-fluorescent particles (0.2 µm diameter) and 1×FITC-DisCoVisc® (HA ~1.65 MDa and chondroitin sulfate ~22.5 kDa) re-constituted in HBSS.

To determine if particles ranging from 0.02 µm to 2 µm co-localized, the following injections (N=4 eyes per group) were performed: [i] 50 µL of 1% (w/v) red-fluorescent particles (0.2 µm diameter) and 1% (w/v) green-fluorescent particles (0.02 µm in diameter) suspended in HBSS; [ii] 50 µL of 1% (w/v) red-fluorescent particles (0.2 µm diameter) and 1% (w/v) green-fluorescent particles (0.2 µm diameter) suspended in HBSS; [iii] 50 µL of 1% (w/v) red-fluorescent particles (0.2 µm diameter) and 1% (w/v) green-fluorescent particles (2 µm diameter) suspended in HBSS; and [iv] 50 µL of 1% (w/v) red-fluorescent particles (0.02 µm diameter) and 1% (w/v) red-fluorescent particles (2 µm diameter) suspended in unlabeled DisCoVisc®.

At predetermined time points, the animals were imaged with a modified RetCam II system (Clarity Medical Systems, Pleasanton, Calif.). Prior to imaging, tropicamide (Akorn Pharmaceuticals, Lake Forest, Ill.), phenylephrine (Akorn Pharmaceuticals), and proparacaine (Akorn Pharmaceuticals) eye drops were given. The built-in fluorescein attachment was used to capture green fluorescence. For the red fluorescence, green light was generated by placing a 575±50 nm bandpass filter (Edmunds Optics) in line with the fiber optic line. A red-emission filter (610±10 nm, Omega Optical, Brattleboro, Vt.) was placed over the camera to capture red fluorescence. Animals were euthanized with an injection of pentobarbital through the ear vein at the end of the experiment.

Post-processing of the RetCam images was used to generate a collage for each imaging condition, since the camera did not have built-in image stitching algorithms. Co-localization was determined using a previously described method (McDonald and Dunn, 2013). Briefly, the 2D correlation coefficient of the red- and green-fluorescent images was calculated, and compared against the 2D correlation of 100 randomly assigned image pairs using a one-sided unpaired t-test. A low p-value ($\alpha$<0.05) indicated statistically significant co-localization greater than chance, and a high p-value ($\alpha$>0.05) indicated no significant co-localization.

Image analysis was performed using Matlab and ImageJ. Statistical analysis was performed using Prism (Graphpad, La Jolla, Calif.). Values are presented as the mean±standard error of the mean (SEM), unless otherwise specified. Two-way ANOVA and Student's t-test analyses ($\alpha$=0.05) were performed to determine statistical significance.

Example 2—Evaluation of SCS Thickness

The tests of this example examined the effects of injection volume and liquid formulation on the thickness and closure kinetics of the SCS following microneedle injection. It was discovered that the SCS was spread to a roughly constant thickness, independent of injection volume. This unexpected observation was made in the rabbit eye ex vivo using two different measurement methods: 3D cryo-reconstruction and U/S B-scan imaging. Injection of an increasing volume of fluid into the SCS could be accommodated by an increase in SCS thickness, SCS area, or a combination of both. The data of this example indicate that the SCS readily expands to a certain thickness, after which additional fluid fills the SCS by expanding the SCS area containing fluid without expanding the SCS thickness further. This explanation was supported by demonstration that the area of fluid in the SCS increased in direct proportion with the volume injected.

Specifically, microneedle injections containing 25-150 µL of Hank's Balanced Salt Solution (HBSS) were performed in a rabbit SCS ex vivo, and distribution of SCS thickness was measured by ultrasonography and 3D cryo-reconstruction. Microneedle injections were performed in a rabbit SCS in vivo using [1] HBSS; [2] DisCoVisc® (Alcon, USA); and [3] 1-5% carboxymethyl cellulose (CMC) in HBSS. Ultrasonography was used to track SCS thickness over time.

Increasing HBSS injection volume increased the area of expanded SCS, but did not increase SCS thickness ex vivo. With SCS injections in vivo, the SCS initially expanded to thicknesses of 0.43±0.06 mm with HBSS, 1.5±0.4 mm with DisCoVisc®, and 0.69-2.1 mm with 1-5% CMC. After injection with HBSS, DisCoVisc® and 1 CMC solution, the SCS collapsed to baseline with time constants of 19 minutes, 6 hours and 2.4 days, respectively. In contrast, injections with 3-5 CMC solution resulted in SCS expansion to 2.3-2.8 mm over the course of 2.8-9.1 hours, after which the SCS collapsed to baseline with time constants of 4.5-9.2 days.

When the SCS was fully collapsed, the force required to expand the thickness of the SCS was less than the force to flow liquid through the adjacent collapsed SCS to expand the area. As more fluid was forced into the SCS, the SCS thickness continued to expand until the force required for further expansion of thickness of SCS exceeded the force required to flow fluid out into adjacent SCS. This switch likely occurred due to two factors: (i) as the SCS thickness increases, the force required to further increase thickness escalates, and (ii) as the SCS thickness increases, the viscous forces to flow into adjacent SCS decrease because flow through wider channels exhibits less resistance to flow.

Figure 6:
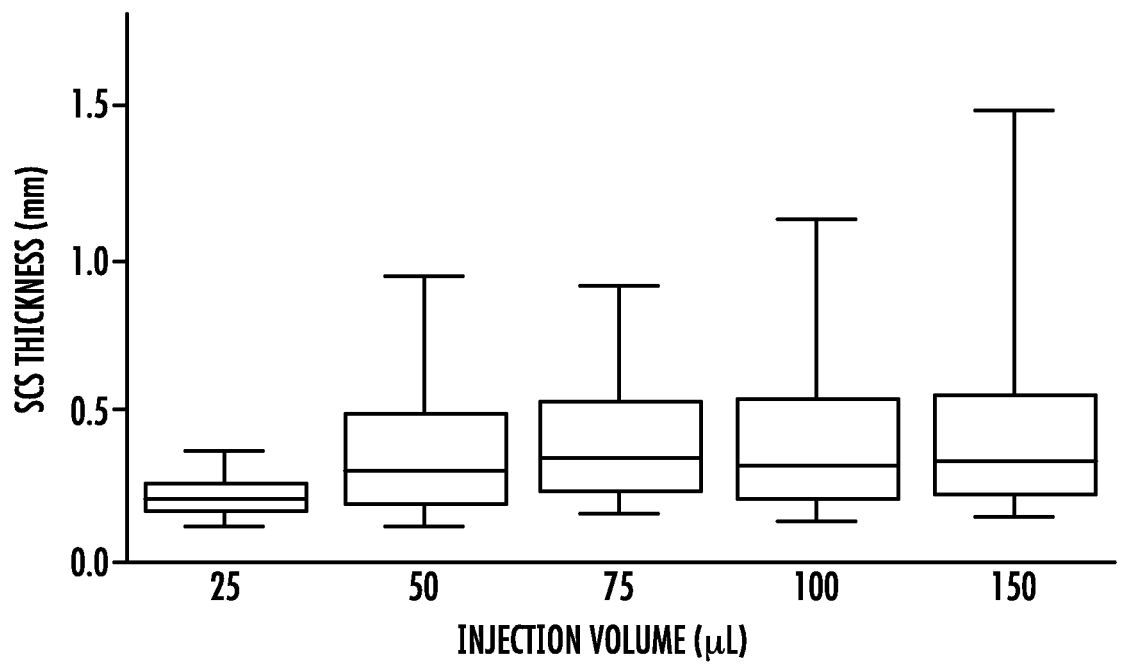
FIG. 6 depicts the relationship between SCS thickness and injection volume of one embodiment of a liquid.
Figure 7:
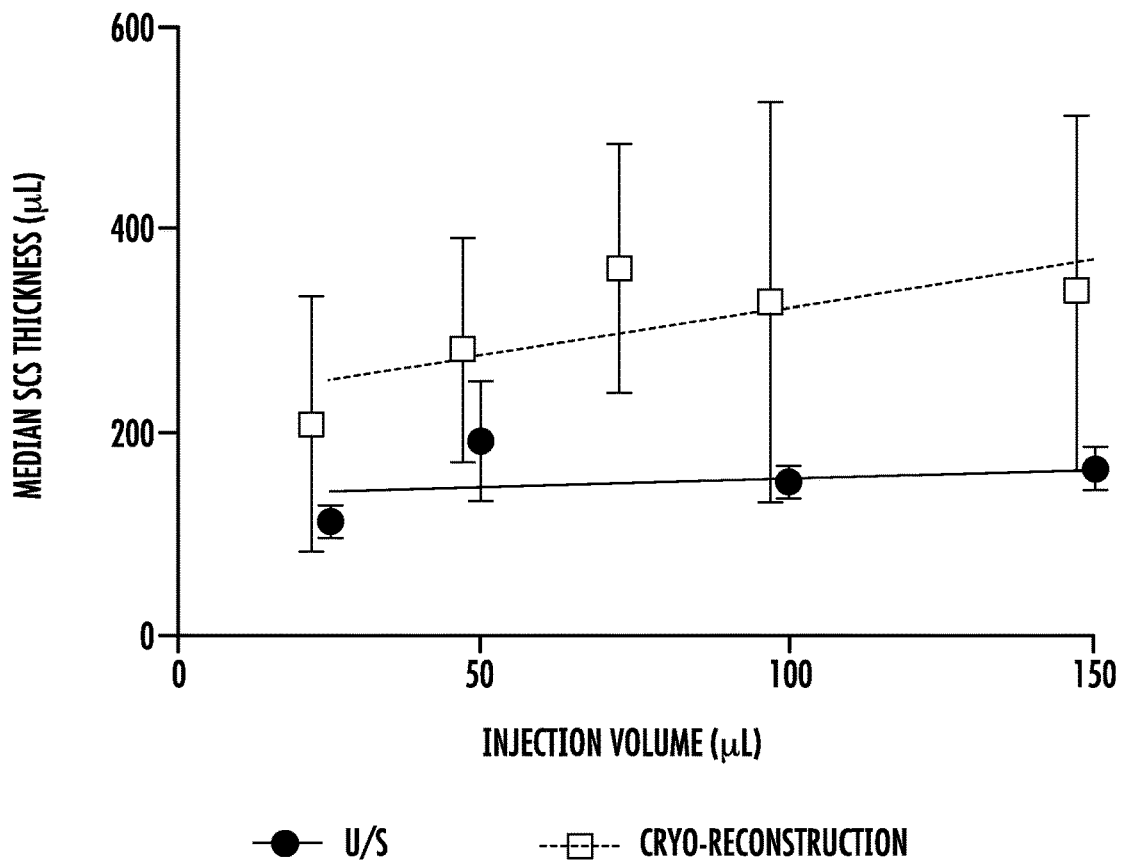
FIG. 7 depicts a quantification of median SCS thickness±SEM of certain some embodiments based on ultrasound (U/S) and cryo-reconstruction methods (N=3-7 replicates); the lines indicate best fits by linear regression.

When injecting HBSS (with a low viscosity comparable to water) into SCS of the rabbit, the force balance switched when the SCS was expanded to 150-350 µm in the rabbit eye ex vivo, and to 400-500 µm in the rabbit eye in vivo; this was called this thickness the "equilibrium thickness," because it represented the thickness when the force needed to expand thickness equaled the forces needed to expand area of the SCS. In this way, SCS readily expanded to the equilibrium thickness until further increasing SCS thickness required more force than increasing SCS area. A distribution of equilibrium thicknesses was expected, as seen at FIG. 6 and FIG. 7, due to variation in the mechanical properties of the SCS.

When injecting DisCoVisc® or CMC, which have higher viscosity than HBSS (e.g., >170,000 cP for 1.7% CMC (700 kDa) in HBSS), the force balance was altered. The viscous forces of the formulation were increased while the resistive biomechanical forces of the tissue were unchanged. Thus, the equilibrium thickness increased and expansion of SCS area required greater force.

In the case of 3% CMC and 5% CMC solutions, there was likely an additional force in play. After the fluid had been injected and the SCS expanded to its equilibrium value, diffusive forces pulling fluid into the CMC gel formed in the SCS cause the gel to expand. Because the gel has physical crosslinks, it could not easily flow through SCS to expand area, but instead expanded in place, which primarily expanded SCS thickness. In this case, a new force balance was set up between the expansive swelling force of the gel and the resistive biomechanical forces of the ocular tissue. This resulted in a new equilibrium thickness based on the balance of these two forces.

All reagents and chemicals were purchased from Sigma-Aldrich (St. Louis, Mo.) unless otherwise specified. Red fluorescent polystyrene particles (excitation: 580 nm; emission: 605 nm) with diameters of 200 nm were purchased from Life Technologies (Fluospheres, Carlsbad, Calif.). Eyes of pigmented Silver Fox and American Blue rabbits (Broad River Pastures, Elberton, Ga.) and albino New Zealand White rabbits (Pel Freeze, Rogers, Ark.) were obtained within 1 day after sacrifice, and stored in a −80° C. freezer immediately upon arrival. Pigmented eyes were used to prevent vitreous glow. There was no gross anatomical difference among the eyes beyond eye size. All in vivo experiments were carried out in albino New Zealand White rabbits (Charles River Laboratories, Wilmington, Mass.). Four replicates per group were performed unless otherwise specified.

Ex Vivo Injection Procedure:

Using a rabbit eye pressurized to physiological intraocular pressure (TOP), a 750 µm-long, 33-gauge hollow microneedle attached to a syringe was used to make injections of red-fluorescent particles suspended in 25-150 µL Hank's Balanced Salt Solution into the SCS.

Effect of Injection Volume on SCS Thickness:

Microneedle injections of 25-150 µL containing red-fluorescent particles were performed in pigmented rabbit eyes, which were frozen 3 minutes post-injection, and prepared for cryo-sectioning. Using a digital camera, one red-fluorescent image of the cryo-block of tissue was obtained every 300 µm by slicing the sample with the cryostat. Image stacks consisting of red fluorescence images were analyzed to determine SCS thickness. 2D mapping of the spread of particles in the SCS after injection of different volumes of fluid indicated that the area of spreading increased with injection volume.

Quantification of the SCS thickness throughout the area of spreading produced histograms of the SCS thickness for each injection volume. Sites where SCS thickness was less than 25 µm were considered to have "unopened" SCS and were therefore not included in the analysis. All particle thickness histograms showed a characteristic spike at ~160 µm (i.e., the average mode value among the histograms collected at all conditions was 160±25 (mean±SEM)), and there were very few portions of the SCS open to smaller thicknesses. This peak value of SCS thickness did not significantly change as a function of injection volume (p=0.43, one-way ANOVA). This indicated that if the SCS was opened up, it readily expanded to a thickness of at least ~160 µm.

The median value of SCS thickness was found to be 330±30 µm, which was significantly different from the mode value (p<0.001, unpaired t-test) indicating few points where the thickness was less than 150 µm. The median SCS thickness was independent of injection volume (p=0.15, F test for zero slope), as shown at FIG. 6. In FIG. 6, each box and whiskers represent the $5^{th}$, $25^{th}$, $50^{th}$ (median), $75^{th}$, and $95^{th}$ percentile of SCS thickness after injection (N=3-7 replicates per condition). This finding is notable, because injection of larger volumes of fluid can increase the area of fluid spread in the SCS and/or the thickness of the SCS. These data indicate that the SCS expands to a maximum thickness, and that injection of additional fluid increases area of spreading in direct proportion to the volume injected. To further test this hypothesis, the area of spreading versus injection volume was plotted, and the plot revealed that these parameters increased in direct proportion to each other.

The mean values of SCS thickness were found to be 340±40 µm among all the conditions tested in this example. The mean values had a slight dependence on injection volume (p=0.04, F test for zero slope). The $5^{th}$, $25^{th}$, median, and $75^{th}$ percentile SCS thickness was approximately constant for injection volumes greater than 25 but the $95^{th}$ percentile increased with injection volume. The fact that there was a spread of SCS thicknesses to values up to a few-fold larger than the median value indicated that SCS thickness can be spread well beyond ~300 µm in some cases. These sites of greater SCS thickness occurred in patches, according to the 2D thickness maps, that were often located near the site of injection.

A high-frequency ultrasound (U/S) probe (UBM Plus, Accutome, Malvern, Pa.) was used to determine SCS thickness by generating 2D cross-sectional images of the SCS in rabbit eyes ex vivo after injecting volumes ranging from 25 to 150 µL. Three minutes after injection, the U/S probe was used to acquire eight sagittal views around the eye. Post-processing of the U/S B scans was performed to find the thickness from the outer sclera to the inner retina at 1, 5, and 9 mm posterior to the scleral spur.

To validate the SCS thickness measurements calculated by the cryo-reconstruction method, additional experiments were conducted to measure SCS thickness by ultrasound B-scan in the rabbit eye ex vivo. As shown at FIG. 7, this U/S measurement yielded a median SCS thickness of 160±20 µm, which was independent of injection volume (p=0.67, F test for zero slope) and was about half the value obtained by the cryo-reconstruction method (i.e., 330±30 µm). However, the two methods both showed that SCS thickness values were independent of injection volume and had a median value between 150-350 µm. Since the eyes used in the U/S measurement were at room temperature and measured in real time shortly after injection, whereas the eyes used in 3D cryo-reconstruction were frozen shortly after injection and measured later while still in the frozen state, the observed differences in thickness may have been due to differences in timing, temperature, solid vs. liquid state tissue fluids or artifacts due to freezing. Furthermore, the U/S measurement was not able to assess the SCS thickness at the posterior pole, which may have biased the results.

Mechanical Testing of Sclera-Choroid Attachments:

After microneedle injection of 100 µL HBSS into the SCS of albino rabbit eyes ex vivo, two sagittal strips—one with no injection and one with SCS injection—from the same eye were each mounted on a force displacement station that peeled the sclera from the choroid to determine the average force to separate the tissues.

The mechanical testing of sclera-choroid attachments was used to investigate further why median SCS thickness was constant over the range of injection volumes studied. It is believed that the presence of lamellae that attach the sclera to the choroid might explain this constant thickness, as they may limit expansion of the SCS beyond a certain thickness.

Figure 8:
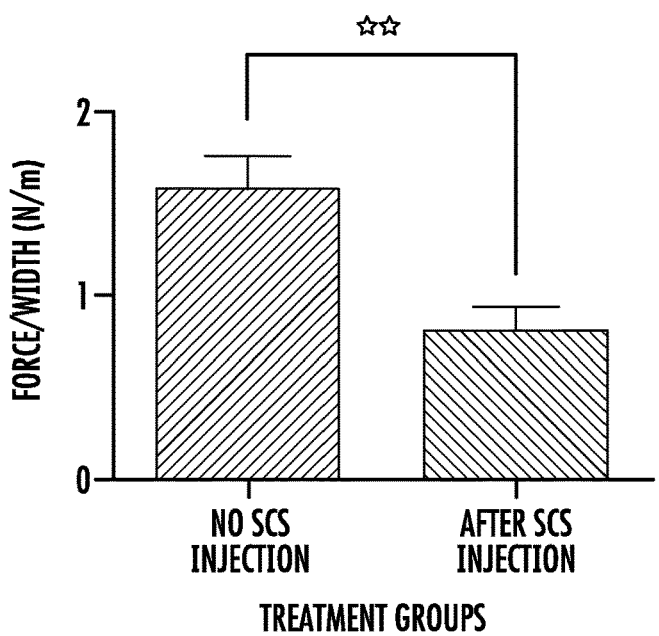
FIG. 8 depicts the Mean±SEM of the force to separate sclera from choroid per width of the tissue strip.

A peel test was performed on scleral/chorioretinal strips from rabbit eyes that had either received or not received a SCS injection of HBSS ex vivo. The test was a modified ATSM 1876 peel test. It was found that eyes with previous injection in the SCS required only 51% of the force to separate the sclera from the choroid compared with eyes having no SCS injection (p<0.005, unpaired t-test), as depicted at FIG. 8.

This suggests that the process of SCS injection weakens the adhesion strength between the sclera and choroid, possibly due to reorganizing, weakening, breaking, or otherwise altering fibers adhering the sclera to the choroid. Since the force to separate the tissue does not become zero after injection, adhesive forces between the sclera and choroid, possibly involving connective fibers, may play a role in limiting SCS expansion.

Also collected and examined were histological sections for anatomical structures within the SCS of rabbit eyes that had either received or not received a SCS injection of HBSS in the live rabbit. With no injection, the sclera and choroid appeared to be tightly apposed. After injection, the sclera and choroid appeared to be no longer tightly adhered, even more than one month after injection in vivo. Furthermore, there was evidence of structures that appear to be fibrils connecting the sclera and choroid.

Effect of Liquid Formulation on SCS Thickness and Collapse Time:

It was discovered that liquid formulation, including fluid viscosity, had a significant effect on SCS thickness. While HBSS spread over large areas of the SCS, DisCoVisc® and CMC solutions were largely retained near the site of injection initially, probably due to their high viscosity. This likely was due to the viscous forces resisting spread of the injected fluid in the SCS leading to the fluid further expanding the SCS near the site of injection in order to accommodate the injected fluid volume. In some cases (i.e., 3% CMC and 5% CMC solutions), SCS thickness continued to expand for hours after the injection, probably due to the diffusion of water into the hydrogel, which resulted in swelling it.

At later times, SCS thickness decreased and ultimately returned to baseline within hours for HBSS and within days to weeks for the viscous solutions. These slow kinetics may have been controlled by clearance of the polymer components of the hydrogels from the SCS, which was significantly slower for CMC, which forms a physically cross-linked gel.

The formulations also contained particles, which were not expected to change the clearance properties of the polymeric formulation (Gu B. et al., *Invest Ophthalmol Vis Sci* 2015; 56:3623-3634; and Chiang B. et al., *Exp Eye Res* 2016; 153:101-109).

Figure 9:
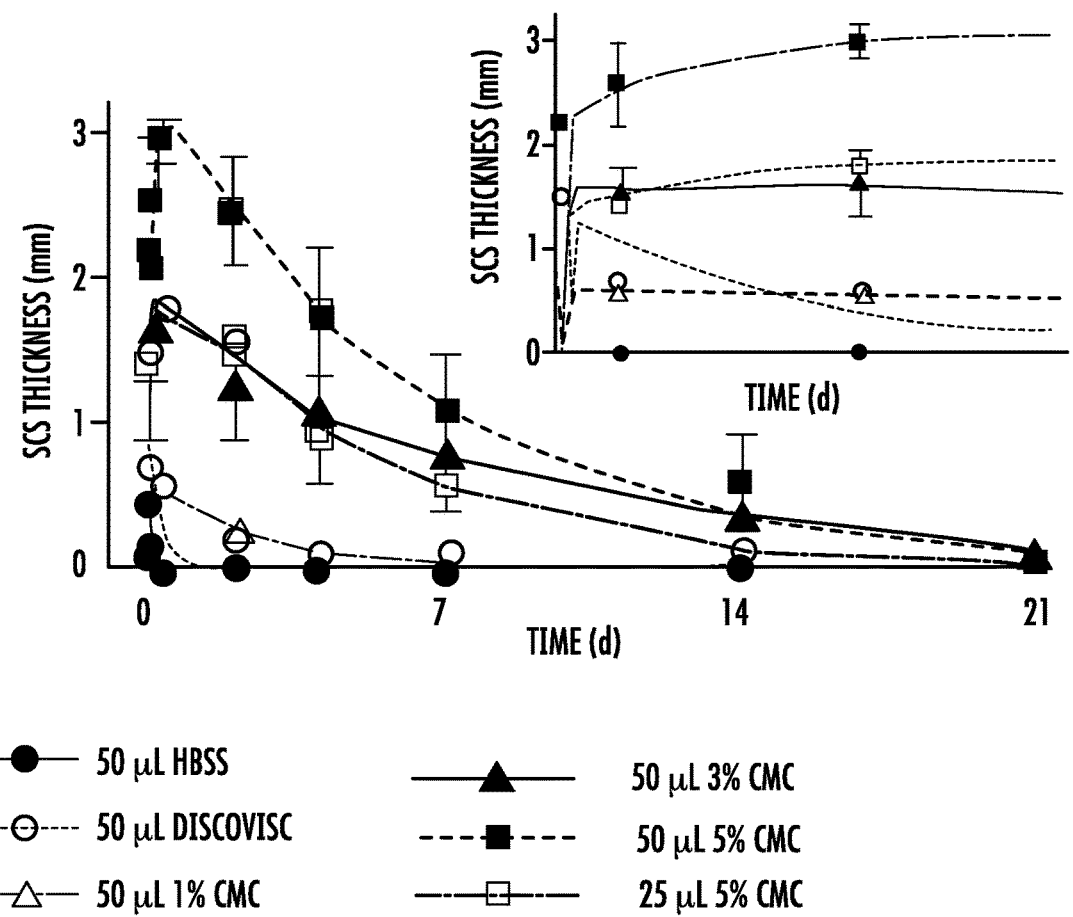
FIG. 9 depicts the time course of SCS thickness after injection with embodiments of six liquid formulations (the inset depicts the data collected during the first 24 hours).

After injection of a formulation into the SCS of an anesthetized rabbit, U/S B-scan was used to determine SCS thickness at multiple locations over time, from which the rate of SCS collapse was calculated, as shown at FIG. 9. In companion experiments, the approximate clearance rate of injected fluorescent material from the SCS was found by taking fluorescence fundus images in the rabbit eye in vivo over time until fluorescence was no longer visible.

Solutions of carboxymethyl cellulose (CMC) at different concentrations in HBSS and the commercial viscoelastic product, DisCoVisc® (which contains 1.65 MDa hyaluronic acid) were chosen as liquid formulations for this study, because these liquid formulations were previously shown to distribute differently in the SCS, compared with HBSS (Kim Y. C. et al., *Eur J Pharm Biopharm* 2015; 95:398-406).

Figure 10:
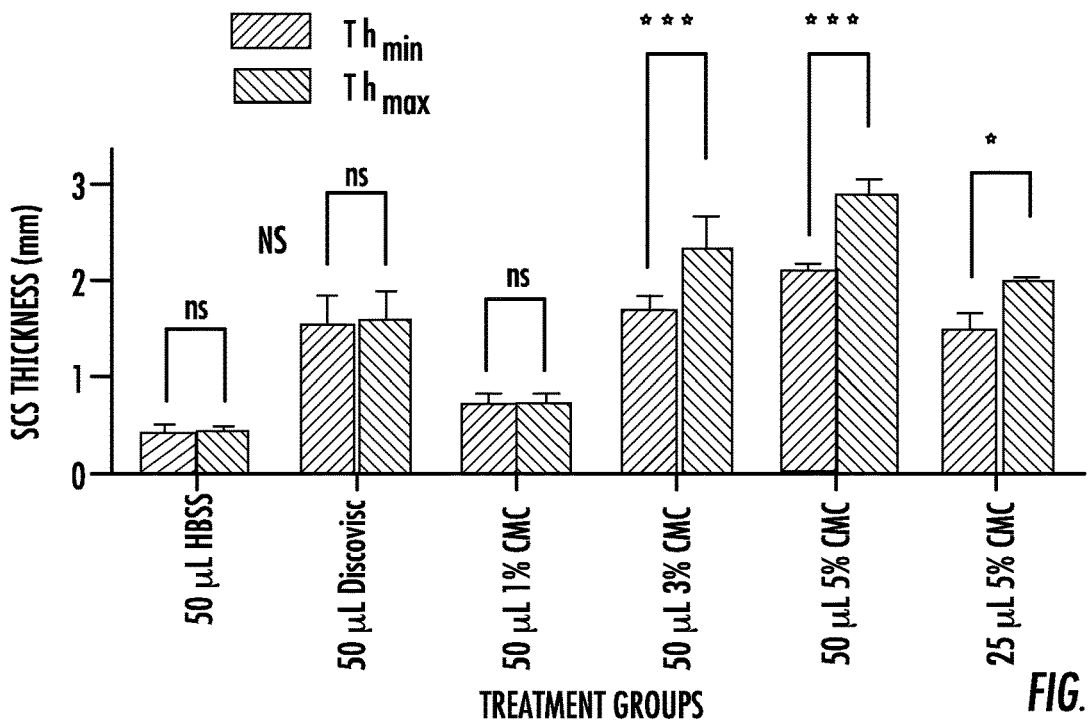
FIG. 10 depicts SCS thickness measured immediately post-injection and the maximum SCS thickness achieved upon injection of embodiments of liquid formulations.

The initial SCS thickness at the injection site varied with the choice of liquid formulation from 0.43±0.06 mm with HBSS to 2.1±0.1 mm with 5% CMC in HBSS, as depicted at FIG. 10. The value for HBSS found in the living rabbit eye was larger than what was found above in the rabbit eye ex vivo. This could have been due to the fact that the in vivo measurement was made at the injection site, which was the site of maximum SCS thickness, whereas the ex vivo measurement was reported as the average SCS thickness through the expanded SCS. The use of DisCoVisc®, which had previously been reported to initially remain near the site of injection in the SCS (Kim Y. C. et al., *Eur J Pharm Biopharm* 2015; 95:398-406), had a SCS thickness of 1.5±0.4 mm, which was significantly larger than the value for HBSS (p<0.01, Sidak's multiple comparison test). SCS injection of solutions containing 1%, 3% and 5% CMC in HBSS (viscous solutions that have also been reported to localize at the injection site[20]) had initial SCS thicknesses of 0.7±0.1 mm, 1.6±0.2 mm and 2.1±0.1 mm, respectively (see FIG. 10). These data indicate that changing the formulation (to increase viscosity) had a larger effect on SCS thickness than increasing injection volume for a given formulation.

Also monitored was SCS thickness over time at eight positions around the globe for all the formulations tested. After injection of HBSS, the SCS thickness over the injection site achieved its peak value immediately after injection, and then decreased according to a roughly first-order exponential decay, i.e., there was no significant difference between SCS thickness immediately post-injection ($\theta_0$) and the maximal SCS thickness ($\theta_{max}$) (p>0.99, Sidak's multiple comparison test, see FIG. 10). Measurements at other locations around the globe behaved similarly.

There was also no difference between initial and maximal SCS thickness over the injection site for DisCoVisc® and 1% CMC (p≥0.97, Sidak's multiple comparison test). However, the SCS thickness measured at the other sites behaved differently. With DisCoVisc®, the decrease in SCS thickness at the injection site over time was accompanied by a concomitant increase in SCS thickness at adjacent sites in the SCS. By day 2, the SCS thickness throughout the entire eye had returned to baseline. In contrast, 1% CMC only expanded the SCS at or near the injection site for the entire time course. Since DisCoVisc® is known to facilitate the distribution of particles throughout the SCS, and CMC was able to localize particles near the injection site, it is believed that the expansion of a region of SCS was necessary for particle deposition in that region.

With 3% CMC and 5% CMC solutions, $\theta_0$ over the injection site was different than $\theta_{max}$ (p<0.01, 2-way ANOVA) because the SCS thickness initially increased over the course of hours after the injection. This expansion of the SCS could be explained by an osmotic and hydration effect of the CMC within the SCS, which could draw in water from the surrounding tissue to dilute the CMC and cause swelling of the gel. Besides the swelling at the site of injection, the behavior of the SCS thickness at other positions was similar to those found with 1% CMC.

Figure 11:
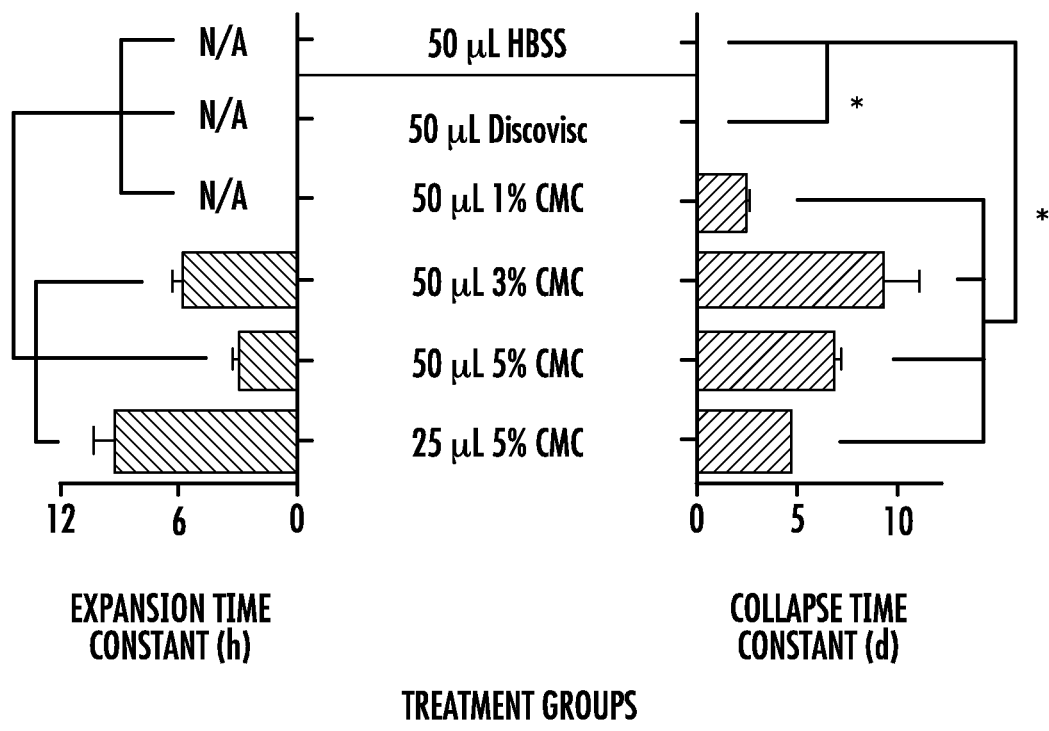
FIG. 11 depicts the time constants associated with SCS expansion and collapse for different embodiments of liquid formulations.

To describe the timecourse of SCS thickness changes after injection over the injection site, a 2' order exponential equation was used that could account for both the observed expansion and collapse of the SCS:

$$\theta(t) = -Ae^{-t/\tau_{exp}} + Be^{-t/\tau_{col}}, \qquad \text{Eq. 1}$$

wherein t is the time post-injection, $\theta(t)$ is the SCS thickness as a function of time, A and B are thickness constants, $\tau_{exp}$ is the expansion time constant, and $\tau_{col}$ is the collapse time constant (FIG. 11). This equation described the data from all the liquid formulations well (Pearson coefficient $r^2$>0.76).

Using this equation, the characteristic times associated with each of the liquid formulations were calculated. As expected, the liquid formulations that did not cause further expansion of the SCS after injection (i.e., HBSS, DisCoVisc®, and 1% CMC), the calculated $\tau_{exp}$ values were all on the order of seconds (see FIG. 11, left). In contrast, $\tau_{exp}$ values for the 3% CMC and 5% CMC liquid formulations ranged from 2.8 to 9.1 h, and there was no significant difference among these $\tau_{exp}$ values (p=0.77, F test).

There were significant differences in $\tau_{col}$ values among the liquid formulations tested (see FIG. 11, right). With HBSS as the liquid formulation, $\tau_{col}$ was 19±3 min. With the DisCoVisc® liquid formulation, $\tau_{col}$ was 6±2 h, which was significantly longer than the HBSS value (p<0.005, F test). With all of the CMC liquid formulations, $\tau_{col}$ ranged from 2.4-9.2 days, which were also longer than HBSS (p<0.0001, F test) but not different from each other (p=0.47, F test). It is notable that collapse of SCS containing 1% CMC solution (that did not swell after injection) and SCS containing 5% CMC solution (which did swell after injection) had comparable $\tau_{col}$ values, which suggests that dissociation of the crosslinks found in CMC gels may be the rate limiting step to CMC clearance from the SCS resulting in collapse.

Figure 12:
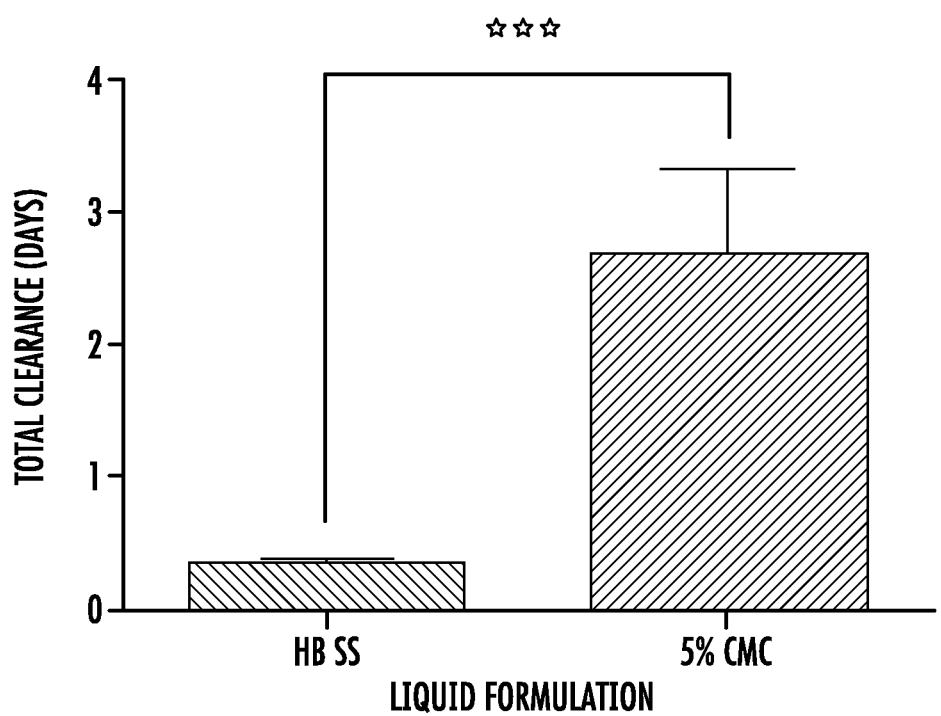
FIG. 12 depicts the total clearance time of fluorescein from the SCS after injection in HBSS or 5 CMC solution.

Effect of Liquid Formulation on Clearance of Fluorescent Molecules from the SCS:

Also investigated was the effect of liquid formulation viscosity on the timescale of clearance of fluorescein from the SCS. Using fundus microscopy, the time it took for there to be no visual evidence of fluorescein in the SCS was identified. Total clearance of fluorescein injected into the SCS in HBSS was 0.33±0.05 d, which was significantly faster than the clearance of fluorescein injected in 5% CMC solution, which was 2.7±0.7 d (p<0.0005, unpaired t-test, FIG. 12). This was likely due to the long-lived presence of viscous CMC gel in the SCS (as evidenced by the SCS remaining open for many days), which can slow diffusion of fluorescein out of the SCS.

Example 3—Clearance Kinetics and Routes of Clearance of Molecules from the SCS

The tests of this example determined the clearance kinetics and routes of clearance of molecules from the SCS of live New Zealand White rabbits. The molecules were injected into the SCS of live rabbits using a microneedle. As explained in this example, it was determined that complete collapse of SCS occurred by 40 minutes, and, during the first hour post-injection, approximately half of injected fluorescein was cleared from the ocular globe, with approximately half still remaining. The remaining fluorescein was not visible by 12 hours post-injection.

Dominant Route of Clearance from the SCS:

Since the time constants of molecule clearance from the eye and the time constant of trans-scleral clearance were of the same order of magnitude of hours (with intravascular clearance being significantly faster), the model of this example suggested that trans-scleral diffusion was the dominant route of clearance. The model generated a clearance time constant similar to the time constant of 4.3 hours that was determined based on fundus imaging.

Guided by experimental data in the context of model predictions, characteristic times of key transport phenomena following SCS injection are summarized at Table 1.

TABLE 1

Characteristic times of transport phenomena in the eye

| Characteristic time (order of magnitude) | Transport phenomena in eye |
| --- | --- |
| 1 minutes | SCS loaded with fluid and molecules during injection |
| 10 minutes | Fluid and molecules cleared from SCS by convection through leakage pathways<br>Remaining molecules transported into choroid and sclera<br>SCS collapses<br>IOP drops to baseline |
| 1 hour | Molecules cleared by choroidal blood flow |
| 1-10 hours | Molecules cleared from sclera by diffusion and convection |

Effect of Molecular Size on Residence Time:

It was found experimentally and computationally that increasing molecular radius had a significant effect on clearance time. Fluorescein (~1 nm in diameter (Ambati J. et al. *Invest Ophthalmol Vis Sci* 2000; 41:1181-1185)) was cleared by 24 hours, while 2 MDa FITC-dextran (~50 nm in diameter (Kano M. R. et al., *Proc Natl Acad Sci USA* 2007; 104:3460-3465.) was not fully cleared until 21 days. The prolonged residence time did not increase linearly with molecular mass, but was significantly longer above a threshold of ~$10^6$ Da. The difficulty for very large macromolecules to pass through fenestrae of the choriocapillaris and through extracellular matrix of sclera is the likely explanation for this behavior.

As described in this example, the bulk of clearance appeared to occur via diffusion across sclera, as well as through choroid into choriocapillaries. The physiological upper limit of pore size of the choriocapillaris is estimated to be ~6 nm (Sarin H. et al. *J Angiogenes Res* 2010; 2:14). Thus, the hydrodynamic radius of 2 MDa FITC dextran is much larger than choriocapillaris pore size. Because macromolecules are not rigid, even 2 MDa FITC-dextran can eventually adopt a conformation that allows passage through fenestra of a choriocapillary. On the other hand, small polystyrene microspheres (20 nm in diameter), which are rigid and are not able to adopt different conformations, were still visible upon fundus examination 2 months after injection (Patel S. R. et al., *Invest Ophthalmol Vis Sci* 2012; 53:4433-4441; and (Kim Y. C. et al., *Eur J Pharm Biopharm* 2015; 95:398-406). Diffusion across sclera is likely the other main mechanism for clearance. Experimental studies and theoretical analysis have shown that scleral permeability decreases as a steep function of molecular mass (Prausnitz M. R. et al., *J Pharm Sci* 1998; 87:1479-1488; and Edwards A. et al., *Pharmaceutical research* 2001; 18:1497-1508).

Figure 13:
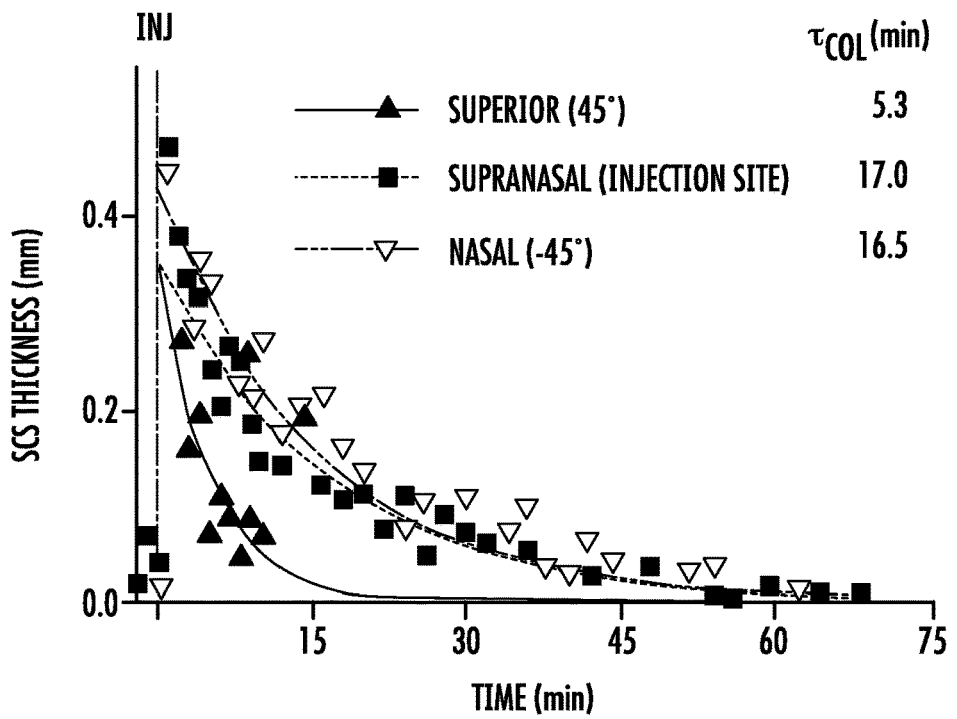
FIG. 13 depicts a quantification of SCS thickness (mean only, N=2-6 replicates) 2 mm posterior to scleral spur at three locations in various embodiments; the SEM for all time points ranged from 0.00 to 0.21 mm with a mean of 0.06 mm.

The SCS collapse rate as a measure of fluid clearance rate from the SCS was determined in live rabbits after microneedle injection of HBSS into the SCS (FIG. 13).

Under typical conditions before injection, sclera and choroid in rabbits were apposed, since the SCS is normally collapsed. Upon microneedle injection, fluid was introduced into the SCS, which caused the choroid to distend and lift off the sclera. This created a gap between sclera and choroid when viewed under ultrasound B scan, which was tracked over time and used as a proxy for SCS collapse rate and fluid clearance rate. Since SCS expansion due to HBSS can be measured directly in this way, no tracers or contrast agents were added to the fluid. After 50 µL injection in the supranasal position, the collapse of SCS was tracked as a function of time directly over the injection site and also superiorly and nasally, as depicted at FIG. 13. Data were fit to an exponential decay ($r^2$=0.62-0.71). One minute after injection, SCS thickness over the injection site was 470±60 µm (mean±SEM). The collapse time constant ($\tau_{col}$) was 19 min [15; 27 min 95% CI]. SCS expansion was indistinguishable from pre-injection thickness by 40 minutes post-injection. There was no significant difference in curve fits for measurements made supranasally or nasally (p=0.89, F test). Collapse rate of the superior SCS ($\tau$=5.5 min [3.9; 9.4 min]) was significantly faster than at the other two positions measured (p<0.05, F test). This could have been due to nearby perivascular drainage routes.

Clearance Rate of Fluorescent Molecules from the SCS:

Clearance rates were determined for different-sized fluorescent molecules and a fluorescent nanoparticle (20 nm diameter) injected as solutions into the SCS of live rabbits. The molecules ranged in molecular weight from 332 Da (fluorescein) to 2 MDa (FITC-dextran), which corresponds to effective molecular diameters of roughly 1 nm (Ambati J. et al., *Invest Ophthalmol Vis Sci* 2000; 41:1181-1185) to 54 nm (Kano M. R. et al., *Proc Natl Acad Sci USA* 2007; 104:3460-3465; and Dreher M. R. et al., *J Natl Cancer Inst* 2006; 98:335-344), respectively.

Bright-field and fluorescence fundus images were acquired for each fluorescent molecule tested over time. Since the rabbits were albino, the eyes were unpigmented, which made choroidal vessels readily visible beneath the inner retinal vessels. Furthermore, there was no detectable green autofluorescence with the light level used.

After injection, fluorescent molecules and nanoparticles were visible in SCS; localization in SCS (i.e., behind the choroid) was confirmed by shadowing of choroidal vessels over the green fluorescence. Three minutes after injection, fluorescein in HBSS and 2 MDa FITC-dextran in HBSS distributed similarly in SCS, occupying 56±6% and 58±7% of the visible SCS respectively (p=0.95, Dunnett's test). Both fluorescein and 2 MDa FITC-dextran covered larger areas of SCS than the nanoparticles (28±6%; p<0.05, Dunnett's test).

The rate of clearance also was determined by determining (i) total clearance time and (ii) clearance time constant ($\tau_{clearance}$) calculated using a curve fit derived from the normalized concentration of total fluorescent signal over time. The total clearance time was defined as the first time point post-injection where fluorescence was not detected in fundus images with the middle light intensity. Representative time courses for fluorescein and 2 MDa FITC-dextran showed rates of clearance and calculated total clearance time. In the representative images, fluorescein was not visible by 1 day, whereas 2 MDa FITC-dextran was not totally cleared until 21 days.

Figure 14:
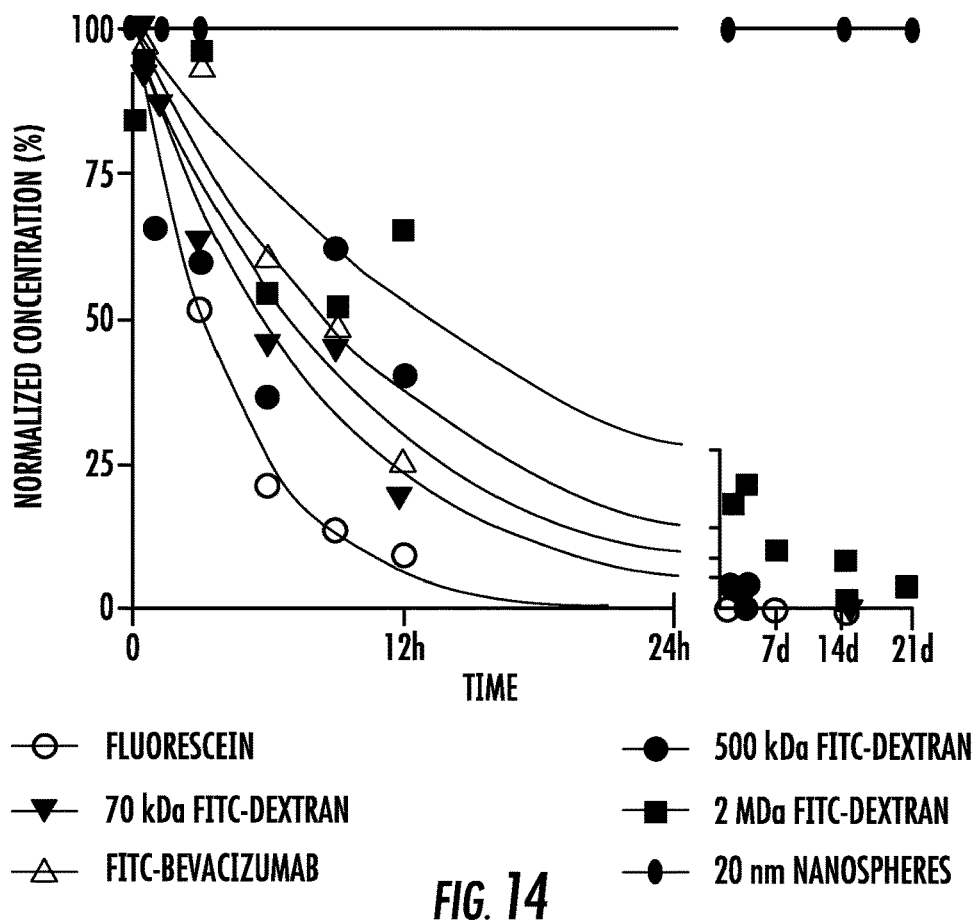
FIG. 14 depicts a quantification of fluorescein/FITC-concentration with curve fit to an exponential decay.
Figure 15:
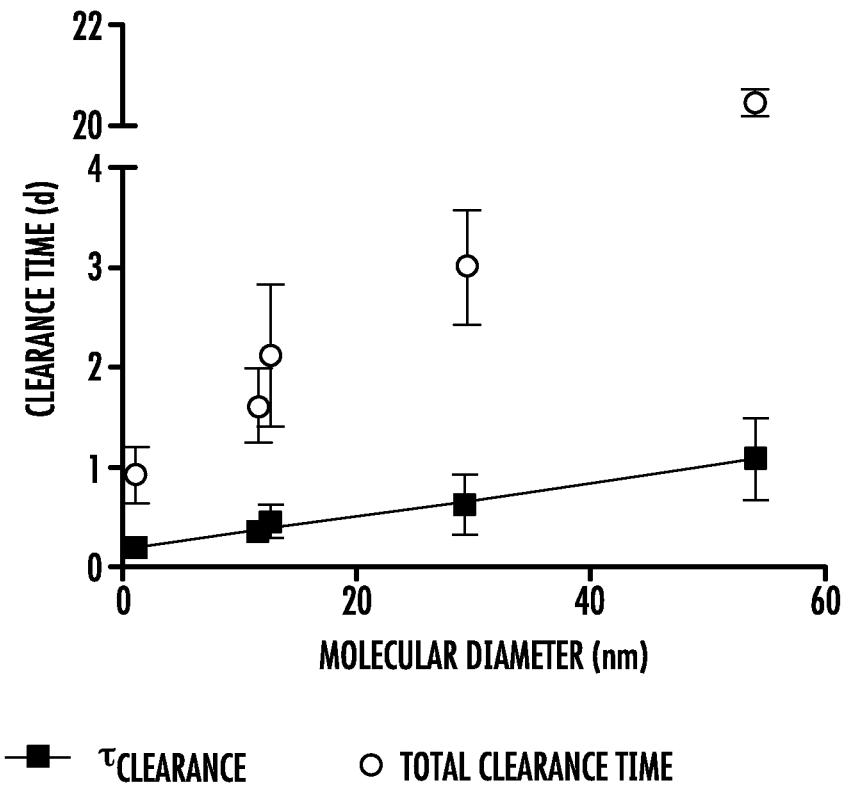
FIG. 15 depicts a clearance time constant from and total clearance time plotted against hydrodynamic molecular diameter for various embodiments.

Fluorescence was tracked via fundus examinations with a series of lighting conditions, and used to estimate relative concentration of fluorescent molecules over time in SCS. For each fluorescent molecule, data were fit to an exponential decay ($r^2>0.84$; FIG. 14). Time constants from curve fits are depicted at FIG. 15 (closed squares), along with total clearance time (open circles) for all fluorescent species tested.

Clearance time constant was linearly dependent on molecular diameter (FIG. 15, $r^2=0.87$), varying from 4.3±0.4 h for fluorescein and 26±9.8 h for 2 MDa FITC-dextran. Total clearance time could also be fit to a line (FIG. 15, $r^2=0.43$), but appeared to show nonlinearity at high molecular size. While clearance time constant had a value similar to total clearance time for the smaller molecules, total clearance time was greater for the larger molecules, suggesting a biphasic clearance rate for which a fraction of the larger molecules persisted in SCS for a longer time. Nanoparticles were not cleared from SCS for the duration of the study (>2 months). Despite differences in molecular weight and chemical structure between FITC-dextran and FITC-bevacizumab, clearance times were similar likely due to comparable hydrodynamic diameter of 70 kDa FITC-dextran (~12 nm (Ambati J. et al. *Invest Ophthalmol Vis Sci* 2000; 41:1181-1185)) and FITC-bevacizumab (~11 nm (Ambati J. et al., *Invest Ophthalmol Vis Sci* 2000; 41:1181-1185; and Wen H. et al., *J Pharm Sci* 2013; 102:892-903)), consistent with a dominant role of molecular diameter in determining SCS clearance.

Intravitreal and SCS Pressure Measurements:

VH pressure trace after IVT injection was consistent with prior literature, showing a roughly exponential decay in pressure that returned to within 10% of baseline value within 15 min (Kim Y. C. et al., *Adv Healthc Mater* 2014; 3:1272-1282; and Benz M. S. et al., *Ophthalmology* 2006; 113:1174-1178). Furthermore, VH pressure after SCS injection followed a similar timecourse, returning to within 10% of baseline value by 15 minutes. VH and SCS pressure traces were within ±1 mmHg of each other throughout the length of the experiment. Thus, it was concluded that the time course of pressure decay in the eye was the same after IVT or SCS injection.

Figure 16:
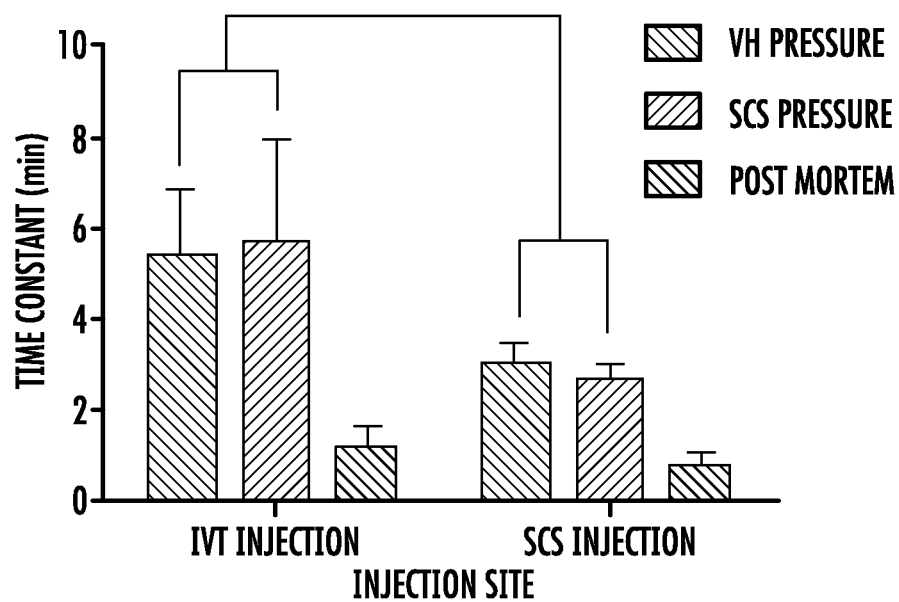
FIG. 16 depicts pressure-decay time constants derived from fitting data from several embodiments to an exponential decay.

Each data set was fit to an exponential decay, from which a pressure-decay time constant ($\tau_{pressure}$) was calculated (FIG. 16). There was no significant difference between any of the four time constants derived from VH and SCS pressure curve fits after IVT or SCS injection in vivo (p=0.98, 2-way ANOVA).

Injections made postmortem in companion eyes resulted in significantly faster depressurization (~1 minute) than injections in vivo (p<0.05, 2-way ANOVA). Since eyes were not enucleated and tissue degradation had likely not yet happened, the main difference between in vivo eyes and postmortem eyes appeared to be a lack of living processes, such as choroidal perfusion. Possible explanations include increased perivascular drainage (since the vortex vein is collapsed with no blood flow), or that blood volume was expelled from the eye upon SCS injection (as there was minimal resistance to venous flow and no refilling of ocular vascular beds).

Figure 17:
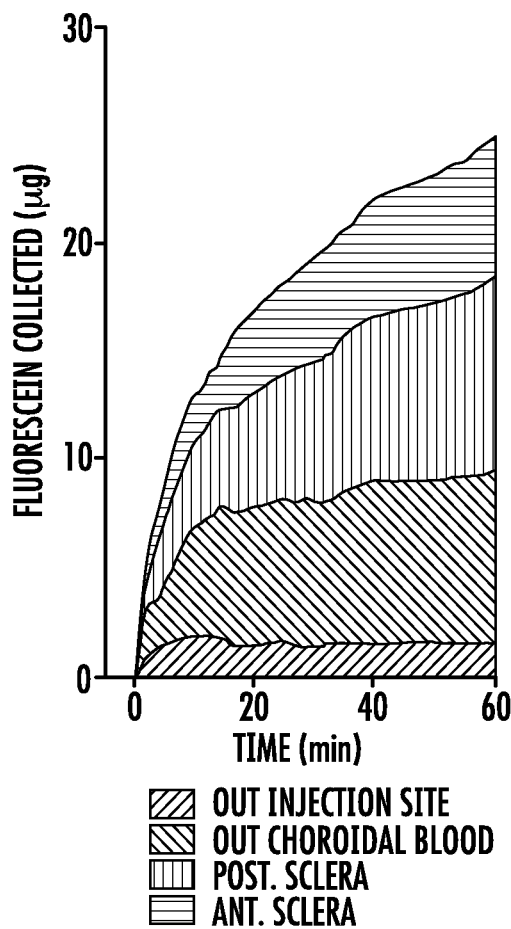
FIG. 17 depicts the total fluorescein collected over during In some embodiments.

Route of Clearance after SCS Injection:

To assess contributions of different routes of clearance, fluorescein from multiple collection sites was collected after SCS injection in vivo. The fluorescein collected from these collection sites was determined over time. The amount of fluorescein leaving through the injection site was found by subtracting site [i] from site [ii] (i.e., difference in fluorescein collected from sclera anterior to the equator without and with injection site plugged). And the amount of fluorescein leaving through blood was found by subtracting site [iv] from site [iii] (i.e., difference in fluorescein collected from sclera posterior to the equator with and without the vortex vein transected). Though the physiological data are inherently noisy, they should nevertheless enable an order of magnitude characterization of the underlying processes (which can be compared to a theoretical model of transport below). The amount of fluorescein collected over time is depicted at FIG. 17.

Figure 18:
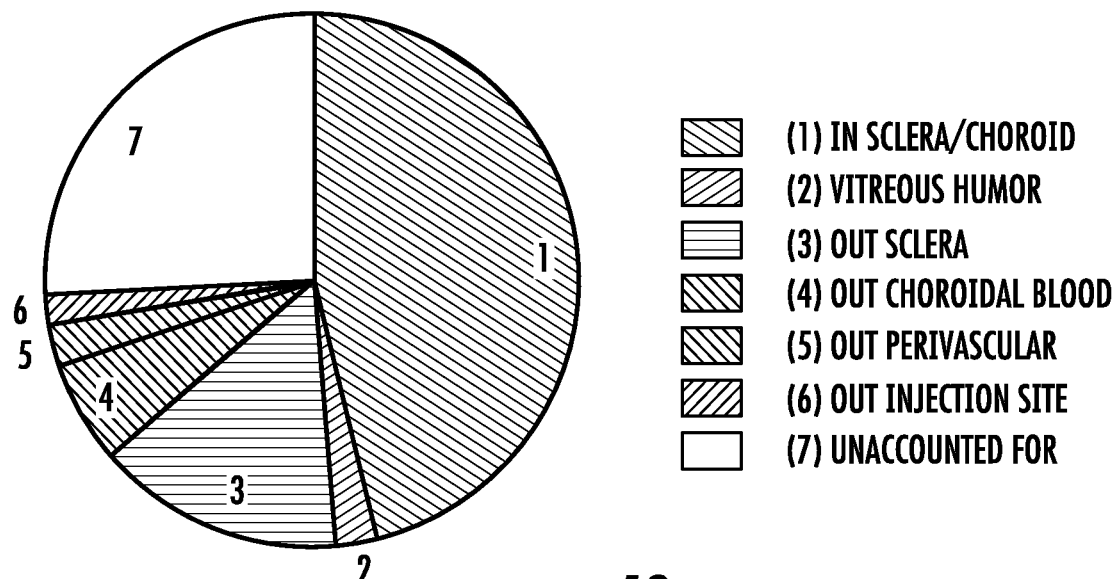
FIG. 18 depicts a quantification of total fluorescein distribution in and out of an eye after SCS injection based on cumulative fluorescein collected and analysis of residual fluorescein content in the eye after enucleation.

Cumulative amount of fluorescein collected at 1 hour, as well as residual amounts in ocular tissues, were calculated and expressed as a function of total fluorescein injected into SCS (FIG. 18). One hour post-injection, 46±18% was still within tissue (e.g., in sclera, choroid, SCS, etc.); 15±0.3% had passed transsclerally to the subconjunctival space (anterior and posterior combined); and 6.3±4% was found in blood. It was calculated that 1.3±4% exited via the injection site and 2.5±0.3% exited via perivascular drainage around the vortex vein. About 28% of the fluorescein was unaccounted for, which may have been due to collection error.

Modeling Clearance from the SCS:

At time t=0, 1000 molecules were randomly 'injected' into SCS. At each subsequent time point (time step $\Delta t=1$ minute), molecules were moved following the rules described above depending on each molecule's location at the previous time point. The location and fate of each molecule was recorded (i.e., in the eye, outside sclera, or cleared via choroid).

After 5 minutes, >95% of molecules had left the SCS. A fraction of the molecules was rapidly convected across sclera via leakage pathways at the site of injection and via perivascular routes (treated in the simulation as a single shunt pathway through the center of sclera). The remaining molecules were transported into choroid or sclera as SCS collapsed (in the simulation, SCS did not collapse). Transport into the choroid appeared to be exclusively by diffusion, since no pressure gradient from SCS across choroid was expected. Transport into sclera (i.e., not via leakage pathways) appeared to occur through a combination of diffusion and convection driven by the decaying pressure gradient across sclera.

Within 15 minutes after injection, molecules penetrated deeper into choroid and sclera, and began to be cleared from these tissues. At 1 hour, most molecules within the choroid had been cleared into the bloodstream, while molecules in the sclera continued to be cleared. The rate of clearance from choroid was determined by the rate of diffusion of molecules to capillaries and the odds of being taken up by a capillary. At 4 hours and 12 hours, transport across the sclera continued. The rate of clearance from the sclera was determined by the rate of transport to the outer scleral surface by diffusion, as well as convection driven by the normal TOP of the eye (i.e., 15 mmHg in the rabbit). It is believed that both of these driving forces may play a role in trans-scleral transport.

Figure 20:
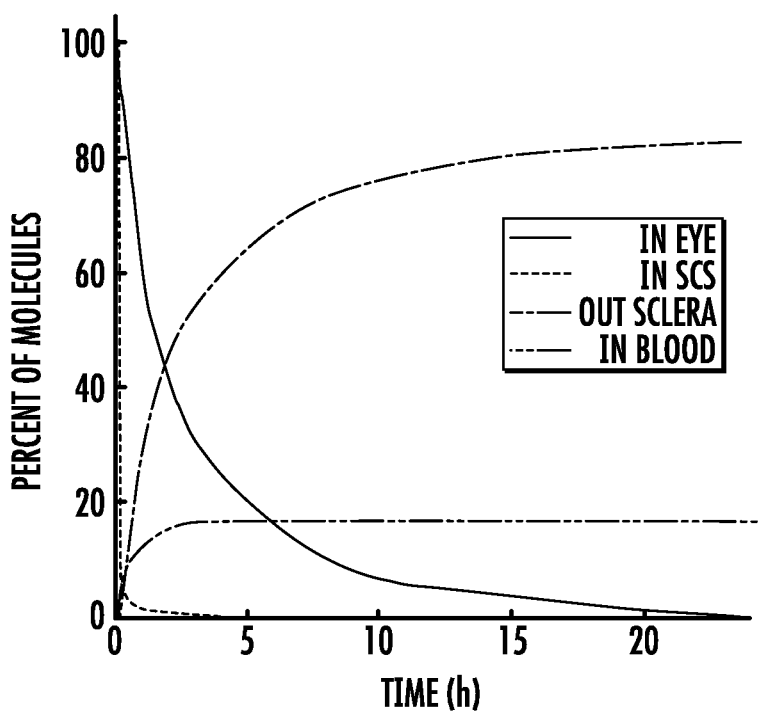
FIG. 20 depicts a percentage of particles found in an eye, in the SCS, on the exterior surface of the sclera, and in the blood via the choroid within 24 hours after injection.
Figure 21:
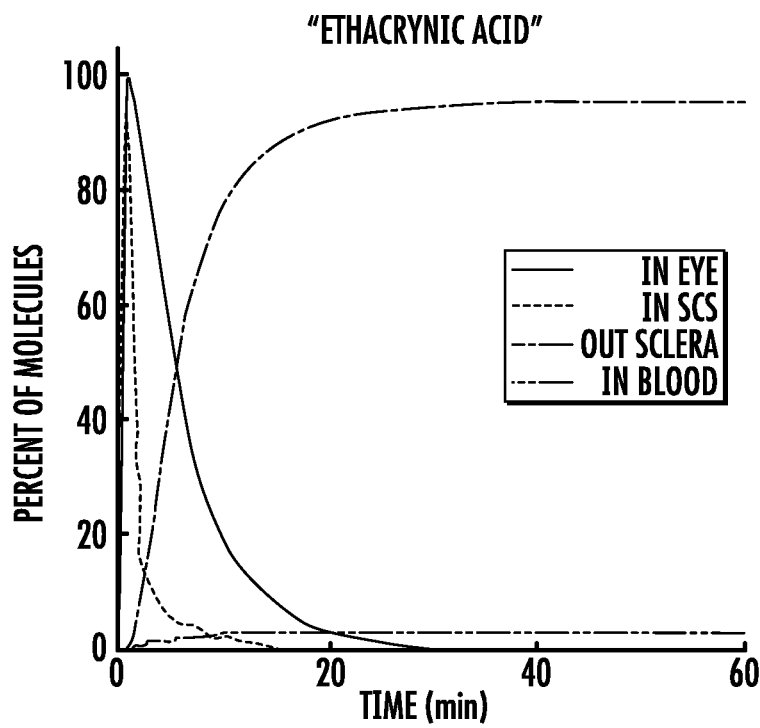
FIG. 21 depicts the summarized fate of ethacrynic acid in the eye within 1 hour after injection.
Figure 22:
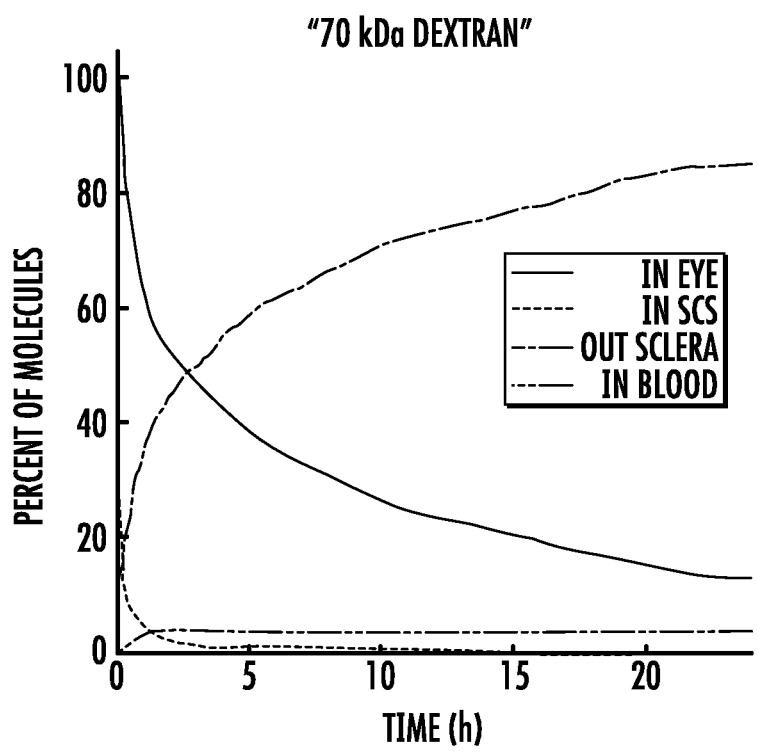
FIG. 22 depicts the summarized fate of 70 kDa Dextran in the eye within 1 hour after injection.

By 24 hours, the clearance process was largely complete. The foregoing snapshots were supplemented with continuous time course results over the course of one hour (FIG. 19) and one day (FIG. 20). This modeling result was for the low-molecular weight compound fluorescein that bound to tissue. It was believed that molecules that do not bind, e.g., ethacrynic acid (Lin C. W. et al., *Mol Vis* 2007; 13:243-251) (FIG. 21), or have higher molecular weight, e.g., 70 kDa dextran (FIG. 22), would be cleared similarly, but with different kinetics, especially for diffusion-based processes.

The model suggested that sclera accounted for more clearance than choroid. This may have been due to isotropic diffusion experienced by a molecule upon injection (as there was no pressure differential in the eye interior to sclera), and the molecule was thus able to diffuse either circumferentially within SCS or radially (towards choroid or towards sclera) at similar rates. Circumferential diffusion did not appear to affect clearance much, but radial transport likely played a major role in a molecule's eventual clearance route. If the molecule diffused into sclera, there likely was sufficient diffusive transport and convective flow due to physiological TOP across sclera to ensure clearance of the molecule across the thickness of sclera. Alternatively, if the molecule diffused into choroid, the molecule had a probability of clearing via choriocapillaries. However, if the molecule within choroid did not clear immediately, it could diffuse towards sclera and consequently become driven trans-sclerally. About one-third of molecules that diffused into choroid initially were eventually cleared through sclera.

Figure 19:
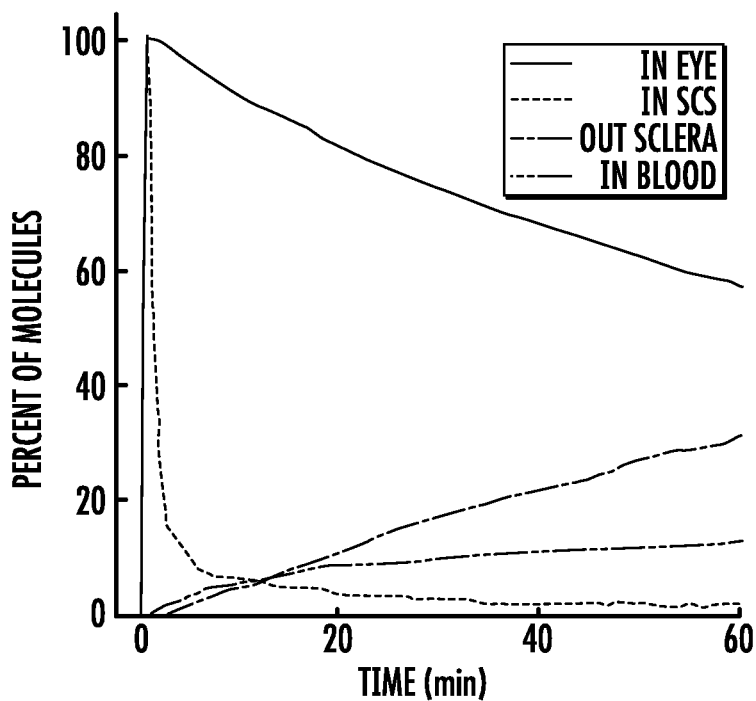
FIG. 19 depicts a percentage of particles found in an eye, in the SCS, on the exterior surface of the sclera, and in the blood via the choroid within 1 hour after injection.

Exponential curve fits were generated from model results at FIG. 19. The percentage of molecules found in the eye was fit to a $1^{st}$ order exponential decay, which yielded a time constant of 3.38 h [3.34, 3.41; 95% CI] ($r^2$=0.98). Cumulative percentage of molecules that had entered the blood via choroid was fit to a $1^{st}$ order exponential approach function with a time constant of 0.93 h [0.92, 0.94] ($r^2$=0.99). Cumulative percentage of molecules that had exited the eye via trans-scleral transport routes was fit to a $1^{st}$ order exponential approach with a time constant of 3.84 h [3.80, 3.87] ($r^2$=0.99).

Sensitivity Analysis and Effect of Parameters:

Also modeled was the behavior of a small molecule that did not bind to sclera (Lin C. W. et al., *Mol Vis* 2007; 13:243-251) and a large molecule (Ambati J. et al. *Invest Ophthalmol Vis Sci* 2000; 41:1181-1185), as summarized at FIG. 21 and FIG. 22, respectively. To model a small molecule that did not bind sclera, experimentally derived values for ethacrynic acid were used; in particular, diffusivity was increased to $5\times10^{-6}$ cm$^2$/s and $B_{max}$ was decreased to 5 µM (Lin C. W. et al., *Mol Vis* 2007; 13:243-251) (other parameters were kept the same as the fluorescein condition). The model predicted that half-life of "ethacrynic acid" in the eye to be 4.8 minutes with complete clearance by 25 minutes (see FIG. 21). These values were similar to SCS collapse time (which could be viewed as a proxy for clearance of water from SCS). Comparison of these characteristic times to those for fluorescein showed the effect that binding can have on clearance rates.

Clearance of a large macromolecule was modeled using values experimentally determined for 70 kDa FITC-dextran. In particular, diffusivity was decreased to $5\times10^{-8}$ cm$^2$/s (by assuming experimentally derived scleral permeability of $1.5\times10^{-6}$ cm/s (Ambati J. et al., *Invest Ophthalmol Vis Sci* 2000; 41:1181-1185) was at steady state across the thickness of sclera), choroidal clearance rate was decreased to 0.005 mid' (since larger molecules should have more difficulty passing through fenestrae of the choriocapillaris (Sarin H. et al., *J Angiogenes Res* 2010; 2:14)), and binding affinity $B_{max}$ was decreased to 1000 µM (Ambati J. et al., *Invest Ophthalmol Vis Sci* 2000; 41:1181-1185) while keeping other parameters the same as the fluorescein condition. The model predicted the half-life of this macromolecule to be 5.2 hours and total clearance time to be 3.8 days. Both values were within a factor of two of values determined experimentally. For all three model molecules tested, the dominant route of clearance was via trans-scleral transport with a lesser contribution from intravascular clearance in choroid.

In general, the model predicted that small changes (within 1 order of magnitude) in parameter values did not significantly change the model results. The rank order of parameter sensitivity was, from most sensitive to least: diffusivity of the molecules in the SCS and in the tissue, scleral binding capacity and equilibrium dissociation constant, vascular clearance rate, sclera hydraulic permeability, size of leakage sites, $\tau_{pressure}$ (the rate at which elevated TOP dissipated, and baseline physiological TOP. The clearance time constant observed for this example was a linear combination of the trans-scleral and vascular clearance time constants.

Diffusivity had the greatest effect on clearance times in this example; for example, reducing the diffusivities of fluorescein by one or more of magnitude to one-tenth the diffusivity of fluorescein, which resulted in a doubling of the clearance time constant. Scleral binding of molecules also had a major effect on clearance times. Increasing scleral binding appeared to behave like a decreased diffusivity by drastically slowing molecule transport. However, scleral binding affected molecule transport on short time scales (before saturating the sclera) whereas diffusivity equally affected transport at all times.

The choroidal clearance rate had a moderate effect on characteristic clearance time constant and a minor effect on total clearance time. At high clearance rates by choroidal vasculature, the choroidal perfusion contributed at most 50% of total clearance of molecules from the eye. With clearance rates set to low or nonexistent, most or all molecules left via trans-sclera pathways, which set an upper limit on the clearance time (i.e., it took about 25 hours for all molecules to leave the eye trans-sclerally).

The scleral hydraulic permeability and size of the leakage pathways had a moderate effect on clearance time. These parameters were indirectly related to trans-scleral transport. Parameters that increased the convective flow rate had a modest effect on clearance time. Therefore, convective flow through the sclera may not have been a major contributor to clearance.

All reagents and chemicals were purchased from Sigma-Aldrich (St. Louis, Mo.) unless otherwise specified. All experiments were performed in albino New Zealand White rabbits (Charles River, Wilmington, Mass.).

Microneedle Injection:

Rabbits were anesthetized with isoflurane, and an eye drop of proparacaine (Bausch & Lomb, Rochester, N.Y.) was given as a topical anesthetic prior to injection. For all experiments, a 50 µL injection was performed into the SCS of each eye with a 33-gauge microneedle ~750 µm in length (Clearside Biomedical, Alpharetta, Ga.) and a 1 mL syringe. All injections were made in the supranasal quadrant 3 mm posterior to the limbus and 4 mm nasal to the superior rectus muscle. Four eyes of four animals were used in each group unless otherwise specified. The 50 µL injection occurred in 3 seconds. After injection, the needle was kept in place for 1 minute to limit reflux at the injection site.

Determination of SCS Collapse Rate by Ultrasonography:

High-frequency ultrasound B-scan (U/S; UBM Plus, Accutome, Malvern, Pa.) was used to determine the rate of SCS collapse after microneedle injection of 50 µL Hank's Balanced Salt Solution (HBSS; Mediatech, Manassas, Va.) into SCS. Serial images were acquired every minute for 10 minutes, and then every 2 minutes for 1 hour. Off-line post processing was performed on U/S views to determine SCS thickness so the characteristic time of SCS collapse could be determined.

Determination of SCS Clearance Kinetics by Fundus Imaging:

To study the effect(s) of molecular radius on clearance from SCS, a 50µ·L microneedle injection of the following formulations was tested: [i] 0.025% (w/v) fluorescein sodium; [ii] 0.5% (w/v) 70 kDa FITC-dextran; [iii] 0.5% (w/v) 500 kDa FITC-dextran; [iv] 0.5% (w/v) 2 MDa FITC—dextran; [v] 1.5% (w/v) FITC—bevacizumab; and [vi] 1% (w/v) 20 nm green-fluorescent particles (Excitation: 505 nm, Emission: 515 nm; FluoSpheres, Life Technologies, Carlsbad, Calif.), all formulated in HBSS. These concentrations were chosen so the fluorescent intensity did not oversaturate the fundus camera sensor. Prior to injection, FITC was tagged to bevacizumab.

The clearance rate of injected fluorescent material from SCS was estimated by taking fluorescence fundus images over time. Topical eye drops of tropicamide and phenylephrine (Alcorn, Lake Forest, Ill.) were administered prior to each imaging session to dilate the pupil. A RetCam II (Clarity Medical Systems, Pleasanton, Calif.) with the 130° lens attachment and the built-in fluorescein angiography module was used to acquire images. Serial fundus collages were acquired for ≤28 days.

Intraocular Pressure Measurements:

A custom-designed pressure measurement system was used to measure pressure in vitreous humor (VH) and in SCS after either IVT or SCS injection. The animal was terminally anesthetized by subcutaneous injection of a ketamine/xylazine cocktail. After SCS or IVT injection (N=4 per injection site), pressure in the SCS and VH was alternatively measured every few minutes. Pressures were monitored until they had reached their original baseline values from before injection (i.e., ~15 mmHg). After the measurements, the animal was euthanized with a lethal dose of pentobarbital injected intravenously. A second set of SCS and IVT injections was made in the animal postmortem. In postmortem measurements, pressure was only measured in the tissue space (i.e., SCS or VH) where the injection was made.

Collection of Fluorescein by Different Clearance Routes:

For this terminal experiment, the rabbit (N=4 eyes per group) was anesthetized with a subcutaneous injection of ketamine/xylazine before microneedle injection; additional injections were given every 30 minutes to maintain anesthesia. Subcutaneous injection of 60 mL saline was also given on the rump to counteract fluid loss. The amount of fluorescein exiting the eye was determined by collecting samples over time from [i] sclera anterior to the equator; [ii] anterior sclera with injection site plugged; [iii] sclera posterior to the equator; and [iv] posterior sclera with vortex vein transected.

Prior to microneedle injection, the supranasal conjunctiva was dissected off the sclera. A 50 μL microneedle injection was performed 4 mm nasal to the superior rectus muscle and 3 mm posterior to the limbus. In [i] anterior sclera and [iii] posterior sclera conditions, samples were collected for 1 hour by swabbing the space with a 1 cm×1 cm paper tissue (Kimwipe, Kimberley-Clark, Irving, Tex.). Care was taken to swab only anterior or posterior to the equator, depending on the condition. The tissue was then placed in 1 mL HBSS until analysis.

To determine the amount of fluorescein leaving [ii] the anterior sclera with injection site plugged, a similar experiment was performed. Immediately post-injection, the injection site was plugged by sealing the microneedle into sclera with cyanoacrylate glue (Loctite 4013, Düsseldorf, Germany). Other methods were the same as above.

For eyes that had a vortex vein cut [iv], the superior vortex vein was transected prior to injection. Heparin (5 mL of 10,000 IU/mL; Hospira, Lake Forest, Ill.) was given intravenously prior to the start of the experiment to prevent coagulation. The superior rectus muscle was lifted off the ocular surface to expose the vortex vein, which was confirmed by verifying its path (i.e., originating from within sclera and traveling posteriorly along the ocular surface towards the optic nerve). A transfer pipette was used to collect blood exiting the vortex vein for 1 hour. The volume of collected blood was recorded, and HBSS was added to reach a final volume of 2 mL per sample for analysis.

Immediately after the last time point, all animals were euthanized by injection of pentobarbital through the marginal ear vein. Eyes were enucleated to determine the amount of fluorescein remaining (i) within the tissue (including SCS), and (ii) in aqueous humor, vitreous humor, and lens. The Kimwipe paper tissue and ocular tissue samples were placed in HBSS at 4° C. for 2 days to allow fluorescein to diffuse out and equilibrate with the HBSS. The amount of fluorescein in all samples was measured using a multi-plate reader (Excitation: 494 nm, Emission: 521 nm, Synergy H4, BioTek, Winooski, Vt.). In a separate experiment involving incubation of Kimwipes in a known amount of fluorescein, we found no evidence of loss in extracting fluorescein from the Kimwipe, and no leaching of fluorescent species out of the Kimwipe.

Data and Statistical Analysis:

Prism and Matlab software were used to perform data and statistical analysis. Data were fit to exponential decays to find relevant parameters (e.g., time constant) using the formula $y(t) = Y_0 e^{(-t/\tau)}$, where t is time post-injection, y(t) is SCS thickness or fluorescent-molecule fluorescence at time t, $Y_0$ is maximum SCS thickness or fluorescence, and T is characteristic time constant of SCS collapse or fluorescent molecule clearance. Other data were fit to an exponential approach function, $N(t) = N_0(1 - e^{(-t/\tau)})$, where t is time post-injection, N(t) is cumulative amount of fluorescein collected at time t, $N_0$ is maximum amount of fluorescein, and τ is characteristic time constant.

All values are reported in this example either as mean±standard error of the mean (mean±SEM), or mean and 95% confidence interval (mean [95% CI]), unless otherwise specified. One-way ANOVA analysis was performed to determine statistical significance (α=0.05) among multiple conditions. F test was used to compare parameters generated by curve fits.

Modeling Clearance from the SCS:

We developed a two-dimensional model (2D) of small-molecule transport after microneedle injection into SCS to corroborate the experimental results. This model utilized a modified random walk algorithm to study position and disposition of molecules by displacing the molecule at each time point in 2D based on the characteristic diffusional length a molecule would move in that time period, as well as additional tissue-specific rules.

We claim:

1. A fluid formulation for administration to a suprachoroidal space of an eye of a patient comprising:
   a pharmaceutical agent and a binding molecule to which the pharmaceutical agent is directly and covalently bonded;
   wherein the binding molecule has a non-particulate structure; and
   wherein the pharmaceutical agent and the binding molecule together have (i) a hydrodynamic radius of at least 7 nm, (ii) a combined molecular weight of at least 500 kDa, or (iii) a combination thereof.

2. The fluid formulation of claim 1, wherein the pharmaceutical agent and the binding molecule have a combined molecular weight of at least 1 MDa.

3. The fluid formulation of claim 1, wherein the pharmaceutical agent and the binding molecule have a combined molecular weight of at least 2 MDa.

4. The fluid formulation of claim 1, wherein the pharmaceutical agent and the binding molecule together have a hydrodynamic radius of at least 10 nm.

5. The fluid formulation of claim 1, wherein the pharmaceutical agent and the binding molecule are components of a gel.

6. The fluid formulation of claim 1, wherein the binding molecule is configured to bond to an ocular tissue covalently, non-covalently, or a combination thereof.

7. The fluid formulation of claim 1, wherein the binding molecule is a polymer.

8. The fluid formulation of claim 7, wherein the polymer is configured to crosslink in the suprachoroidal space.

9. The fluid formulation of claim 7, wherein the polymer is configured to form a gel in the suprachoroidal space.

10. The fluid formulation of claim 1, wherein the pharmaceutical agent comprises a monoclonal antibody.

11. The fluid formulation of claim 1, wherein the binding molecule comprises carboxymethylcellulose, dextran, hyaluronic acid, polyethylene glycol, chondroitin sulfate, or a combination thereof.

12. The fluid formulation of claim 1, wherein the pharmaceutical agent and the binding molecule comprise a prodrug, wherein, after administration to the suprachoroidal space, the pharmaceutical agent and the binding molecule disassociate by chemical reaction, enzymatic activity, an alteration of an attractive and/or repulsive interaction, or a combination thereof.

13. The fluid formulation of claim 12, wherein the attractive and/or repulsive interaction comprises an electrostatic interaction, a hydrophobic interaction, or a combination thereof.

14. The fluid formulation of claim 1, wherein the binding molecule is configured to precipitate in the suprachoroidal space.

15. A method for administering a pharmaceutical agent to an eye of a patient comprising:
inserting a microneedle into the eye at an insertion site; and
infusing a volume of the fluid formulation of claim 1 through the microneedle into the suprachoroidal space of an eye at the insertion site,
wherein the pharmaceutical agent administered by the method has a clearance time that is at least 2 times greater than a comparative pharmaceutical agent administered in the absence of the binding molecule.

16. The method of claim 15, wherein the pharmaceutical agent administered by the method has a clearance time that is at least 10 times greater than a comparative pharmaceutical agent administered in the absence of the binding molecule.

17. The method of claim 15, wherein the pharmaceutical agent has a clearance time from the suprachoroidal space of 3 days to 365 days.

18. The method of claim 15, wherein the pharmaceutical agent has a clearance time from the suprachoroidal space of 1 day to 21 days.

* * * * *